(12) United States Patent
Wall et al.

(10) Patent No.: US 10,688,202 B2
(45) Date of Patent: Jun. 23, 2020

(54) METAL(LOID) CHALCOGEN NANOPARTICLES AS UNIVERSAL BINDERS FOR MEDICAL ISOTOPES

(71) Applicant: Memorial Sloan Kettering Cancer Center, New York, NY (US)

(72) Inventors: Matthew A. Wall, New York, NY (US); Travis Shaffer, New York, NY (US); Stefan Harmsen, New York, NY (US); Jan Grimm, New York, NY (US); Moritz F. Kircher, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 10 days.

(21) Appl. No.: 15/329,876

(22) PCT Filed: Jul. 28, 2015

(86) PCT No.: PCT/US2015/042441
§ 371 (c)(1),
(2) Date: Jan. 27, 2017

(87) PCT Pub. No.: WO2016/018896
PCT Pub. Date: Feb. 4, 2016

(65) Prior Publication Data
US 2017/0266328 A1    Sep. 21, 2017

Related U.S. Application Data

(60) Provisional application No. 62/030,005, filed on Jul. 28, 2014.

(51) Int. Cl.
*A61K 51/12* (2006.01)
*A61K 51/02* (2006.01)
*B82Y 15/00* (2011.01)

(52) U.S. Cl.
CPC ........ *A61K 51/1244* (2013.01); *A61K 51/025* (2013.01); *A61K 51/1251* (2013.01); *B82Y 15/00* (2013.01)

(58) Field of Classification Search
CPC .............. A61K 51/1244; A61K 51/025; A61K 51/1251; B82Y 15/00
See application file for complete search history.

(56) References Cited

U.S. PATENT DOCUMENTS

| | | |
|---|---|---|
| 4,127,329 A | 11/1978 | Chang et al. |
| 4,604,992 A | 8/1986 | Sato |
| 4,669,467 A | 6/1987 | Willett et al. |
| 4,938,205 A | 7/1990 | Nudelman |
| 5,275,594 A | 1/1994 | Baker et al. |
| 5,293,872 A | 3/1994 | Alfano et al. |
| 5,300,097 A | 4/1994 | Lerner et al. |
| 5,306,403 A | 4/1994 | Vo-Dinh |
| 5,491,510 A | 2/1996 | Gove |
| 5,594,497 A | 1/1997 | Ahern et al. |
| 5,609,907 A | 3/1997 | Natan |
| 5,713,364 A | 2/1998 | DeBaryshe et al. |
| 5,721,102 A | 2/1998 | Vo-Dinh |
| 5,813,987 A | 9/1998 | Modell et al. |
| 5,949,388 A | 9/1999 | Atsumi et al. |
| 6,002,471 A | 12/1999 | Quake |
| 6,006,126 A | 12/1999 | Cosman |
| 6,008,889 A | 12/1999 | Zeng et al. |
| 6,019,719 A | 2/2000 | Schulz et al. |
| 6,025,202 A | 2/2000 | Natan |
| 6,127,120 A | 10/2000 | Graham et al. |
| 6,174,291 B1 | 1/2001 | McMahon et al. |
| 6,174,677 B1 | 1/2001 | Vo-Dinh |
| 6,219,137 B1 | 4/2001 | Vo-Dinh |
| 6,228,076 B1 | 5/2001 | Winston et al. |
| 6,242,264 B1 | 6/2001 | Natan et al. |
| 6,251,127 B1 | 6/2001 | Biel |
| 6,254,852 B1 | 7/2001 | Glajch et al. |

(Continued)

FOREIGN PATENT DOCUMENTS

| | | |
|---|---|---|
| CN | 101679022 A | 3/2010 |
| CN | 102015020 A | 4/2011 |

(Continued)

OTHER PUBLICATIONS

Adiseshaiah, P.P. et al., Nanomaterial standards for efficacy and toxicity assessment, Advanced Review, 2:99-112 (2009).
Agarwal, A. et al., Targeted gold nanorod contrast agent for prostate cancer detection by photoacoustic imaging, Journal of Applied Physics, 102:064701-064704 (2007).
Aggarwal, S. et al., What's fueling the biotech engine—2009-2010, Nature Biotechnology, 28(11):1165-1171 (2010).
Beljebbar, A. et al., Ex vivo and in vivo diagnosis of C6 glioblastoma development by Raman spectroscopy coupled to a microprobe, Anal Bioanal Chem, 398:477-487 (2010).

(Continued)

*Primary Examiner* — Robert S Cabral
(74) *Attorney, Agent, or Firm* — Wolf, Greenfield & Sacks, P.C.

(57) ABSTRACT

The present disclosure, among other things, provides new technologies for preparation of medical isotope labeled metal(loid) chalcogen nanoparticles for use in medical imaging and/or therapeutic applications. Provided technologies show a number of advantages as compared with previously available options for preparing and utilizing medical isotopes, including, for example, they utilize metal(loid) chalcogen nanoparticles that serve as universal binders (e.g., via covalent or non-covalent (e.g., chelate) bonds) for medical isotopes to provide medical isotope labeled metal(loid) chalcogen nanoparticles. Surprisingly, the same metal(loid) chalcogen nanoparticles may be used to bind (e.g., covalent or non-covalent e.g., chelation) bonding) a wide variety of different useful medical isotopes without the use of traditional chelating agents.

20 Claims, 18 Drawing Sheets

(56) References Cited

U.S. PATENT DOCUMENTS

| | | |
|---|---|---|
| 6,514,767 B1 | 2/2003 | Natan |
| 6,579,726 B1 | 6/2003 | Natan et al. |
| 6,624,886 B2 | 9/2003 | Natan et al. |
| 6,640,130 B1 | 10/2003 | Freeman et al. |
| 6,788,860 B1 | 9/2004 | Treado et al. |
| 6,959,024 B2 | 10/2005 | Paldus et al. |
| 7,076,092 B2 | 7/2006 | Hollars et al. |
| 7,192,778 B2 | 3/2007 | Natan |
| 7,443,489 B2 | 10/2008 | Natan |
| 7,538,859 B2 | 5/2009 | Tearney et al. |
| 7,656,525 B2 | 2/2010 | Zhao et al. |
| 7,738,096 B2 | 6/2010 | Zhao et al. |
| 7,760,352 B2 | 7/2010 | Armstrong et al. |
| 7,826,176 B2 | 11/2010 | Shirotori et al. |
| 7,829,140 B1 | 11/2010 | Zhong et al. |
| 8,054,463 B2 | 11/2011 | Morris et al. |
| 8,320,650 B2 | 11/2012 | Demos et al. |
| 8,409,862 B2 | 4/2013 | Caulfield et al. |
| 8,409,863 B2 | 4/2013 | Natan et al. |
| 8,416,405 B2 | 4/2013 | Panza et al. |
| 8,497,131 B2 | 7/2013 | Natan et al. |
| 8,568,878 B2 | 10/2013 | Wilson et al. |
| 8,771,978 B2 | 7/2014 | Ragan |
| 8,795,628 B2 | 8/2014 | Gambhir et al. |
| 8,918,161 B2 | 12/2014 | Natan et al. |
| 9,086,533 B1 | 7/2015 | Wach |
| 9,295,391 B1 | 3/2016 | Tearney et al. |
| 9,561,292 B1 | 2/2017 | Vo-Dinh et al. |
| 9,833,144 B2 | 12/2017 | Kircher et al. |
| 10,105,456 B2 | 10/2018 | Harmsen et al. |
| 10,322,194 B2 | 6/2019 | Kircher et al. |
| 2002/0045266 A1 | 4/2002 | Fenniri |
| 2002/0082498 A1 | 6/2002 | Wendt et al. |
| 2002/0163482 A1 | 11/2002 | Sullivan |
| 2002/0165594 A1 | 11/2002 | Biel |
| 2003/0055307 A1 | 3/2003 | Elmaleh et al. |
| 2003/0191379 A1 | 10/2003 | Benaron et al. |
| 2003/0201208 A1 | 10/2003 | Koch et al. |
| 2004/0009341 A1 | 1/2004 | Naasani |
| 2004/0010192 A1 | 1/2004 | Benaron et al. |
| 2004/0073120 A1 | 4/2004 | Motz et al. |
| 2004/0225222 A1 | 11/2004 | Zeng et al. |
| 2004/0254419 A1 | 12/2004 | Wang et al. |
| 2004/0254454 A1 | 12/2004 | Kockro |
| 2005/0014851 A1 | 1/2005 | Bringley |
| 2005/0074779 A1 | 4/2005 | Vo-Dinh |
| 2005/0143662 A1 | 6/2005 | Marchitto et al. |
| 2005/0221494 A1 | 10/2005 | Natan |
| 2005/0272160 A1 | 12/2005 | Natan |
| 2005/0277816 A1 | 12/2005 | Maier et al. |
| 2006/0008924 A1 | 1/2006 | Anker et al. |
| 2006/0054506 A1 | 3/2006 | Natan et al. |
| 2006/0098194 A1 | 5/2006 | Tuschel |
| 2006/0173293 A1 | 8/2006 | Marquart et al. |
| 2006/0250613 A1 | 11/2006 | Demuth et al. |
| 2007/0010809 A1 | 1/2007 | Hovda et al. |
| 2007/0134805 A1 | 6/2007 | Gilbert |
| 2007/0167838 A1 | 7/2007 | Hubble et al. |
| 2007/0178067 A1 | 8/2007 | Maier et al. |
| 2007/0196281 A1 | 8/2007 | Jin et al. |
| 2007/0232874 A1 | 10/2007 | Ince |
| 2007/0238953 A1 | 10/2007 | Lucassen et al. |
| 2007/0255356 A1 | 11/2007 | Rose et al. |
| 2007/0260295 A1 | 11/2007 | Chen et al. |
| 2007/0269382 A1 | 11/2007 | Santra et al. |
| 2007/0282190 A1 | 12/2007 | Dekel et al. |
| 2007/0299550 A1 | 12/2007 | Nishijima et al. |
| 2008/0007716 A1 | 1/2008 | Igarashi |
| 2008/0058908 A1 | 3/2008 | Bornstein |
| 2008/0089839 A1 | 4/2008 | Lu et al. |
| 2008/0095852 A1 | 4/2008 | Kong et al. |
| 2008/0118912 A1 | 5/2008 | Dickson et al. |
| 2008/0119832 A1 | 5/2008 | Cronin |
| 2008/0305045 A1 | 12/2008 | Kuniyil et al. |
| 2009/0137666 A1 | 5/2009 | Wang et al. |
| 2009/0171330 A1 | 7/2009 | Taylor et al. |
| 2009/0204111 A1 | 8/2009 | Bissig et al. |
| 2009/0218550 A1 | 9/2009 | Koyakutty et al. |
| 2009/0237648 A1 | 9/2009 | Armstrong et al. |
| 2009/0263485 A1 | 10/2009 | Li et al. |
| 2009/0281536 A1 | 11/2009 | Beckman et al. |
| 2009/0285766 A1 | 11/2009 | Kishen et al. |
| 2009/0294692 A1 | 12/2009 | Bourke, Jr. et al. |
| 2009/0304581 A1 | 12/2009 | Scheinberg et al. |
| 2010/0016783 A1 | 1/2010 | Bourke, Jr. et al. |
| 2010/0045778 A1 | 2/2010 | Yelin |
| 2010/0166650 A1 | 7/2010 | Gambhir |
| 2010/0197937 A1 | 8/2010 | Minami et al. |
| 2010/0211137 A1 | 8/2010 | Kim et al. |
| 2010/0233147 A1 | 9/2010 | Schwartz et al. |
| 2010/0279272 A1 | 11/2010 | Burrell et al. |
| 2010/0322471 A1 | 12/2010 | Treado et al. |
| 2011/0020239 A1 | 1/2011 | Bulte et al. |
| 2011/0021970 A1 | 1/2011 | Vo-Dinh et al. |
| 2011/0045081 A1 | 2/2011 | Steitz et al. |
| 2011/0123439 A1* | 5/2011 | Cheon ............... A61K 49/0002 424/1.37 |
| 2011/0152692 A1 | 6/2011 | Nie et al. |
| 2011/0165077 A1 | 7/2011 | Qian et al. |
| 2011/0182881 A1 | 7/2011 | Chin et al. |
| 2011/0190760 A1 | 8/2011 | Niver et al. |
| 2011/0207231 A1 | 8/2011 | Natan et al. |
| 2011/0230760 A1 | 9/2011 | Gambhir et al. |
| 2011/0242533 A1 | 10/2011 | Treado et al. |
| 2011/0261351 A1 | 10/2011 | Treado et al. |
| 2011/0262351 A1 | 10/2011 | Chung et al. |
| 2011/0263920 A1 | 10/2011 | Bourke, Jr. et al. |
| 2011/0282181 A1 | 11/2011 | Wang et al. |
| 2012/0123205 A1 | 5/2012 | Nie et al. |
| 2012/0136241 A1 | 5/2012 | Chen et al. |
| 2012/0141380 A1 | 6/2012 | Margel et al. |
| 2012/0141981 A1 | 6/2012 | Pantazis et al. |
| 2012/0164624 A1 | 6/2012 | Natan et al. |
| 2012/0164680 A1 | 6/2012 | McNaughton et al. |
| 2012/0179029 A1 | 7/2012 | Kircher et al. |
| 2012/0212733 A1 | 8/2012 | Kodali et al. |
| 2012/0226139 A1 | 9/2012 | Peyman |
| 2012/0251450 A1 | 10/2012 | Punnoose et al. |
| 2012/0282632 A1 | 11/2012 | Chiu et al. |
| 2012/0283379 A1 | 11/2012 | Auger et al. |
| 2012/0302940 A1 | 11/2012 | Ray |
| 2013/0012794 A1 | 1/2013 | Zeng et al. |
| 2013/0023770 A1 | 1/2013 | Courtney et al. |
| 2013/0029360 A1 | 1/2013 | Suh et al. |
| 2013/0040292 A1 | 2/2013 | Fernandez Lopez et al. |
| 2013/0137944 A1 | 5/2013 | Jeong et al. |
| 2013/0231573 A1 | 9/2013 | Zeng et al. |
| 2013/0309280 A1 | 11/2013 | Choi et al. |
| 2013/0330839 A1 | 12/2013 | Suh et al. |
| 2013/0342683 A1 | 12/2013 | Nelson et al. |
| 2014/0140594 A1 | 5/2014 | Mahadevan-Jansen et al. |
| 2014/0316255 A1 | 10/2014 | Garai et al. |
| 2014/0350534 A1 | 11/2014 | Kircher et al. |
| 2015/0018807 A1 | 1/2015 | Kircher et al. |
| 2015/0125952 A1 | 5/2015 | Kim et al. |
| 2015/0182296 A1 | 7/2015 | Daon et al. |
| 2015/0258218 A1 | 9/2015 | Kircher et al. |
| 2015/0328346 A1 | 11/2015 | Harmsen et al. |
| 2016/0000329 A1 | 1/2016 | Kircher et al. |
| 2016/0000330 A1 | 1/2016 | Huang et al. |
| 2016/0018404 A1 | 1/2016 | Iyer et al. |
| 2016/0166194 A1 | 6/2016 | Gareau et al. |
| 2016/0367668 A1 | 12/2016 | Kircher et al. |
| 2017/0138860 A1 | 5/2017 | Huang |
| 2017/0296293 A1 | 10/2017 | Mak et al. |
| 2018/0271502 A1 | 9/2018 | Zarrine-Afsar |

FOREIGN PATENT DOCUMENTS

| | | |
|---|---|---|
| CN | 102175655 A | 9/2011 |
| CN | 102410994 A | 4/2012 |
| CN | 102559190 A | 7/2012 |
| CN | 102686181 A | 9/2012 |
| CN | 102770071 A | 11/2012 |

(56) References Cited

FOREIGN PATENT DOCUMENTS

| | | |
|---|---|---|
| DE | 102 49 674 A1 | 5/2004 |
| DE | 102005030986 A1 | 1/2007 |
| DE | 10 2011 103 950 A1 | 12/2012 |
| EP | 2671613 A2 | 12/2013 |
| JP | H09-005666 A | 1/1997 |
| JP | H11-084307 A | 3/1999 |
| JP | 2002-534199 A | 9/2002 |
| JP | 2003/503135 A | 1/2003 |
| JP | 2004/193545 A | 7/2004 |
| JP | 2005 306827 A | 11/2005 |
| JP | 2009/011546 A | 1/2009 |
| JP | 2009/508571 A | 3/2009 |
| JP | 2009/511891 A | 3/2009 |
| JP | 2009/115546 A | 5/2009 |
| JP | 2009/222713 A | 10/2009 |
| JP | 2010/523983 A | 7/2010 |
| JP | 2011-158334 A | 8/2011 |
| TW | 572748 B | 1/2004 |
| WO | WO-90/03803 A1 | 4/1990 |
| WO | WO-93/03672 A1 | 3/1993 |
| WO | WO-00/41611 A2 | 7/2000 |
| WO | WO-01/01854 A2 | 1/2001 |
| WO | WO 2001/81923 A1 | 11/2001 |
| WO | WO-02/100285 A1 | 12/2002 |
| WO | WO-2005/107623 A2 | 11/2005 |
| WO | WO-2008/122035 A1 | 10/2008 |
| WO | WO-2010/096828 A1 | 8/2010 |
| WO | WO-2010/111066 A2 | 9/2010 |
| WO | WO-2011/025640 A1 | 3/2011 |
| WO | WO-2011/084528 A1 | 7/2011 |
| WO | WO-2012/065163 A2 | 5/2012 |
| WO | WO 2012/070893 A2 | 5/2012 |
| WO | WO 2012/166796 A1 | 12/2012 |
| WO | WO-2014/036470 A1 | 3/2014 |
| WO | WO-2014/089247 A2 | 6/2014 |
| WO | WO-2014/100380 A2 | 6/2014 |
| WO | WO-2014/130736 A1 | 8/2014 |
| WO | WO 2015/134620 A1 | 9/2015 |
| WO | WO-2016/028749 A1 | 2/2016 |
| WO | WO-2016/149378 A1 | 9/2016 |
| WO | WO-2016/179260 A1 | 11/2016 |
| WO | WO 2017/040915 A1 | 3/2017 |
| WO | WO-2018/213851 A1 | 11/2018 |

OTHER PUBLICATIONS

Binkley, J. et al., RNA ligands to human nerve growth factor, Nucleic Acids Research, 23(16):3198-3205 (1995).

Bucci, M.K. et al., Near Complete Surgical Resection Predicts a Favorable Outcome in Pediatric Patients with Nonbrainstem, Malignant Gliomas, Cancer, 101(4): 817-824 (2004).

De La Zerda, A. et al., A Comparison Between Time Domain and Spectral Imaging Systems for Imaging Quantum Dots in Small Living Animals, Molecular Imaging and Biology, 12:500-508 (2010).

De La Zerda, A. et al., Advanced contrast nanoagents for photoacoustic molecular imaging, cytometry, blood test and photothermal theranostics, Contrast Media Mol. Imaging, 6:346-369 (2011).

De La Zerda, A. et al., Carbon nanotubes as photoacoustic molecular imaging agents in living mice, Letters, Nature Nanotechnology, 3:557-562 (2008).

De La Zerda, A. et al., Ultrahigh Sensitivity Carbon Nanotube Agents for Photoacoustic Molecular Imaging in Living Mice, Nano Letters, 10:2168-2172 (2010).

Debbage, P. and Jaschke, W., Molecular imaging with nanoparticles: giant roles for dwarf actors, Histochem. Cell Biol., 130(5):845-75 (2008).

Declaration of Moritz Kircher for U.S. Appl. No. 14/464,642, 16 pages, filed Dec. 5, 2016.

Eghtedari, M. et al., High Sensitivity of In Vivo Detection of Gold Nanorods Using a Laser Optoacoustic Imaging System, Nano Letters, 7(7):1914-1918 (2007).

Ermilov, S.A. et al., Laser optoacoustic imaging system for detection of breast cancer, Journal of Biomedical Optics, 14(2):024007-1-14 (2009).

Extended European Search Report for EP 13832980.0, 9 pages (dated Apr. 20, 2016).

Fales, A.M. et al., Silica-coated gold nanostars for combined surface-enhanced Raman scattering (SERS) detection and singlet-oxygen generation: a potential nanoplatform for theranostics, Langmuir, 27(19):12186-90 (2011).

Haaland, D.M. and Easterling, R.G., Improved Sensitivity of Infrared Spectroscopy by the Application of Least Squares Methods, Applied Spectroscopy, 34(5):539-548 (1980).

Harmsen, S. et al., Rational design of a chalcogenopyrylium-based surface-enhanced resonance Raman scattering nanoprobe with attomolar sensitivity, Nature Communications, 6:6570 | DOI: 10.1038/ncomms7570, pp. 1-9, Additional Information added, 8 pages.

Harmsen, S. et al., Surface-enhanced resonance Raman scattering nanostars for high-precision cancer imaging, Science Translational Medicine, 7(271):1-8 (2015).

Huang, J. et al., Preparation of Silica-Encapsulated Hollow Gold Nanosphere Tags Using Layer-by-Layer Method for Multiplex Surface-Enhanced Raman Scattering Detection, Langmuir, 27:10228-10233 (2011).

Huang, R. et al., High Precision Imaging of Microscopic Spread of Blioblastoma with a Targeted Ultrasensitive SERRS Molecular Imaging Probe, Theranostics, 6(8):1075-1084 (2016).

Huang, X. et al., Gold nanoparticles: interesting optical properties and recent applications in cancer diagnostics and therapy, Nanomedicine, 2(5):681-693 (2007).

International Preliminary Report on Patentability for PCT/US13/57636, 27 pages (dated Aug. 1, 2014).

International Search Report for PCT/US2013/057636, 3 pages (dated Jan. 3, 2014).

International Search Report for PCT/US2013/076475, 4 pages (dated Jun. 16, 2014).

International Search Report for PCT/US2014/017508, 3 pages (dated May 12, 2014).

International Search Report for PCT/US2015/042441, 3 pages (dated Oct. 19, 2015).

International Search Report for PCT/US2015/045646, 5 pages (dated Nov. 27, 2015).

Jellinek, D.J. et al., Inhibition of Receptor Binding by High-Affinity RNA Ligands to Vascular Endothelial Growth Factor, Biochemistry, 33:10450-10456 (1994).

Kaaki, K. et al., Magnetic Nanocarriers of Doxorubicin Coated with Poly(ethylene glycol) and Folic Acid: Relation between Coating Structure, Surface Properties, Colloidal Stability, and Cancer Cell Targeting, Langmuir, 28:1496-1505 (2012).

Kantelhardt, S.R. et al., Multiphoton Excitation Fluorescence Microscopy of 5-Aminolevulinic Acid Induced Fluorescence in Experimental Gliomas, Laser in Surgery and Medicine, 40:273-281 (2008).

Keren, S. et al., Noninvasive molecular imaging of small living subjects using Raman spectroscopy, PNAS, 105(15):5844-5849 (2008).

Kim, G. et al., Indocyanine-green-embedded PEBBLEs as a contrast agent of photoacoustic imaging, Journal of Biomedical Optics, 12(4):044020-1-8 (2007).

Kim, J. et al., Golden carbon nanotubes as multimodal photoacoustic and photothermal high-contrast molecular agents, Nature Nanotechnology, 4:688-694 (2009).

Kim, J. et al., Multifunctional nanostructured materials for multimodal imaging, and simultaneous imaging and therapy, Chem. Soc. Rev., 38:372-390 (2009).

Kim, K. et al., Silver-Coated Dye-Embedded Silica Beads: A Core Material of Dual Tagging Sensors Based on Fluorescence and Raman Scattering, ACS Applied Materials & Interfaces, 3:324-330 (2011).

Kim, K. et al., Silver-particle-based surface-enhanced resonance Raman scattering spectroscopy for biomolecular sensing and recognition, Anal Bioanal Chem., 388:81-88 (2007).

Kircher, M.F. et al., A brain tumor molecular imaging strategy using a new triple-modality MRI-photoacoustic-Raman nanoparticle, Nature Medicine, 18(5):829-834 (2012).

Kircher, M.F. et al., Noninvasive cell-tracking methods, Nature Reviews: Clinical Oncology, 8:677-688 (2011).

(56) References Cited

OTHER PUBLICATIONS

Knauth, M. et al., Low-field interventional MRI in neurosurgery: finding the right dose of contrast medium, Neuroradiology, 43:254-258 (2001).

Knauth, M. et al., Surgically Induced Intracranial Contrast Enhancement: Potential Source of Diagnostic Error in Intraoperative MR Imaging, AJNR Am J Neuroradiol, 20:1547-1553 (1999).

Kodali, A., et al., Optimally designed nanolayered metal-dielectric particles as probes for massively multiplexed and ultrasensitive molecular assays, PNAS, 107(31):13620-13625 (2010).

Koljenovic, S. et al., Raman Spectroscopic Characterization of Porcine Brain Tissue Using a Single Fiber-Optic Probe, Anal. Chem., 79:557-564 (2007).

Loening, A.M. and Gambhir, S.S., AMIDE: A Free Software Tool for Multimodality Medical Image Analysis, Molecular Imaging, 2(3):131-137 (2003).

Lusic, H. and Grinstaff, M.W., X-ray-computed tomography contrast agents, Chem. Rev., 113(3):1641-66 (2013).

Lüdemann, L. et al., Pharmacokinetic analysis of glioma compartments with dynamic Gd-DTPA-enhanced magnetic resonance imaging, Magnetic Resonance Imaging, 18:1201-1214 (2000).

Maeda, H. et al., Tumor vascular permeability and the EPR effect in macromolecular therapeutics: a review, Journal of Controlled Release, 65:271-284 (2000).

Mansfield, J.R. et al., Autofluorescence removal, multiplexing, and automated analysis methods for in-vivo fluorescence imaging, Journal of Biomedical Optics, 10(4):041207-1-9 (2005).

Massoud, T.F. and Gambhir, S.S., Molecular imaging in living subjects: seeing fundamental biological processes in a new light, Genes Dev., 17(5):545-80 (2003).

McNay, G. et al., Surface-Enhanced Raman Scattering (SERS) and Surface-Enhanced Resonance Raman Scattering (SERRS): A Review of Applications, Applied Spectroscopy, 65(8):825-837 (2011).

Ozawa, T. et al., Bromophenol Blue Staining of Tumors in a Rat Glioma Model, Neurosurgery, 57(4):1041-1047 (2005).

Pelletier, M.J., Quantitative Analysis Using Raman Spectrometry, 57(1):20A-42A (2003).

Qian, X. et al., In vivo tumor targeting and spectroscopic detection with surface-enhanced Raman nanoparticle tags, Nature Biotechnology, 26(1):83-90, (2008).

Razansky, D. et al., Multispectral opto-acoustic tomography of deep-seated fluorescent proteins in vivo, Nature Photonics, 3:412-417 (2009).

Reinges, M.H.T. et al., Course of brain shift during microsurgical resection of supratentorial cerebral lesions: limits of conventional neuronavigation, Acta Neurochir, 146:369-377 (2004).

Robbins, S.L. and Angell, M., Neoplasia and Other Disturbances of Cell Growth, Basic Pathology: Non-Neoplastic Cell Growth, 2(3):68-105 (1976).

Schneider, J.P. et al., Intraoperative MRI to guide the resection of primary supratentorial glioblastoma multiforme—a quantitative radiological analysis, Neuroradiology, 47:489-500 (2005).

Shinoda, J. et al., Fluorescence-guided resection of glioblastoma multiforme by using high-dose fluorescein sodium, J Neurosurg, 99:597-603 (2003).

Short, M.A. et al., Development and preliminary results of an endoscopic Raman probe for potential in vivo diagnosis of lung cancers, Optics Letters, 33(7):711-713 (2008).

Stewart et al., Raman Imaging, Annual Review of Analytical Chemistry, 5:337-360 (2012).

Stummer, W. et al., Fluorescence-guided surgery with 5-aminolevulinic acid for resection of malignant glioma: a randomised controlled multicentre phase III trial, Oncology: The Lancet, 7:392-401 (2006).

Stupp, R. et al., Changing Paradigms—An Update on the Multidisciplinary Management of Malignant Glioma, The Oncologist, 11:165-180 (2006).

Supplementary Partial European Search Report, European International Application No. 14753802.9, 8 pages, dated Oct. 20, 2016.

Thakor, A.S. et al., Oxidative Stress Mediates the Effects of Raman-Active Gold Nanoparticles in Human Cells, Nanoparticle Cytotoxicity, 7(1):126-136 (2011).

Thakor, A.S. et al., The Fate and Toxicity of Raman-Active Silica-Gold Nanoparticles in Mice, Drug Delivery, Science Translation Medicine, 3(79):1-11 (2011).

Tognalli, N. et al., From Single to Multiple Ag-Layer Modification of Au Nanocavity Substrates: A Tunable Probe of the Chemical Surface-Enhanced Raman Scattering Mechanism, ACS Nano, 5(7):5433-5443 (2011).

Toms, S.A. et al., Intraoperative Optical Spectroscopy Identifies Infiltrating Glioma Margins with High Sensitivity, Operative Neurosurgery, 57(4):382-391 (2005).

Treéhin, R. et al., Fluorescent Nanoparticle Uptake for Brain Tumore Visualization, Neoplasia, 8(4):302-311 (2006).

Tuerk, C. and MacDougal-Waugh, S., In vitro evolution of functional nucleic acids: high-affinity RNA ligands of HIV-1 proteins, Gene, 137:33-39 (1993).

Wang, L.V., Multiscale photoacoustic microscopy and computed tomography, Nature Photonics, 3:503-209 (2009).

Wieboldt, Dick, Understanding Raman Spectrometer Parameters, Spectroscopy, Special Issue, 6 pages (2010).

Written Opinion for PCT/US2013/057636, 6 pages (dated Jan. 3, 2014).

Written Opinion for PCT/US2014/017508, 12 pages (dated May 12, 2014).

Written Opinion for PCT/US2015/042441, 16 pages (dated Oct. 19, 2015).

Written Opinion for PCT/US2015/045646, 7 pages (dated Nov. 27, 2015).

Written Opinion, PCT/US2013/076475, dated Jun. 16, 2014, 8 pages.

Yigit, M.V. and Medarova, Z., In vivo and ex vivo applications of gold nanoparticles for biomedical SERS imaging, Am J Nucl Med Mol Imaging, 2(2):232-341 (2012).

Yuan, H. et al., Quantitative Surface-Enhanced Resonant Raman Scattering Multiplexing of Biocompatible Gold Nanostars for In Vitro and ex Vivo Detection, Analytical Chemistry, 85:208-212 (2012).

Zavaleta, C. et al., Noninvasive Raman Spectroscopy in Living Mice for Evaluation of Tumor Targeting with Carbon Nanotubes, Nano Letters, 8(9):2800-2805 (2008).

Zavaleta, C.L. et al., Multiplexed imaging of surface enhanced Raman scattering nanotags in living mice using noninvasive Raman spectroscopy, PNAS, 106(32):13511-13516 (2009).

Zavaleta, C.L. et al., Preclinical Evaluation of Raman Nanoparticle Biodistribution for their Potential Use in Clinical Endoscopy Imaging, Small, 7(15):2232-2240 (2011).

Zavaleta, C.L. et al., Raman's "Effect" on Molecular Imaging, J Nucl Med., 52:1839-1844 (2011).

Zhang, Y. et al., Molecular Imaging with SERS-Active Nanoparticles, Small, 7(23):3261-3269 (2011).

Zong, S. et al., A SERS and fluorescence dual mode cancer cell targeting probe based on silica coated Au@Ag core-shell nanorods, Talanta, 97:368-375 (2012).

Esenturk, E. N. and Walker, A. R. H., Surface-enhanced Raman scattering spectroscopy via gold nanostars, Journal of Raman Spectroscopy, 40(1): 86-91 (2009).

Yi, Z. et al, Facile preparation of Au/Ag bimetallic hollow nanospheres and its application in surface-enhanced Raman scattering, Applied Surface Science, 258(1): 212-217 (2011).

Yigit, M. V. et al, Noninvasive MRI-SERS Imaging in Living Mice Using an Innately Bimodal Nanomaterial, ACS NANO, 5(2): 1056-1066 (2011).

Cheng, F. et al, Chelator-Free Synthesis of a Dual-Modality PET/MRI Agent, Angew. Chem. Int. Ed., 52: 13319-13323 (2013).

Lee, S. B. et al, Mesoporous Silica Nanoparticle Pretargeting for PET Imaging Based on a Rapid Bioorthogonal Reaction in a Living Body, Angew. Chem. Int. Ed., 52: 10549-10552 (2013).

Sun, X. et al, Self-Illuminating $^{64}$Cu-Doped CdSe/ZnS Nanocrystals in Vivo Tumor Imaging, Journal of the American Chemical Society, 136: 1706-1709 (2014).

(56) References Cited

OTHER PUBLICATIONS

Sá, L. T. M. et al, Development of Nanoptamers Using a Mesoporous Silica Model Labeled with $^{99m}$Tc for Cancer Targeting, Oncology, 82: 213-217 (2012).
Von Maltzahn, G. et al., SERS-Coded Gold Nanorods as a Multifunctional Platform for Densely Multiplexed Near-Infrared Imaging and Photothermal Heating, Adv. Mater. 21:3175-3180 (2009).
Von Maltzahn et al., SERS-Coded Gold Nanorods as a Multifuntional Platform for Densely Multiplexed Near-Infrared Imaging and Photothermal Heating, Advanced Materials, 21:3175-3180, (2009).
European Search Report for Application No. EP 14753802.9, dated May 27, 2019.
International Search Report and Written Opinion for Application No. PCT/US2016/050090, dated Nov. 22, 2016.
International Search Report and Written Opinion for Application No. PCT/US2015/018746, dated May 27, 2015.
International Preliminary Report on Patentability for Application No. PCT/US2015/042441, dated Feb. 9, 2017.
Ahmed et al., Goldberg, S. N. Principles of and Advances in Percutaneous Ablation. Radiology, 258(2):351-369 (2011).
Akerman et al., Nanocrystal targeting in vivo. Proc Natl Acad Sci U S A. Oct. 1, 2002;99(20):12617-21. Epub Sep. 16, 2002.
Amstad et al., Triggered Release from Liposomes through Magnetic Actuation of Iron Oxide Nanoparticle Containing Membranes. Nano Letters, 2011;11:1664-70.
Asfari et al., Establishment of 2-Mercaptoethanol-Dependent Differentiated Insulin-Secreting Cell Lines. Endocrinology, 1992;130(1):167-178.
Bekis et al., A new agent for sentinel lymph node detection: preliminary results. J Radioanal. Nucl. Chem. 2011;290:277-82. doi: 10.1007/s10967-011-1250-4.
Bogart et al., Photothermal Microscopy of the Core of Dextran-Coated Iron Oxide Nanoparticles During Cell Uptake, ACS Nano, 2012;6(7):5961-71.
Burckhardt et al. Virus Movements on the Plasma Membrane Support Infection and Transmission between Cells, PLoS Pathogens, 2009;5(11):e1000621 :1-9.
Chen et al., Chelator-free synthesis of a dual-modality PET/MRI agent. Angew Chem Int Ed Engl. Dec. 9, 2013;52(50):13319-23. doi: 10.1002/anie.201306306. Epub Oct. 24, 2013.
Cho et al., A magnetic switch for the control of cell death signaling in in vitro and in vivo systems. Nat. Mater. 2012;11:1038-43.
Cirman et al., Selective Disruption of Lysosomes in Hela Cella Triggers Apoptosis Mediated by Cleavage of Bid by Multiple Papain-Like Lysosomal Cathepsins. J. of Biological Chem. 2004;279(5):3578-3587.
Corchero et al., Biomedical applications of distally controlled magnetic nanoparticles, Trends Biotechnol, 2009;27(8):468-476.
Creixell et al., EGFR-Targeted Magnetic Nanoparticle Heaters Kill Cancer Cells without a Perceptible Temperature Rise. ACS Nano, 2011;5(9):7124-7129.
Daniel et al., Lysosomal trapping as an important mechanism involved in the cellular distribution of perazine and in pharmacokinetic interaction with antidepressants. European Neuropsychopharmacology, 1999;9:483-491.
Dobson, Remote control of cellular behaviour with magnetic nanoparticles, Nature Nanotechnology, 2008;3:139-143.
Domenech et al., Lysosomal Membrane Permeabilization by Targeted Magnetic Nanoparticles in Alternating Magnetic Fields, ACS Nano, 2013;7(6):5091-5101.
El-Dakdouki et al., Development of Multifunctional Hyaluronan-Coated Nanoparticles for Imaging and Drug Delivery to Cancer Cells, Biomacromolecules, 2012;13:1144-1151.
Eto et al., Glucose metabolism and glutamate analog acutely alkalinize pH of insulin secretory vesicles of pancreatic beta-cells, Am. J. Physiol. Endocrinol. Metab., 2003;285:E262-E271.
Gaster et al., Matrix-insensitive protein assays push the limits of biosensors in medicine, Nature Medicine, 2009;15(11):1327-1332.
Ghosh et al., M13-templated magnetic nanoparticles for targeted in vivo imaging of prostate cancer, Nat. Nanotechnol., 2012;7(10):677-682.
Grimm et al., Cell Tracking. Principles and Applications. Radiologe, 2007;47:25-33.
Grüttner et al., Synthesis and antibody conjugation of magnetic nanoparticles with improved specific power absorption rates for alternating magnetic field cancer therapy, Journal of Magnetism and Magnetic Materials, 2007;311:181-186.
Guo et al., Multifunctional superparamagnetic nanocarriers with folate-mediated and pH-responsive targeting properties for anticancer drug delivery, Biomaterials, 2011;32:185-194.
Gupta et al., Cytotoxicity suppression and cellular uptake enhancement of surface modified magnetic nanoparticles, Biomaterials, 2005;26,:1565-1573.
Haun et al., Magnetic nanoparticle biosensors, Wiley Interdiscip Rev Nanomed Nanobiotechnol, 2010;2:291-304.
Haun et al., Micro-NMR for Rapid Molecular Analysis of Human Tumor Samples, Science Translation Medicine, 2011;3(71):1-13 with 2 additional pages of Editor's Summary.
Haun et al., Probing Intracellular Biomarkers and Mediators of Cell Activation Using Nanosensors and Bioorthogonal, ACS Nano, 2011;5(4):3204-3213.
Hofmann-Amtenbrink et al., Superparamagnetic nanoparticles for biomedical applications, in Nanostructured Materials for Biomedical Applications. 2009:119-49.
Huang et al., Remote control of ion channels and neurons through magnetic-field heating of nanoparticles, Nature Nanotechnology, 2010;5:602-606.
Ivkov et al., Application of High Amplitude Alternating Magnetic Fields for Heat Induction of Nanoparticles Localized in Cancer, Clin Cancer Res, 2005;11(19 Suppl):7093s-7103s.
Kircher et al., Molecular Body Imaging: MR Imaging, CT, and US. Part II. Applications, Radiology, 2012;264(2):349-368.
Kircher et al., A Multimodal Nanoparticle for Preoperative Magnetic Resonance Imaging and Intraoperative Optical Brain Tumor Delineation. Cancer Research, 2003;63:8122-8125.
Kornhuber et al., Lipophilic Cationic Drugs Increase the Permeability of Lysosomal Membranes in a Cell Culture System, Journal of Cellular Physiology, 2010;224:152-164.
Kozissnik et al., Magnetic fluid hyperthermia: Advances, challenges, and opportunity, International Journal of Hyperthermia, 2013;29(8):706-714.
Kumar et al., Magnetic nanomaterials for hyperthermia-based therapy and controlled drug delivery, Advanced Drug Delivery Reviews, 2011;63:789-808.
Laurent et al., Magnetic fluid hyperthermia: Focus on superparamagnetic iron oxide nanoparticles, Advances in Colloid Interface Science, 2011;166:8-23.
Lee et al., Exchange-coupled magnetic nanoparticles for efficient heat induction, Nature Nanotechnology, 2011;6:418-422.
Mannix et al., Nanomagnetic actuation of receptor-mediated signal transduction, Nature Nanotechnology, 2008;3:36-40.
Martin et al., Synthesis of bombesin-functionalized iron oxide nanoparticles and their specific uptake in prostate cancer cells, J. Nanopart. Res., 2010;12:1599-1608.
Popp et al., Raman meets Medicine—Raman spectroscopy: a powerful tool in Biophotonics. Proc. of the SPIE. 2009;7503. 6 pages. doi: 10.1117/12.837623.
Schulze et al., Uptake and Biocompatibility of Functionalized Poly(vinylalcohol) Coated Superparamagnetic Maghemite Nanoparticles by Synoviocytes InVitro, Journal of Nanoscience and Nanotechnology, 2006;6:2829-2840.
Shona et al., Raman Imaging, Annu. Rev. Anal. Chem. 2012;5:337-360.
Therasse et. al., New guidelines to evaluate the response to treatment in solid tumors, J. Natl. Cancer Inst., 2000;92(3):205-216.
Tomasini et al., Molecular dynamics simulations of rupture in lipid bilayers, Experimental Biology Medicine, 2010;235:181-188.
Tseng et al., Magnetic nanoparticle-mediated massively parallel mechanical modulation of single-cell behavior, Nature Methods, 2012;9(11):1113-19.

(56) References Cited

OTHER PUBLICATIONS

Vikman et al., Insulin secretion is highly sensitive to desorption of plasma membrane cholesterol, The FASEB Journal, 2009;23(1):58-67.

Wahajuddin et al., Superparamagnetic iron oxide nanoparticles: magnetic nanoplatforms as drug carriers. Int. J. of Nanomedicine. 2012;7:3445-71.

Wust et al., Hyperthermia in combined treatment of cancer, The Lancet Oncology, 2002;3:487-497.

Xu et al., Differential Internalization of Superparamagnetic Iron Oxide Nanoparticles in Different Types of Cells, J. Nanoscience Nanotechnology, 2010;10:7406-7410.

Zhang et al. Alternating Magnetic Fields Trigger Apoptosis by Destruction of Lysosomes with LAMP1-Targeted Nanoparticles. Biophysical Journal. 2011;100(3):472.

Zhang et al., Dynamic magnetic fields remote-control apoptosis via nanoparticle rotation. ACS Nano. 2014;8(4):3192-201.

\* cited by examiner

Before Labeling

After Labeling

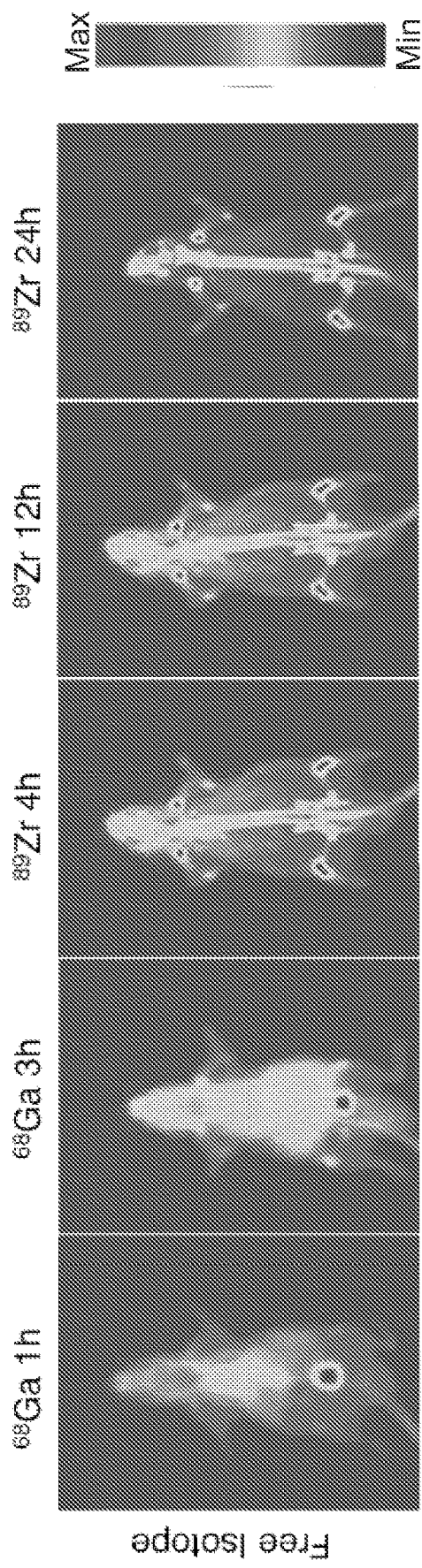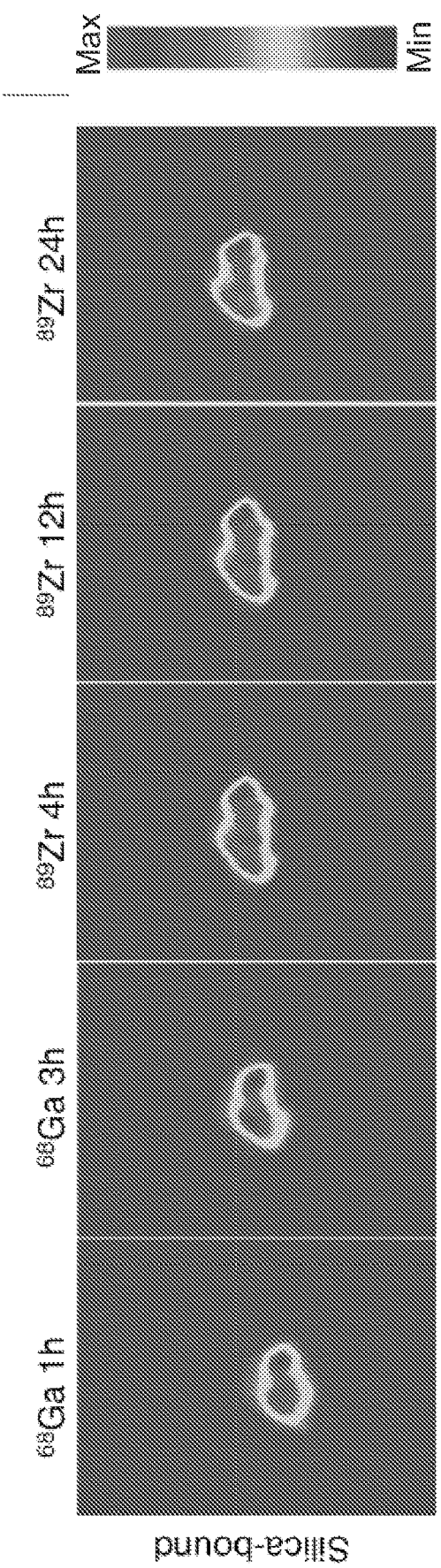
FIG. 6A
FIG. 6B

A   Pre-Operative Planning

METAL(LOID) CHALCOGEN NANOPARTICLES AS UNIVERSAL BINDERS FOR MEDICAL ISOTOPES

CROSS-REFERENCE TO RELATED APPLICATIONS

This application is a U.S. National Stage Application filed under 35 U.S.C. § 371 based on International Application No. PCT/US2015/042441, filed Jul. 28, 2015, which claims priority to and the benefit of, U.S. Provisional Patent Application No. 62/030,005, filed Jul. 28, 2014, the entire contents of each of which are incorporated herein by reference.

GOVERNMENT SUPPORT

This invention was made with government support under K08 CA163961 and R01 EB014944-01 awarded by the National Institutes of Health. The government has certain rights in the invention.

BACKGROUND

A wide variety of medical isotopes find use in medical imaging and/or therapeutic applications. There is a continuing need for the development of improved technologies for utilizing such agents. There is a particular need for the development of technologies that facilitate effective use of radio- or therapeutic medical isotopes, for example, radiolabeled nanoparticles.

Traditional approaches to nanoparticle radiolabeling have typically been customized for particular radioisotopes and have achieved radiolabeling of nanoparticles via surface functionalization of small molecular chelating agents that bind specific radioisotopes. Such traditional approaches enable utilization of labeling protocols that have already been established in molecular chelator research, but present several disadvantages. Since the coordination chemistry of different isotopes varies greatly, there is no molecular chelator that can effectively bind many radioisotopes interchangeably. Thus, for a given radiotracer, selection of and particle modification with the proper chelator may be very difficult or even impossible. Even when isotopes are stably chelated during radiolabeling, introduction of the nanoparticle in vivo presents a new set of challenges. Transchelation by endogenous proteins or detachment of the surface-bound molecular chelators can strip the nanoparticles of their radiolabels, yielding images that do not reflect the true biodistribution. Traditional approaches, among other problems, remain restricted to specific isotopes, rather than being general platforms for many species.

SUMMARY

The present invention provides broadly useful technologies applicable to medical isotopes and their use in a variety of contexts. Among other things, the present invention identifies the source of a problem in traditional approaches to utilizing such medical isotopes, including appreciating that one major hurdle to widespread research and use of these medical isotopes has been the need to design specific binders (e.g., chelators) that would work with each particular medical isotope. The present disclosure appreciates the desirability of technologies that do not require chelators in the productions and/or use of labeled nanoparticles. For example, nanoparticle compositions that are free (or substantially free) of chelators are highly desirable for various whole-body imaging and therapeutic applications. Radiolabeled nanoparticles are of great interest to nuclear imaging and nanooncology communities. Conventional molecular chelators suffer from specificity issues, insofar as there is no nanoparticle substrate that has proven effective in binding a wide variety of radioisotopes.

The present invention provides the insight that certain metal(loid) chalcogen nanoparticle systems are uniquely adaptable for facile use with a wide variety of medical isotopes. The present invention provides, in some embodiments, nanoparticles (e.g., amorphous silica nanoparticles) that can be used as general substrates for radiolabeling that does not require chelators (e.g., "chelator-free" radiolabeling). In some embodiments, nanoparticles are capable of intrinsically binding a wide variety of radioisotopes without additional selective chelation molecules. Some teachings included herein demonstrate an ability of the disclosed nanoparticles (e.g., amorphous silica nanoparticles), to bind multiple medically relevant isotopes of various oxidation states with high radiochemical yield. In some embodiments, nanoparticles can be radiolabeled for multiple applications without being individually modified with different chelators each time.

Further, nanoparticles described herein (e.g., intrinsically labeled silica nanoparticles) demonstrate excellent in vivo stability and efficacy in lymph node tracking.

Moreover, the present invention provides particular technologies for coupling (e.g., via covalent or non-covalent (e.g., chelate) bonds) such metal(loid) chalcogen nanoparticles to medical isotopes without the need for medical isotope-specific chelating agents, and demonstrates their broad applicability. In some embodiments, provided systems and/or methodologies are simple, efficient, effective, rapid, and/or inexpensive. Moreover, teachings included herein provide a general platform strategy that embodies the recognition that the same metal(loid) chalcogen nanoparticles can effectively bind a range of medical isotopes, and moreover that only simple processing steps are required to achieve such binding.

In a broad sense, the present invention identifies the source of a variety of problems arising from traditional chelation approaches to utilizing medical isotopes, which approaches typically focus on individualized, non-trivial design of molecular chelating agents specifically tailored to a particular medical isotope. Among other things, the present invention recognizes that such approaches typically require the medical isotope to fit into a particular (small) molecular "cage" of a distinct size (depending on the ionic radius of the specific medical isotope used), and thereby dramatically limit the type of medical isotopes that can be utilized with any given chelator.

Moreover, the present invention identifies the source of a problem with certain traditional medical isotope chelation systems in that they require separate chelation and targeting components, as traditional chelators (particularly, small molecule chelators) do not naturally accumulate in cancer and/or suffer from rapid washout from sites of interest in vivo.

The present invention, by contrast, provides platform technologies for binding (e.g., covalent- or non-covalent (e.g., chelation) interaction, stable sequestering, etc.) a wide variety of different medical isotopes (e.g., (radioactive) metals, semi-metals, and non-metal atoms or ions) such that they can be used in vivo. Among other things, the present invention identifies useful metal(loid) chalcogen nanoparticles that can bind (e.g., covalent- or non-covalent (e.g., chelation) interaction, sequester, etc.) any of a variety of different medical isotopes, provides simple methodologies for achieving such binding (e.g., via covalent- or non-covalent (e.g., chelation) interaction, sequestration, etc.), provides simple methodologies for achieving purification of bound complexes, and also provides reagents, kits, methods, and uses thereof.

In some embodiments, the present invention provides a platform for binding (e.g., via covalent- or non-covalent (e.g., chelation) interaction, sequestration, etc.) a wide library of medical isotopes, such that the medical isotope labeled metal(loid) chalcogen nanoparticles stably accumulate and remain in desired treatment or imaging site(s) within a patient's body.

In some embodiments, the present invention provides medical isotope labeled metal(loid) chalcogen nanoparticles prepared according to methodologies described herein. In some embodiments, the present invention provides medical isotope labeled metal(loid) chalcogen nanoparticles that are prepared without use of traditional chelating agents. In some embodiments, the present invention provides modular kits for facile production of whole-body imaging or therapeutic agents that home to cancer with or without targeting. In some embodiments, metal(loid) chalcogen nanoparticles are used as universal binders that stably incorporate radioactive and/or other medical imaging and/or therapeutic isotopes, covalently or non-covalently (for example, but not limited to, via chelate bonds) binding the isotopes inside of a dense alternating metal(loid) chalcogen network (e.g., -oxygen-silicon-oxygen-silicon-, or sulfur-zinc-sulfur-zinc-, etc.) within the metal(loid) chalcogen nanoparticle.

In some embodiments, the present invention relates to using metal(loid) chalcogen nanoparticles (comprising, e.g., silica, titania, zinc sulfide, etc.) having a longest dimension between 2-1000 nm as universal binders (e.g., via covalent bonds, non-covalent (e.g., chelate) bonds, etc.) for medical isotopes (e.g., PET-active radioisotopes, SPECT-active radioisotopes, MRI-active materials; and therapeutic radioisotopes, etc.).

In some embodiments, the present invention relates to using metal(loid) chalcogen microparticles (comprising, e.g., silica, titania, zinc sulfide, etc.) having a longest dimension between 1 μm-100 μm as universal binders (e.g., via covalent bonds, non-covalent (e.g., chelate) bonds, etc.) for medical isotopes (e.g., PET-active radioisotopes, SPECT-active radioisotopes, MRI-active materials; and therapeutic radioisotopes, etc. In some embodiments, medical isotope labeled metal(loid) chalcogen microparticles are particularly useful for oral administration to patients.

Traditionally, these medical isotopes needed to be chelated by a traditional small molecular chelating agent (e.g. DTPA, DOTA, NOTA, DFO, etc.). However, since each medical isotope typically has a different atomic and/or ionic radius, different chelating agents were previously thought to be required for each different medical isotope. Furthermore, the chelated medical isotopes traditionally had to be purified from free medical isotopes by chromatography (e.g. liquid chromatography (LC), or size-exclusion chromatography (SEC), etc.).

The present invention provides methods, kits, and systems for quickly (e.g., within a time period equal to or greater than 5 minutes, e.g., 5 minutes, 30 minutes, 60 minutes, 5-60 minutes, etc.) and directly (i.e., without the use of any additional small molecular chelator) binding of the medical isotope to the metal(loid) chalcogen nanoparticles (e.g., silica nanoparticles) or metal(loid) chalcogen microparticles by heating the medical isotope/metal(loid) chalcogen nanoparticle dispersion to a temperature of at or above 25° C. (e.g., 30° C., 40° C., 50° C., 60° C., 70° C., above 70° C., etc.) and then separating (e.g., by centrifuging, filtration, or other suitable separation method) the medical isotope labeled metal(loid) chalcogen nanoparticles (or microparticles) from the unbound/free medical isotope. In some embodiments, the pelleted labeled metal(loid) chalcogen nanoparticles (or microparticles) can then be redispersed in infusion fluid and can immediately be used for (pre) clinical applications (e.g., intravenous injection, subcutaneous injection, medical imaging, and/or therapy, etc.).

Medical isotope labeled metal(loid) chalcogen nanoparticle and microparticle compositions as described herein may be used in any appropriate application. Those of ordinary skill in the art, reading the present specification, will appreciate that certain provided compositions are particularly useful in certain contexts. To give but one example, in some embodiments, medical isotope labeled metal(loid) chalcogen nanoparticle and microparticle compositions may be particularly appropriate for use with clinical and preclinical applications, for medical and biomedical imaging technologies (including PET, MRI, PET/MRI, SPECT, SPECT/CT, Cerenkov Luminescence Imaging (CLI), secondary Cerenkov-induced Fluorescence Imaging (SCIFI), etc.), and for treatment of diseases, including various cancers.

In one aspect, the present invention relates to a method of preparing medical isotope labeled metal(loid) chalcogen nanoparticles. The method includes the steps of: (1) providing a reaction mixture comprising or consisting of: (i) metal(loid) chalcogen nanoparticles (e.g., metal chalcogen nanoparticles (e.g., zinc sulfide), metalloid chalcogen nanoparticles (e.g., silica), metalloid chalcogen-coated metal nanoparticles (e.g., silica-coated gold nanoparticles)); and (ii) medical isotopes (e.g., PET-active radioisotopes (e.g., Gallium-66, Gallium-68, Zirconium-89, Copper-64), SPECT-active radioisotopes (e.g., Technetium-99m, Indium-111), MRI-active metals (e.g., Gadolinium, Manganese), therapeutic radioisotopes (e.g., Bismuth-213, Actinium-225, Boron-10)) and (2) maintaining the reaction mixture under conditions and for a time sufficient for the medical isotopes to bind with and thereby label the metal (loid) chalcogen nanoparticles.

In some embodiments, binding is accomplished via covalent bonds. In some embodiments, binding is accomplished via non-covalent bonds. In some embodiments, non-covalent bonds are chelate bonds.

In some embodiments, the method of preparing medical isotope labeled metal(loid) chalcogen nanoparticles also includes a step of isolating the medical isotope labeled metal(loid) chalcogen nanoparticles. In some embodiments, step of isolating the medical isotope labeled metal(loid) chalcogen nanoparticles includes centrifuging the reaction mixture. In some embodiments, step of isolating the medical isotope labeled metal(loid) chalcogen nanoparticles includes filtrating the reaction mixture. In some embodiments, step of isolating the medical isotope labeled metal(loid) chalcogen nanoparticles includes filtrating the reaction mixture. In some embodiments, the method of preparing medical isotope labeled metal(loid) chalcogen nanoparticles also includes dispersing (e.g., by sonication) the isolated medical isotope labeled metal(loid) chalcogen nanoparticles in an infusion fluid.

In some embodiments, the conditions sufficient for the medical isotopes to bind with and thereby label the metal (loid) chalcogen nanoparticles include heating the reaction mixture to a temperature of equal to or greater than 25° C. In some embodiments, the conditions sufficient for the medical isotopes to bind with and thereby label the metal (loid) chalcogen nanoparticles include heating the reaction mixture to a temperature of between 45° C. and 80° C., e.g., around 70° C. In some embodiments, the conditions sufficient for the medical isotopes to bind with and thereby label the metal(loid) chalcogen nanoparticles include heating the reaction mixture to a temperature of equal to or greater than 95° C. In some embodiments, the time sufficient for the medical isotopes to bind with and thereby label the metal(loid) chalcogen nanoparticles is between 5-30 minutes, between 5-60 minutes, between 60-120 minutes, or between 5-120 minutes.

In some embodiments, the method of preparing medical isotope labeled metal(loid) chalcogen nanoparticles also includes administering the medical isotope labeled metal(loid) chalcogen nanoparticles to a subject in vivo.

In some embodiments, the integrity of the medical isotope labeled metal(loid) chalcogen nanoparticles is not affected by the labeling procedure.

In some embodiments, the metal(loid) chalcogen nanoparticles are doped with a fluorescent agent. In some embodiments, the metal(loid) chalcogen nanoparticles are doped with a metal. In some embodiments, the metal(loid) chalcogen nanoparticles are doped with a semi-metal. In some embodiments, the metal(loid) chalcogen nanoparticles are doped with a non-metal. In some embodiments, the metal(loid) chalcogen nanoparticles are doped with a combination of at least two materials selected from the list comprising a fluorescent agent, a metal, a semi-metal, and a non-metal.

In a further aspect, the present invention relates to a kit for production of medical isotope labeled metal(loid) chalcogen nanoparticle agents for imaging or therapeutics. The kit includes metal(loid) chalcogen nanoparticles (e.g., metal chalcogen nanoparticles (e.g., zinc sulfide), metalloid nanoparticles (e.g., silica), metalloid chalcogen-coated metal nanoparticles (e.g., silica-coated gold nanoparticles)). Metal(loid) chalcogen nanoparticles are characterized in that, when exposed to an elevated temperature (e.g., equal to or greater than 25° C.), they bind (e.g., form covalent or non-covalent bonds with) any of a plurality of different medical isotopes.

In some embodiments, the kit further includes reagents for combining the metal(loid) chalcogen nanoparticles with any of the plurality of different medical isotopes. In some embodiments, the kit further includes a buffer. In some embodiments, the kit further includes an infusion fluid. In some embodiments, the kit further includes a device for administering the medical isotope labeled metal(loid) chalcogen nanoparticle agent to a subject. In some embodiments, the device for administering the medical isotope labeled metal(loid) chalcogen nanoparticle agent to a subject is a syringe.

In some embodiments, the metal(loid) chalcogen nanoparticles are or comprise silica.

In some embodiments, the metal(loid) chalcogen nanoparticles have a longest dimension between 2-1000 nm.

In some embodiments, the medical isotopes are or comprise PET-active radioisotopes. In some embodiments, PET-active radioisotopes are or comprise gallium-66, gallium-58, zirconium-89, and copper-64. In some embodiments, the medical isotopes are or comprise SPECT-active radioisotopes. In some embodiments, SPECT-active radioisotopes are or comprise technetium-99m, indium-111. In some embodiments, the medical isotopes are or comprise MRI-active metals. In some embodiments, MRI-active metals are or include gadolinium or manganese salts. In some embodiments, the medical isotopes are or comprise therapeutic radioisotopes. In some embodiments, therapeutic radioisotopes are or comprise bismuth-213 or actinium-225.

In some embodiments, the metal(loid) chalcogen nanoparticles provided in the kit are doped with a fluorescent agent. In some embodiments, the metal(loid) chalcogen nanoparticles provided in the kit are doped with a metal. In some embodiments, the metal(loid) chalcogen nanoparticles provided in the kit are doped with a semi-metal. In some embodiments, the metal(loid) chalcogen nanoparticles provided in the kit are doped with a non-metal. In some embodiments, the metal(loid) chalcogen nanoparticles provided in the kit are doped with a combination of at least two materials selected from the list comprising a fluorescent agent, a metal, a semi-metal, and a non-metal.

In some embodiments, the metal(loid) chalcogen nanoparticles have a porosity between 0.2-2 nm (microporous). In some embodiments, the metal(loid) chalcogen nanoparticles have a porosity between 2-50 nm (mesoporous). In some embodiments, the metal(loid) chalcogen nanoparticles have a porosity between 50-1000 nm (macroporous). In some embodiments, the metal(loid) chalcogen nanoparticles are biodegradable.

In a further aspect, the present invention relates to a medical isotope labeled metal(loid) chalcogen nanoparticle agent. The medical isotope labeled metal(loid) chalcogen nanoparticle agent includes a metal(loid) chalcogen nanoparticle (e.g., metal chalcogen nanoparticles (e.g., zinc sulfide), metal(loid) chalcogen nanoparticles (e.g., silica), metalloid chalcogen-coated metal nanoparticle (e.g., silica-coated gold nanoparticles)) bound to a medical isotope (e.g., via covalent or non-covalent bonds) and having a porosity between 0.2-2 nm. The medical isotope labeled metal(loid) chalcogen nanoparticle agent is characterized in that the medical isotope labeled metal(loid) chalcogen nanoparticle agent is stable in vivo for at least 3 hours.

In some embodiments, the metal(loid) chalcogen nanoparticle is or includes silica. In some embodiments, the medical isotope labeled metal(loid) chalcogen nanoparticle agent is characterized in that it localizes in a desired site, e.g., liver, spleen, tumor, lymph node, inflammation, or, infections. In some embodiments, the medical isotope labeled metal(loid) chalcogen nanoparticle agent is biodegradable.

The medical isotope labeled metal(loid) chalcogen nanoparticle agent is characterized in that the medical isotope labeled metal(loid) chalcogen nanoparticle agent is stable in vivo for at least 6 hours, at least 8 hours, at least 12 hours, or at least 24 hours.

In some embodiments, the metal(loid) chalcogen nanoparticle is doped with a fluorophore. In some embodiments, the metal(loid) chalcogen nanoparticle is doped with a metal. In some embodiments, the metal(loid) chalcogen nanoparticle is doped with a semi-metal. In some embodiments, the metal(loid) chalcogen nanoparticle is doped with a non-metal. In some embodiments, the metal(loid) chalcogen nanoparticle is doped with at least two materials selected from the list comprising fluorescence agent, metal, semi-metal, and non-metal.

In some embodiments, the medical isotope labeled metal(loid) chalcogen nanoparticle includes at least one targeting moiety/agent. In some embodiments, the targeting moiety/agent includes at least one agent selected from the list including antibodies, peptides, aptamers, small molecules, and any combination thereof.

In some embodiments, the medical isotope labeled metal(loid) chalcogen nanoparticle comprises at least one click reagent. In some embodiments, the click reagent includes at least one agent selected from the list including, but not limited to, alkynes, azides, cyclooctynes (e.g., (sulfo-)dibenzocyclooctynes, (1R,8S,9s)-Bicyclo[6.1.0]non-4-yn-9-yls (BCN), (E)-Cyclooctynes, TCO, etc.), isonitriles, ketones, nitrones, oximes, quadricyclanes, and tetrazines.

In some embodiments, the metal(loid) chalcogen nanoparticle is bound to the medical isotope via covalent bonds. In some embodiments, the metal(loid) chalcogen nanoparticle is bound to the medical isotope via non-covalent bonds. In some embodiments, the metal(loid) chalcogen nanoparticle is bound to the medical isotope via chelate bonds.

In some embodiments, the medical isotope labeled metal(loid) chalcogen nanoparticle is used for preclinical research. In some embodiments, the medical isotope labeled metal(loid) chalcogen nanoparticle is used for biomedical imaging. In some embodiments, the medical isotope labeled metal(loid) chalcogen nanoparticle is used for therapy (e.g., of cancer). In some embodiments, the medical isotope labeled metal(loid) chalcogen nanoparticle is used for intraoperative imaging. In some embodiments, the medical isotope labeled metal(loid) chalcogen nanoparticle is used for surgery preparation and/or planning.

In a further aspect, the present invention relates to a medical isotope labeled chalcogen metal(loid) microparticle agent. The medical isotope labeled chalcogen metal(loid) microparticle agent includes a metal(loid) chalcogen microparticle (e.g., metal chalcogen microparticle (e.g., zinc sulfide), metal(loid) chalcogen microparticle (e.g., silica), metal(loid) chalcogen-coated metal microparticle (e.g., silica-coated gold microparticles)) having a porosity between 0.2-2 nm, 2-50 nm, or between 50-1000 nm bound to a medical isotope (e.g., via covalent or non-covalent (e.g., chelate) bonds), characterized in that the medical isotope labeled microparticle agent is stable in vivo for at least 3 hours.

In some embodiments, the chalcogen metal(loid) microparticle has a longest dimension between 1 μm and 100 μm.

In a further aspect, the present invention relates to a method of conducting a bioorthogonal click reaction. Bioorthogonal click reaction may include the steps of (1) administering (e.g., injecting) a targeting moiety (e.g., antibody peptide, etc.) conjugated to a first click reagent (e.g., cyclooctyne) to a subject; and (2) administering (e.g., injecting, e.g., a sufficient time to allow the targeting moiety to home and bind to its target) to the subject a medical isotope labeled chalcogen metal(loid) nanoparticle agent. The medical isotope labeled chalcogen metal(loid) nanoparticle agent includes a metal(loid) chalcogen nanoparticle (e.g., silica nanoparticle, zirconia nanoparticle, titania nanoparticle, silica coated metal nanoparticle) bound to a medical isotope (e.g., via covalent or non-covalent (e.g., chelate) bonds), characterized in that the medical isotope labeled chalcogen metal(loid) nanoparticle agent is stable in vivo for at least 3 hours, wherein the medical isotope labeled metal(loid) chalcogen nanoparticle agent includes at least one second click reagent (e.g., azide) for selective binding to the first click reagent.

Without wishing to be bound to any particular theory, click chemistry describes pairs of functional groups ("click reagents") that rapidly and selectively react ("click") with each other under mild, aqueous conditions. Click Chemistry is a bioorthogonal two-step coupling procedure that is widely used in life sciences, drug discovery and biomedical imaging.

In some embodiments, click reagents include, but are not limited to, alkynes, azides, cyclooctynes (e.g. (sulfo-)dibenzocyclooctynes, (1R,8S,9s)-Bicyclo[6.1.0]non-4-yn-9-yls (BCN), (E)-Cyclooctynes, TCO, etc.), isonitriles, ketones, nitrones, oximes, quadricyclanes, tetrazines, etc.

In a further aspect, the present invention relates to a method of preparing medical isotope labeled metal(loid) chalcogen nanoparticles, the method including steps of: providing a reaction mixture comprising or consisting of: metal(loid) chalcogen nanoparticles (e.g., metal chalcogen nanoparticles (e.g., zinc chalcogen), metalloid chalcogen nanoparticles (e.g., silica), metal(loid) chalcogen-coated metal nanoparticles (e.g., silica-coated gold nanoparticles)) comprising at least one surface-enhanced (resonance) Raman scattering (SE(R)RS) active agent; and a medical isotope (e.g., PET-active radioisotopes (e.g., gallium-66, gallium-68, zirconium-89, copper-64, etc.), SPECT-active radioisotopes (e.g., technetium-99m, indium-111, etc.), MRI-active metals (e.g., gadolinium, manganese), therapeutic radioisotopes (e.g., bismuth-213, actinium-225, etc.)); and maintaining the reaction mixture under conditions and for a time sufficient for the medical isotopes to bind (e.g., covalently or non-covalently) with and thereby label the metal(loid) chalcogen nanoparticles.

In some embodiments, the method includes a step of administering to a subject (e.g., a human subject) a collection of medical isotope labeled metal(loid) chalcogen nanoparticles prepared by the methods described herein.

In another aspect, the present invention relates to a kit for production of a medical isotope labeled metal(loid) chalcogen nanoparticle agent for imaging or therapeutics, including: metal(loid) chalcogen nanoparticles (e.g., metal chalcogen nanoparticles (e.g., zinc chalcogen), metalloid chalcogen nanoparticles (e.g., silica), metal(loid) chalcogen-coated metal nanoparticles (e.g., silica-coated gold nanoparticles)) comprising at least one surface-enhanced (resonance) Raman scattering (SE(R)RS) active agent, wherein the metal(loid) chalcogen nanoparticles are characterized in that, when exposed to an elevated temperature (e.g., equal to or greater than 25° C.), they bind (e.g., form covalent or non-covalent bonds with) any of a plurality of different medical isotopes.

In a further aspect, the present invention relates to a medical isotope labeled chalcogen metal(loid) nanoparticle, including: a metal(loid) chalcogen nanoparticle (e.g., metal chalcogen nanoparticle (e.g., zinc sulfide), metal(loid) chalcogen nanoparticle (e.g., silica), metal(loid) chalcogen-coated metal nanoparticle (e.g., silica-coated gold nanoparticles)) having a porosity between 0.2-2 nm bound to a medical isotope (e.g., via covalent or non-covalent bonds), wherein the metal(loid) chalcogen nanoparticle comprises at least one surface-enhanced (resonance) Raman scattering (SE(R)RS) active agent (e.g., distributed at a location selected from the group consisting of: on or within nanoparticle core, on or between capping agent entities, on or within an encapsulant layer, and combinations thereof), the metal(loid) chalcogen nanoparticle being characterized in that the medical isotope labeled nanoparticle is stable in vivo for at least 3 hours.

In some embodiments, medical isotope labeled chalcogen metal(loid) nanoparticles described herein have an affinity to bind a variety of different medical isotopes selected from the group consisting of: PET-active radioisotopes (e.g., gallium-66, gallium-68, zirconium-89, copper-64, etc.), SPECT-active radioisotopes (e.g., technetium-99m, indium-111, etc.), MRI-active metals (e.g., gadolinium, manganese), and therapeutic radioisotopes (e.g., bismuth-213, actinium-225, etc.).

In another aspect, the present invention relates to a method that includes a step of administering to a subject a medical isotope labeled metal(loid) chalcogen nanoparticle (or a collection thereof) described herein. In some embodiments, the step of administering includes administering to a location the medical isotope labeled chalcogen metal(loid) nanoparticle to localize to the solid tumor. In some embodiments, the method includes imaging the localized medical isotope labeled chalcogen metal(loid) nanoparticle agent.

Elements of embodiments described with respect to a given aspect of the invention may be used in various embodiments of another aspect of the invention. For example, it is contemplated that features of dependent claims depending from one independent claim can be used in apparatus and/or methods of any of the other independent claims.

Definitions

In order for the present disclosure to be more readily understood, certain terms are defined below. Additional definitions for, or clarifications of, the following terms and other terms may be set forth throughout the specification.

In this application, the use of "or" means "and/or" unless stated otherwise. As used in this application, the term "comprise" and variations of the term, such as "comprising" and "comprises," are used in situations where listed items, elements, or steps are included and others may also be included. As used in this application, the terms "about" and "approximately" are used as equivalents. Any numerals used in this application, whether or not preceded by "about" or "approximately" are meant unless otherwise indicated to cover any normal fluctuations (e.g., standard errors or deviations), as would be appreciated by one of ordinary skill in the relevant art. In certain embodiments, the terms "approximately" or "about" refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Administration: As used herein, the term "administration" refers to the administration of a composition to a subject. Administration may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal, and vitreal.

Associated with: Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility of the disease, disorder, or condition (e.g., across a relevant population). In some embodiments, two or more entities are physically "associated" with one another if they interact, directly or indirectly, so that they are and remain in physical proximity with one another. In some embodiments, two or more entities that are physically associated with one another are bound to one another.

Biocompatible: The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, biocompatible materials are biodegradable, e.g., into biocompatible components.

Biodegradable: As used herein, "biodegradable" materials are those that, when introduced into cells, are broken down by cellular machinery (e.g., enzymatic degradation) or by hydrolysis into components that cells can either reuse or dispose of without significant toxic effects on the cells. In certain embodiments, components generated by breakdown of a biodegradable material do not induce inflammation and/or other adverse effects in vivo. In some embodiments, biodegradable materials are enzymatically broken down. Alternatively or additionally, in some embodiments, biodegradable materials are broken down by hydrolysis. In some embodiments, biodegradable polymeric materials break down into their component polymers. In some embodiments, breakdown of biodegradable materials (including, for example, biodegradable polymeric materials) includes hydrolysis of ester bonds. In some embodiments, breakdown of materials (including, for example, biodegradable polymeric materials) includes cleavage of urethane linkages.

Bound: as used herein, the term "bound" is intended to describe two or more entities that are physically associated with one another by covalent or non-covalent interaction. In some embodiments, two or more entities are determined to be physically associated with one another when the presence of one correlates with the presence of the other. In some embodiments, two or more entities are determined to be physically associated with one another when the ratio reflecting their relative amounts in a given location is stable over time. In some embodiments, non-covalent interactions are or include chelate bonds, hydrogen bonds, van der Waals interactions, hydrophobic interactions, magnetic interactions, electrostatic interactions, etc., and combinations thereof.

Chalcogen: as used herein, the term "chalcogen" refers to the chemical elements in group 16 of the periodic table. These elements include oxygen, sulfur, selenium, tellurium, and polonium.

Comparable: The term "comparable", as used herein, refers to two or more agents, entities, situations, sets of conditions, etc. that may not be identical to one another but that are sufficiently similar to permit comparison therebetween so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

Illuminating: The term "illuminating" as used herein refers to application of a light source such as, for example, a near-infrared (NIR), visible, or ultraviolet (UV) light source. In some embodiments, illuminating comprises applying laser light. In some embodiments, illuminating comprises applying light of a wavelength appropriate to excite one or more responsive agents; in some such embodiments, responsive agents are comprised in provided particles. For example, one or more dopant entities, layers, and/or substrates may be or comprise a light-responsive agent.

Labeled Metal(loid) Chalcogen Nanoparticle: as used herein, the term "labeled metal(loid) chalcogen nanoparticle" refers to a metal(loid) chalcogen nanoparticle bound (e.g., via covalent or non-covalent (e.g., chelate) bonds) to a medical isotope as described herein. Without wishing to be bound by any particular theory, we propose that practice of the present invention traps medical isotopes within nanoparticles, for example through multivalent interaction with electron donor moieties (e.g., oxygens, sulfurs) within the metal(loid) chalcogen nanoparticle. According to this hypothesis, such medical isotopes are fairly characterized as being bound (e.g., via covalent or non-covalent (e.g., chelate) bonding) by an electron-donor (e.g., oxygen, sulfur) network within the metal(loid) chalcogen nanoparticles. In some embodiments, labeling of metal(loid) chalcogen nanoparticles occurs via non-covalent binding. In some embodiments, non-covalent bonding between the medical isotope and the metal(loid) chalcogen nanoparticles is chelate bonding, accomplished without use of traditional chelating agents. In some embodiments, labeling of metal(loid) chalcogen nanoparticles occurs via formation of covalent bonds between the medical isotope and the metal(loid) chalcogen nanoparticles. In some embodiments, a composition that is or comprises a labeled metal(loid) chalcogen nanoparticle is referred to herein as a "labeled metal(loid) chalcogen nanoparticle agent". In some embodiments, such an agent includes only a single species of nanoparticle (typically multiple individual nanoparticles of that species). Alternatively, in some embodiments, a particular agent may be or comprise a plurality of different species of labeled metal(loid) chalcogen nanoparticle.

Magnetic Resonance Imaging: The term "magnetic resonance imaging (MRI)" as used herein refers to a medical imaging technique most commonly used in radiology to visualize the structure and function of the body. It provides detailed images of the body in any plane. MRI uses no ionizing radiation, but uses a powerful magnetic field to align the nuclear magnetization of (usually) hydrogen atoms in water in the body. Radiofrequency fields are used to systematically alter the alignment of this magnetization, causing the hydrogen nuclei to produce a rotating magnetic field detectable by the scanner. This signal can be manipulated by additional magnetic fields to build up enough information to construct an image of the body. When a subject lies in a scanner, the hydrogen nuclei (i.e., protons) found in abundance in an animal body in water molecules, align with the strong main magnetic field. A second electromagnetic field that oscillates at radiofrequencies and is perpendicular to the main field, is then pulsed to push a proportion of the protons out of alignment with the main field. These protons then drift back into alignment with the main field, emitting a detectable radiofrequency signal as they do so. Since protons in different tissues of the body (e.g., fat versus muscle) realign at different speeds, the different structures of the body can be revealed. Contrast agents may be injected intravenously to enhance the appearance of blood vessels, tumors or inflammation. MRI is used to image every part of the body, but is particularly useful in neurological conditions, disorders of the muscles and joints, for evaluating tumors and showing abnormalities in the heart and blood vessels.

Medical Isotope: The term "medical isotope" as used herein refers to a metal, a metal-like, or non-metal isotope appropriate for use in medical contexts, including clinical research and preclinical applications. In some embodiments, a medical isotope is or comprises a stable isotope; in some such embodiments, a medical isotope is or comprises a radioactive isotope. To give but a few examples, in some embodiments, a medical isotope is or comprises one or more of a nuclear medicine imaging agent, a positron-emitter, a negatron emitter, an alpha emitter, a gamma emitter, a PET-active radioisotope (e.g., Gallium-68, Zirconium-89), SPECT-active radioisotope (e.g., Technetium-99m), a MRI-active material (e.g., Gadolinium, Manganese), a neutron capturing isotope (e.g., Boron-10, Gold-197), a therapeutic radioisotope (e.g., Bismuth-213, Actinium-225), etc. In some particular embodiments, a medical isotope is or comprises a positron-emitter selected from the list including, but not limited to, Zirconium-89, Gallium-68, and Copper-64. In some particular embodiments, a medical isotope is or comprises a PET-active radioisotope or a nuclear medicine imaging agent selected from the list including, but not limited to, Copper-64, Gallium-68, and Zirconium-89. In some particular embodiments, a medical isotope is or comprises a SPECT-active radioisotope selected from the list including, but not limited to, Technetium-99m, Indium-111, Thallium-201, Gallium-67, Tin-117m, or Lutetium-177. In some particular embodiments, a medical isotope is or comprises a MRI-active material selected from the list including, but not limited to, Gadolinium, Manganese, Iron, Dysprosium, Holmium, or Erbium. In some particular embodiments, a medical isotope is or comprises a therapeutic (radioactive or non-radioactive) isotope selected from the list including, but not limited to, Actinium-225, Actinium-227, Americium-241, Arsenic-72, Arsenic-74, Astatine-211, Boron-10, Boron-11, Beryllium-7, Bismuth-212, Bismuth-213, Bromine-77, Carbon-11, Carbon-14, Calcium-48, Cadmium-109, Cerium-139, Cerium-141, Californium-252, Cesium-130, Cesium-131, Cesium-137, Chromium-51, Cobalt-55, Cobalt-57, Cobalt-60, Copper-61, Copper-62, Copper-63, Copper-64, Copper-67, Dysprosium-165, Europium-152, Europium-155, Erbium-169, Fluor-18, Gadolinium-153, Gallium-64, Gallium-65, Gallium-67, Gallium-68, Germanium-66, Germanium-68, Germanium-69, Gold-198, Holmium-166, Indium-111, Indium-111m, Iodine-122, Iodine-123, Iodine-124, Iodine-125, Iodine-131, Iodine-132, Iridium-191m, Iridium-192, Iron-55, Iron-59, Krypton-81m, Lead-203, Lead-212, Lutetium-177, Manganese-51, Molybdenum-99 (progenitor to Technetium-99m), Niobium-95, Nitrogen-13, Oxygen-15, Osmium-191, Osmium-194, Palladium-103, Palladium-109, Phosphorus-32, Phosphorus-33, Plutonium-238, Potassium-42, Radium-223, Radium-226, Rhenium-186, Rhenium-188, Rhodium-105, Rubidium-82, Ruthenium-103, Ruthenium-106, Samarium-145, Samarium-153, Scandium-46, Scandium-47, Selenium-72, Selenium-75, Silicon-28, Sodium-24, Strontium-82 (as progenitor of Rubidium-82), Strontium-85, Strontium-89, Strontium-90, Strontium-92, Sulfur-35, Tantalum-178, Tantalum-179, Tantalum-182, Technetium-96, Technetium-99m, Terbium-149, Thallium-201, Thorium-227, Thorium-228, Thorium-229, Thulium-170, Thulium-171, Tin-117m, Tritium, Tungsten-188, Xenon-127, Xenon-133, Ytterbium-169, Ytterbium-177 (as a progenitor of Lu-177), Yttrium-89, Yttrium-90, Yttrium-91, Zinc-65, Zirconium-89, Zirconium-95.

Metal(loid) Chalcogen Nanoparticle: "metal(loid) chalcogen nanoparticle" as used herein refers to a nanoparticle that includes a metal, non-metal, or metal-like component, as discussed further below. In some embodiments, the metal(loid) chalcogen nanoparticle is characterized by a microporous (e.g., with pore size of 0.2-2 nm), mesoporous (e.g., with pore size of 2-50 nm), or macroporous (e.g., with pore size of 50-1000 nm) alternating network of chalcogen (e.g.

oxygen, sulfur) and metal(loid) (e.g. zinc, silicon) atoms. In some embodiments, the metal(loid) chalcogen nanoparticle is amorphous.

Pharmaceutically acceptable: The term "pharmaceutically acceptable" as used herein, refers to agents that, within the scope of sound medical judgment, are suitable for use in contact with tissues of human beings and/or animals without excessive toxicity, irritation, allergic response, or other problem or complication, commensurate with a reasonable benefit/risk ratio.

Reference: The term "reference" is often used herein to describe a standard or control agent or value against which an agent or value of interest is compared. In some embodiments, a reference agent is tested and/or a reference value is determined substantially simultaneously with the testing or determination of the agent or value of interest. In some embodiments, a reference agent or value is a historical reference, optionally embodied in a tangible medium. Typically, as would be understood by those skilled in the art, a reference agent or value is determined or characterized under conditions comparable to those utilized to determine or characterize the agent or value of interest.

Sample: The term "sample" refers to a volume or mass obtained, provided, and/or subjected to analysis. In some embodiments, a sample is or comprises a tissue sample, cell sample, a fluid sample, and the like. In some embodiments, a sample is taken from a subject (e.g., a human or animal subject). In some embodiments, a tissue sample is or comprises brain, hair (including roots), buccal swabs, blood, saliva, semen, muscle, or from any internal organs, or cancer, precancerous, or tumor cells associated with any one of these. A fluid may be, but is not limited to, urine, blood, ascites, pleural fluid, spinal fluid, and the like. A body tissue can include, but is not limited to, brain, skin, muscle, endometrial, uterine, and cervical tissue or cancer, precancerous, or tumor cells associated with any one of these. In an embodiment, a body tissue is brain tissue or a brain tumor or cancer. Those of ordinary skill in the art will appreciate that, in some embodiments, a "sample" is a "primary sample" in that it is obtained from a source (e.g., a subject); in some embodiments, a "sample" is the result of processing of a primary sample, for example to remove certain potentially contaminating components and/or to isolate or purify certain components of interest.

Small molecule: As used herein, the term "small molecule" means a low molecular weight organic compound that may serve as an enzyme substrate or regulator of biological processes. In general, a "small molecule" is a molecule that is less than about 5 kilodaltons (kD) in size. In some embodiments, provided nanoparticles further include one or more small molecules. In some embodiments, the small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, one or more small molecules are encapsulated within the nanoparticle. In some embodiments, small molecules are non-polymeric. In some embodiments, in accordance with the present invention, small molecules are not proteins, polypeptides, oligopeptides, peptides, polynucleotides, oligonucleotides, polysaccharides, glycoproteins, proteoglycans, etc. In some embodiments, a small molecule is a therapeutic. In some embodiments, a small molecule is an adjuvant. In some embodiments, a small molecule is a drug.

Stable: The term "stable," when applied to compositions herein, means that the compositions maintain one or more aspects of their physical structure (e.g., size range and/or distribution of particles) over a period of time. In some embodiments, a stable nanoparticle composition is one for which the average particle size, the maximum particle size, the range of particle sizes, and/or the distribution of particle sizes (i.e., the percentage of particles above a designated size and/or outside a designated range of sizes) is maintained for a period of time under specified conditions. In some embodiments, a stable provided composition is one for which a biologically relevant activity is maintained for a period of time. In some embodiments, the period of time is at least about one hour; in some embodiments the period of time is about 5 hours, about 10 hours, about one (1) day, about one (1) week, about two (2) weeks, about one (1) month, about two (2) months, about three (3) months, about four (4) months, about five (5) months, about six (6) months, about eight (8) months, about ten (10) months, about twelve (12) months, about twenty-four (24) months, about thirty-six (36) months, or longer. In some embodiments, the period of time is within the range of about one (1) day to about twenty-four (24) months, about two (2) weeks to about twelve (12) months, about two (2) months to about five (5) months, etc. For example, if a population of nanoparticles is subjected to prolonged storage, temperature changes, and/or pH changes, and a majority of the nanoparticles in the composition maintain a diameter within a stated range, the nanoparticle composition is stable. In some embodiments, a stable composition is stable at ambient conditions. In some embodiments, a stable composition is stable under biologic conditions (i.e., 37° C. in phosphate buffered saline).

Subject: As used herein, the term "subject" refers to a human or any non-human animal (e.g., mouse, rat, rabbit, dog, cat, cattle, swine, sheep, horse or primate). A human includes pre and post natal forms. In many embodiments, a subject is a human being. A subject can be a patient, which refers to a human presenting to a medical provider for diagnosis or treatment of a disease. A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, or condition has been diagnosed with and/or exhibits or has exhibited one or more symptoms or characteristics of the disease, disorder, or condition.

Susceptible to: An individual who is "susceptible to" a disease, disorder, or condition is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition. In some embodiments, a risk of developing a disease, disorder, and/or condition is a population-based risk (e.g., family members of individuals suffering from allergy, etc.

Traditional Chelating Agent: "traditional chelating agent" as used herein refers to those agents that, prior to the present invention, were utilized in the art to bind metal ions in a chelation complex. Labeled metal(loid) chalcogen nanoparticles as described and prepared herein do not include such traditional chelating agents. Specifically, traditional chelating agents that, in accordance with some embodiments of the present invention, are not included (e.g., at detectable levels—trace/insignificant amounts may be present from other reagents) in metal(loid) chalcogen nanoparticles for use as described herein may be selected from acetylacetone; aerobactin; aminoethylethanolamine; aminopolycarboxylic acid; ATMP; BAPTA; BDTH2; benzotriazole; bipyridine; 2,2'-bipyridine; 4,4'-bipyridine; 1,2-Bis(dimethylarsino)benzene; 1,2-Bis(dimethylphosphino)ethane; 1,2-Bis(diphenylphosphino)ethane; catechol; CDTA, chelex 100; citric acid; corrole; crown ether; 18-crown-6; cryptand; 2,2,2-cryptand; cyclen; deferasirox; deferiprone; deferoxamine; dexrazoxane; trans-1,2-diaminocyclohexane; 1,2-diaminopropane, dibenzoylmethane; diethylenetriamine; diglyme; 2,3-dihydroxybenzoic acid; dimercaprol; 2,3-dimercapto-1-propanesulfonic acid; dimercaptosuccinic acid; dimethylglioxime; DIOP; diethylenediamine; DOTA; DTPA, DTPMP; EDDHA; EDDS; EDTMP; EGTA; 1,2-ethanedithiol; ethylenediamine; Ethylenediaminetetraacetic acid, etidronic acid; ferrichrome; fluo-4; fura-2; gluconic acid; glyoxal-bis(mesitylimine); hexafluoroacetylacetone; homocitric acid; hydroxamic siderochelates; iminodiacetic acid; indo-1, metal acetylacetonates; metal dithiolene complex; metallacrown; nitrilotriacetic acid; pendetide; penicillamine; pentetic acid; phanephos; phenanthroline; O-phenylenediamine, phosphonate; phytochelatin, polyaspartic acid; porphin; porphyrin; 3-pyridylnicotinamide; 4-pyridylnicotinamide; sodium diethyldithiocarbamate; sodium polyaspartate; terpyridine; tetramethylethylenediamine; tetraphenylporphyrin; 1,4,7-triazacyclononane; triethylenetetramine; trisodium citrate; 1,4,7-trithiacyclononane; etc.

BRIEF DESCRIPTION OF THE DRAWING

The Drawing, which is comprised of at least the following Figures, is for illustration purposes only, not for limitation.

As shown in FIG. 1, the labeled metal(loid) chalcogen nanoparticles are separated from the unbound radioisotopes, non-radioactive elements, and/or metal ions by centrifuging the dispersion at 10,000 rpm for 30 seconds, but other suitable centrifugation conditions may be used. The labeled metal(loid) chalcogen nanoparticles are then redispersed in an infusion fluid (e.g., 0.9% NaCl, etc.) by a suitable method (e.g., by sonication). The labeled metal(loid) chalcogen nanoparticles are then ready for use in their desired application (e.g., ready for intravenous injection into a patient).

FIG. 2 shows images of silica nanoparticles specifically, those of ordinary skill in the art would appreciate that radioisotope binding would not affect the integrity of other metal(loid) chalcogen nanoparticles or microparticles. The scale bars are 100 nm.

FIG. 3A illustrates instant thin-layer chromatographs of radiolabeled silica nanoparticles. The red asterisk above each of the peaks denotes the origin, where the nanoparticles remain, and the black asterisk (located to the right of the red asterisk) denotes the solvent front, where the free activity would be located. Controls of buffer-only solutions (no particles) were ran with each condition, with >95% signal at the free activity peak. FIG. 3B illustrates percent radioisotope bound to silica nanoparticles as a function of time and pH. The blue (B), red (R), and green (G) lines indicate radiolabeling at pH=5.5, 7.3, and 8.8, respectively. FIG. 3C illustrates percent radioisotope bound to silica nanoparticles as a function of time and temperature. The blue (B), red (R), and green (G) lines indicate radiolabeling at 4° C., 37° C., and 70° C., respectively. FIG. 3D illustrates serum stability of silica nanoparticles radiolabeled at pH=7.3 and 70° C., then incubated in 50% FBS at 37° C.

and silica-bound Gallium-68 and Zirconium-89 (bottom panel) following intravenous injection into a mouse. The top panel shows the biodistribution of the free radioisotopes gallium-68 and zirconium-89. As shown, free Gallium-68 is rapidly cleared and collects in the bladder, while free Zirconium-89 collects (almost immediately after injection) and remains in the bones and joints. In contrast, the lower panel shows the biodistribution when Gallium-68 is bound to the silica nanoparticles. Unlike free Gallium-68, Gallium-68-bound silica nanoparticles distribute to the liver and spleen (reticuloendothelial (RES) organs) without showing signal in any other organs (e.g., bladder), which is highly desirable and unexpected. Similar results were obtained for the silica-bound Zirconium-89. Whereas free zirconium-89 collects in the bones and joints, silica-bound Zirconium-89 collects and remains in the liver and spleen (RES organs) without showing any accumulation in the bones and joints, which is highly desirable and unexpected. The lack of accumulation in the bladder with the Gallium-68-bound silica nanoparticles or bone uptake with the Zirconium-89-bound silica nanoparticles, demonstrates the in vivo stability of the medical isotope-bound silica nanoparticles. It is desirable for the medical isotope to be delivered to and to stably remain in its intended site.

Figure 6C:
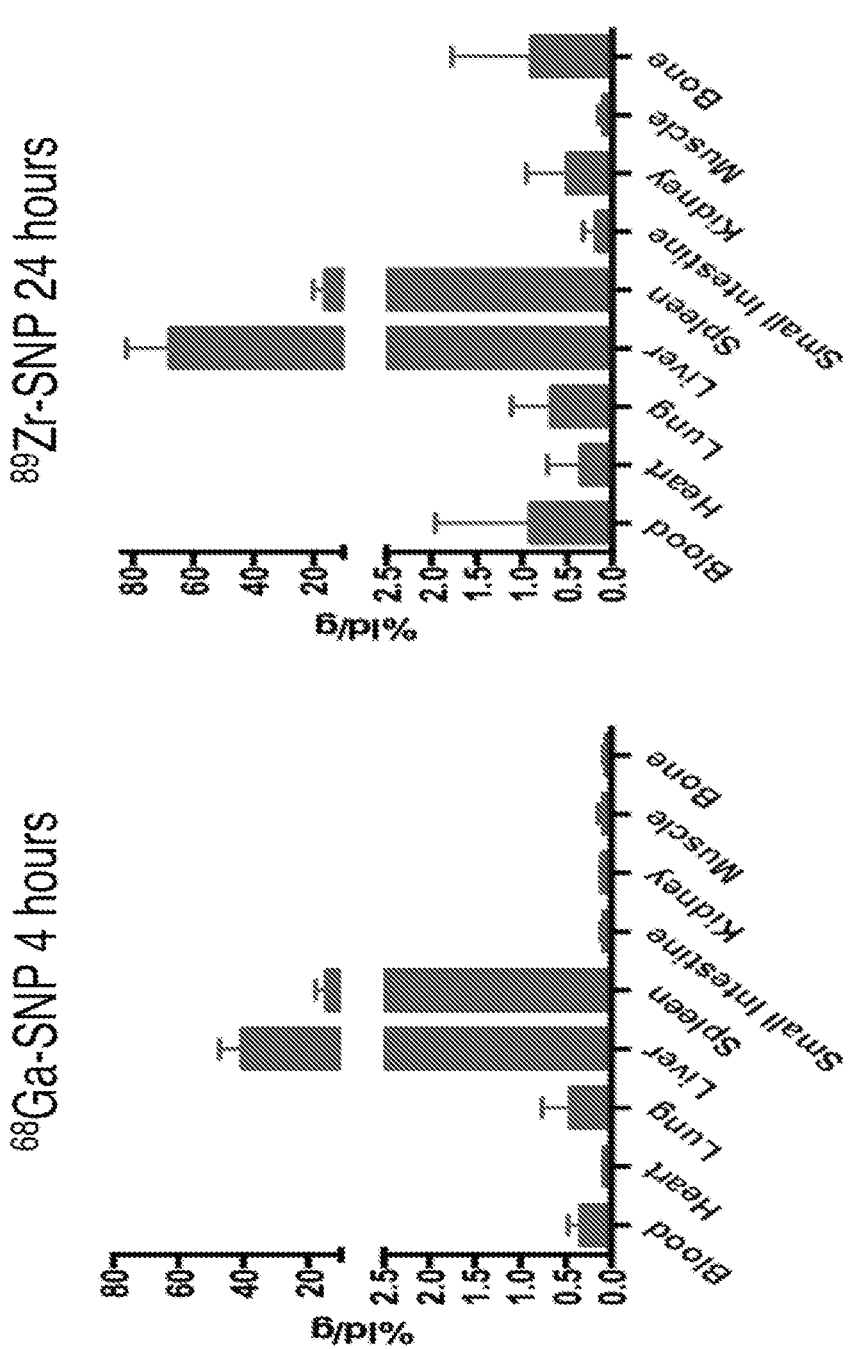
FIGS. 6A-6B illustrate a comparison of biodistribution of free radioisotopes Gallium-68 and Zirconium-89 (top panel)

FIG. 6C illustrates Biodistribution of $^{68}$Ga- and $^{89}$Zr-radiolabeled silica nanoparticles 4 hours and 24 hours post-injection, respectively. Both biodistributions are consistent with the known uptake of silica nanoparticles. The minimally elevated levels of $^{89}$Zr activity in the bone (<1% ID/g), suggest that some radioisotope leaching may be occurring in vivo, but the total amount of bone uptake is less than reported for other radiolabeled nanoparticles. These biodistributions are consistent with the observations from the PET images shown in FIGS. 6A-6B.

Figure 7:
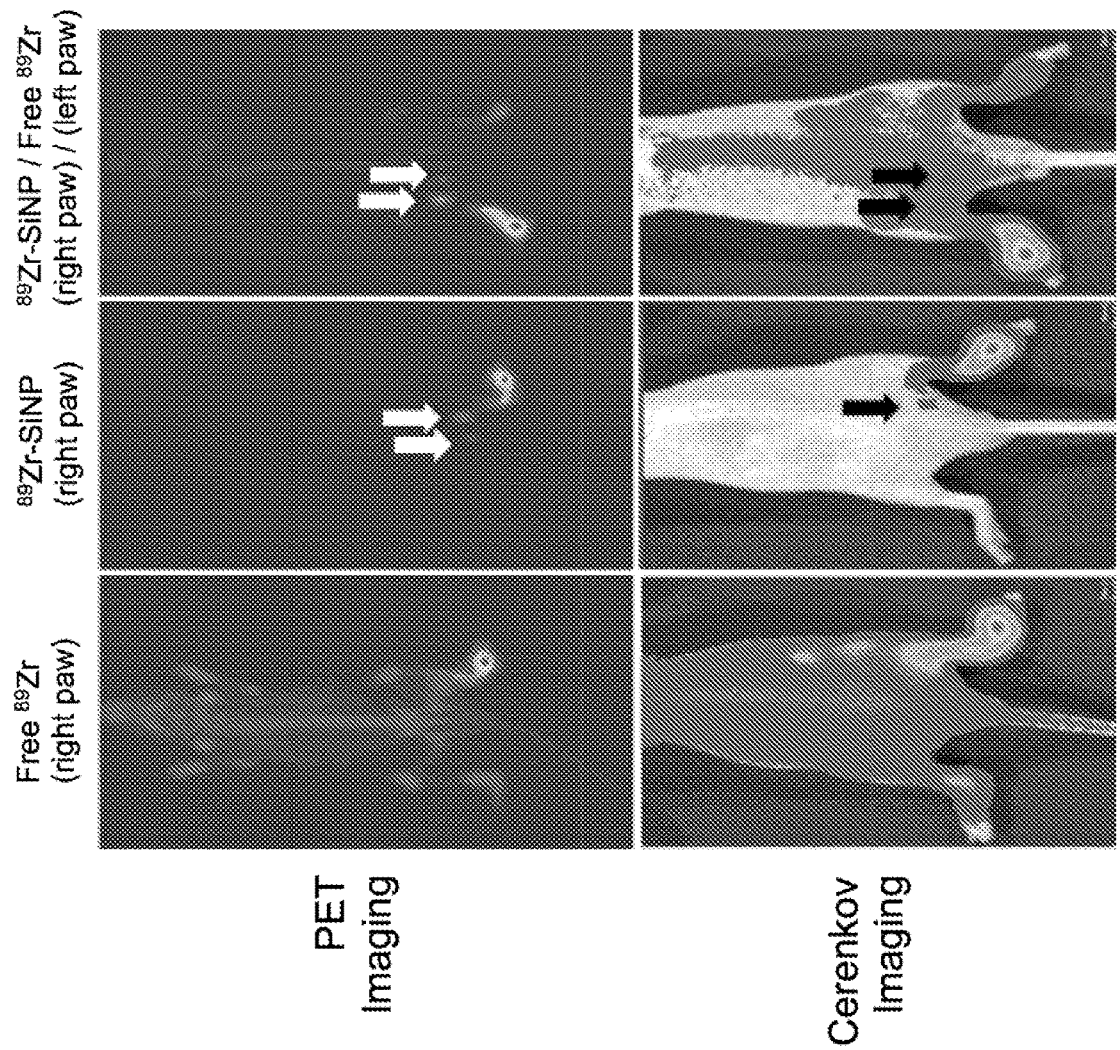

FIG. 7 demonstrates a comparison of lymph node detection capabilities with PET (top panel) and Cerenkov luminescence imaging (CLI; bottom panel) of free radioisotope Zirconium-89 and Zirconium-89-bound silica nanoparticles following subcutaneous injection into a mouse (athymic nude mice, 250-350 µCi (9.25-12.95 MBq) per injection). As shown in FIG. 7, while free Zirconium-89 distributes to the bone and does not accumulate in lymph nodes, subcutaneously injected Zirconium-89-bound silica nanoparticles accumulate only in the lymph nodes (shown via an arrow), even after 24 hours. The lack of bone uptake in the animals that was injected with the Zirconium-89-bound silica nanoparticles further demonstrates the in vivo stability of this composition, in accordance with certain embodiments of the present invention. The intrinsically labeled silica nanoparticles exhibit contrast in reticuloendothelial system, the known biodistribution of silica nanoparticles, whereas the free isotopes demonstrate an entirely different biodistribution. This stark contrast indicates that the silica nanoparticles remain intrinsically labeled in vivo.

Figure 8:
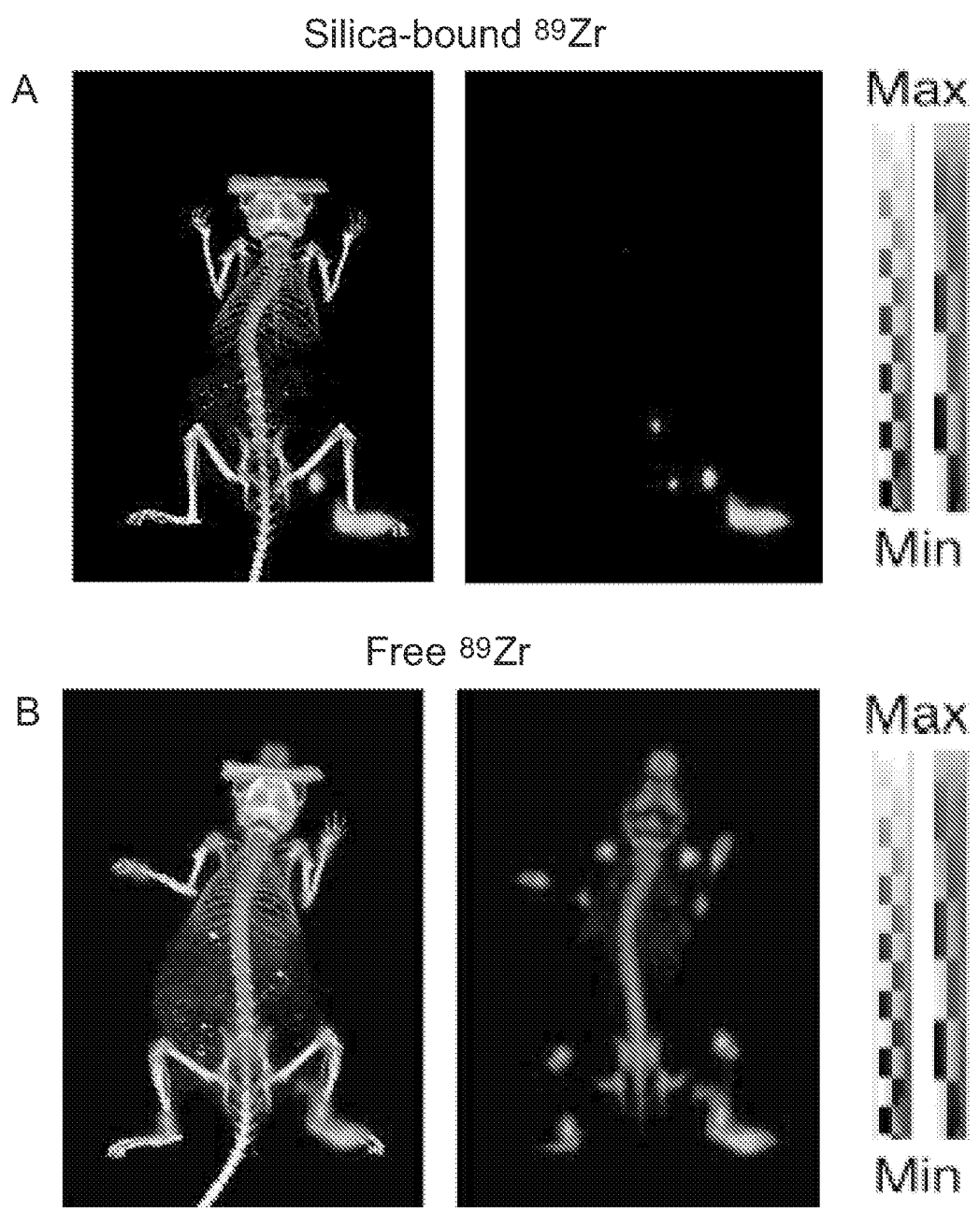

FIGS. 8A-8B demonstrate a comparison of in vivo PET-CT (left) and PET-only (right) lymph node tracking after injection in the right rear paw of athymic nude mice. FIG. 6B illustrates silica nanoparticles intrinsically labeled with $^{89}$Zr 48 hours post injection. FIG. 6C illustrates free $^{89}$Zr 48 hours post injection. Images at earlier time points demonstrated the same trend, where the free $^{89}$Zr did not accumulate in lymph nodes, while the intrinsically labeled silica nanoparticles progressively moved through the lymphatic system. As shown in FIGS. 6A-6B, while free Zirconium-89 distributes to the bone and does not accumulate in lymph nodes, subcutaneously injected Zirconium-89-bound silica nanoparticles accumulate only in the lymph nodes even after 48 hours. The lack of bone uptake in the animals that was injected with the Zirconium-89-bound silica nanoparticles further demonstrates the in vivo stability of this composition, in accordance with certain embodiments of the present invention.

Figure 9:
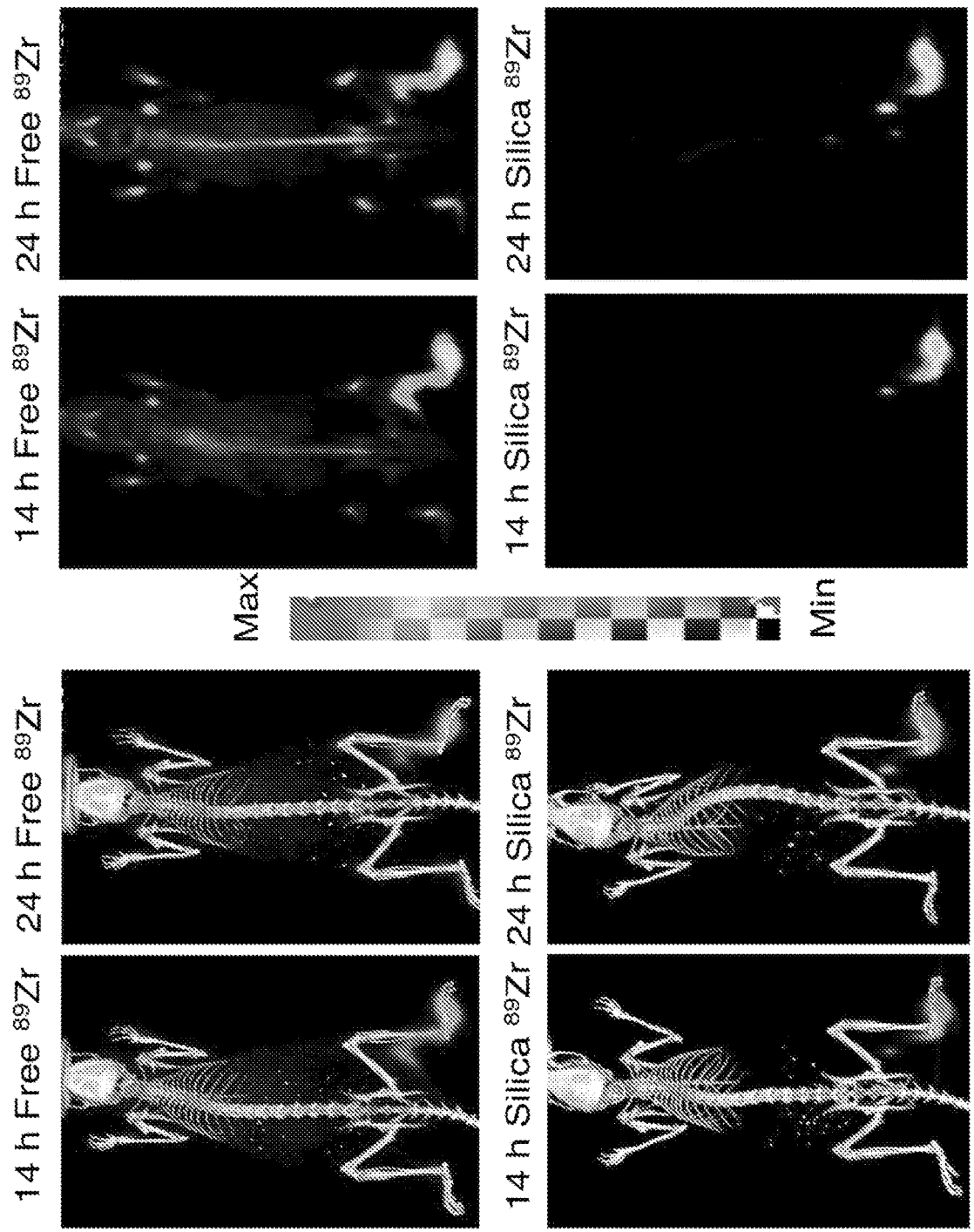

FIG. 9 demonstrates a comparison of in vivo PET-CT (left) and PET-only (right) maximum intensity projections of lymph node tracking after injection in the right rear paw of athymic nude mice. Injection amounts were 100-150 µCi (20-30 µL). The top portion of FIG. 9 shows free $^{89}$Zr at 14 hours and 24 hours post injection. The bottom portion of FIG. 9 shows silica nanoparticles intrinsically labeled with $^{89}$Zr at 14 hours and 24 hours post injection. The intrinsically labeled silica nanoparticles progressively move through the lymphatic system. White markers identify lymph nodes.

Figure 10:
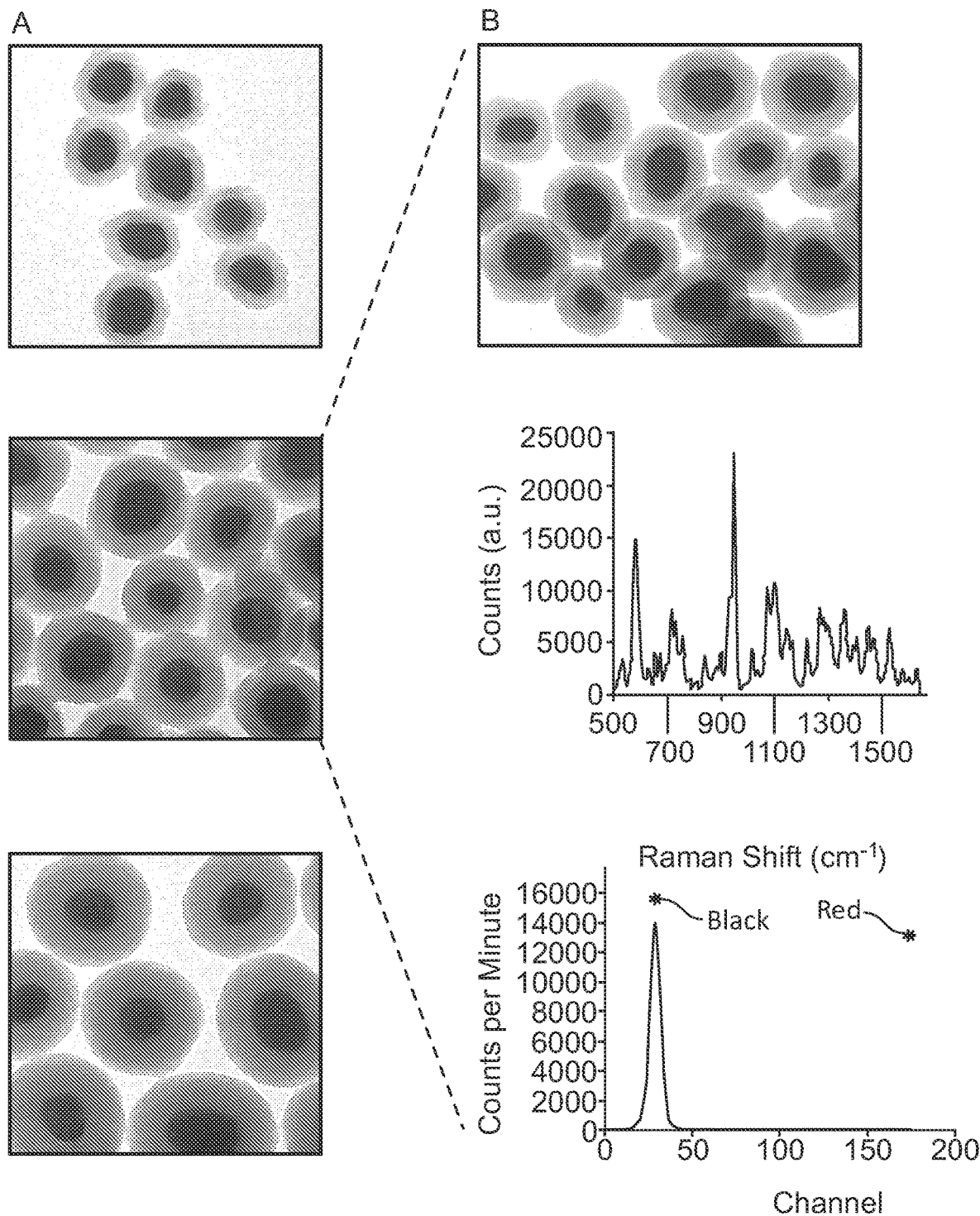

FIG. 10 illustrates chelator-free labeling of silica shells for multimodal nanoparticle synthesis. FIG. 10A illustrates silica shells of varying thickness grown around gold nanoparticles. FIG. 10B illustrates how adding Raman-active molecules to the silication procedure, as discussed in Example 2 below, generates gold-silica nanoparticles (top of FIG. 10B) that demonstrate strong surface-enhanced resonance Raman scattering (SE(R)RS) spectra (middle of FIG. 10B). The bottom of FIG. 10B demonstrates ITLC measurements revealing that radioisotopes can be stably incorporated into the silica shell by incubation with the gold-silica nanoparticles. Here, $^{64}$Cu was added to the gold-silica nanoparticles at room temperature for less than 5 minutes. Over 99% of the radioactivity is located at the nanoparticle peak (black asterisk), with negligible free radioactivity observed (red asterisk). The scale bar is 100 nm.

Figure 11A:
Figure 11B:
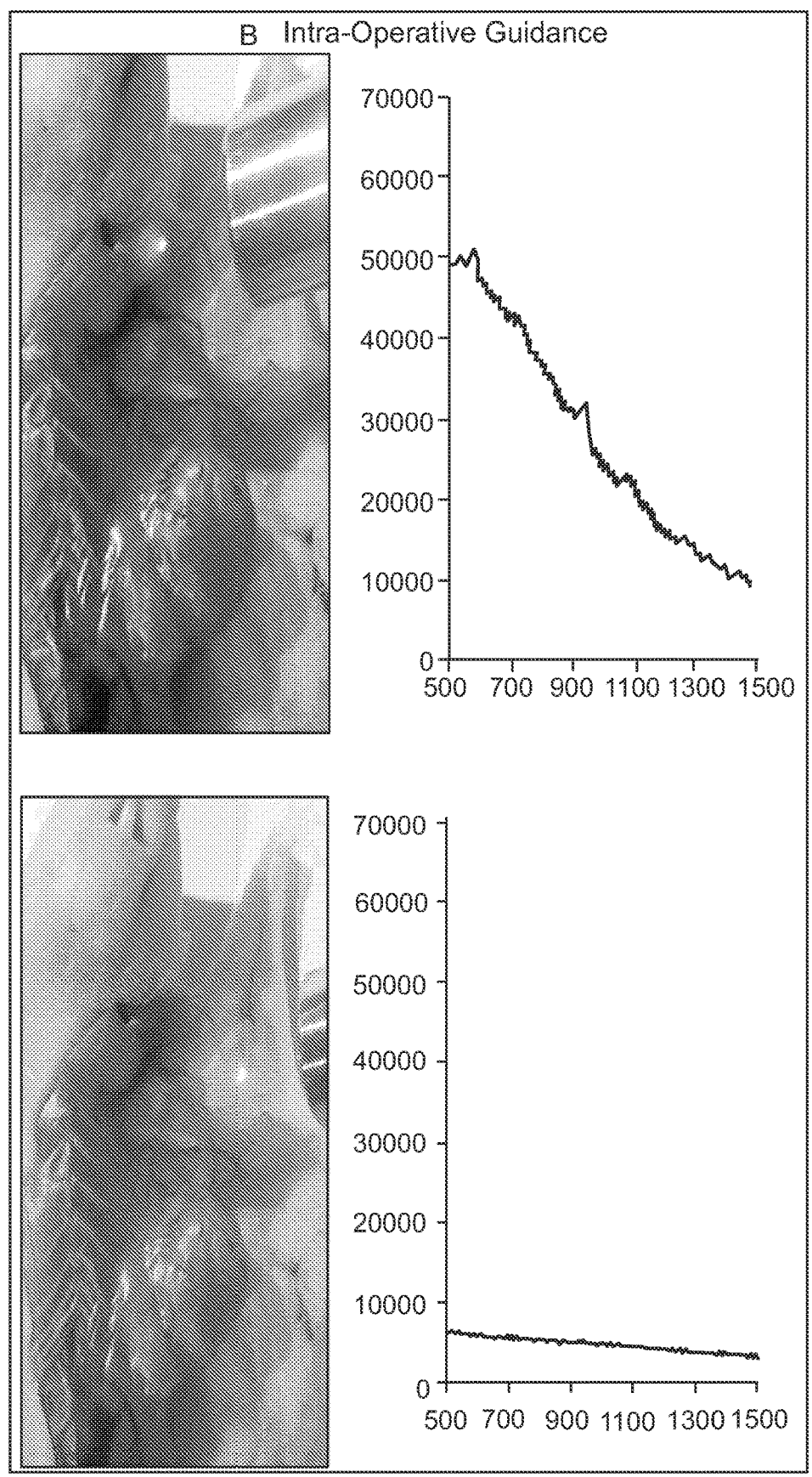
Figure 11C:
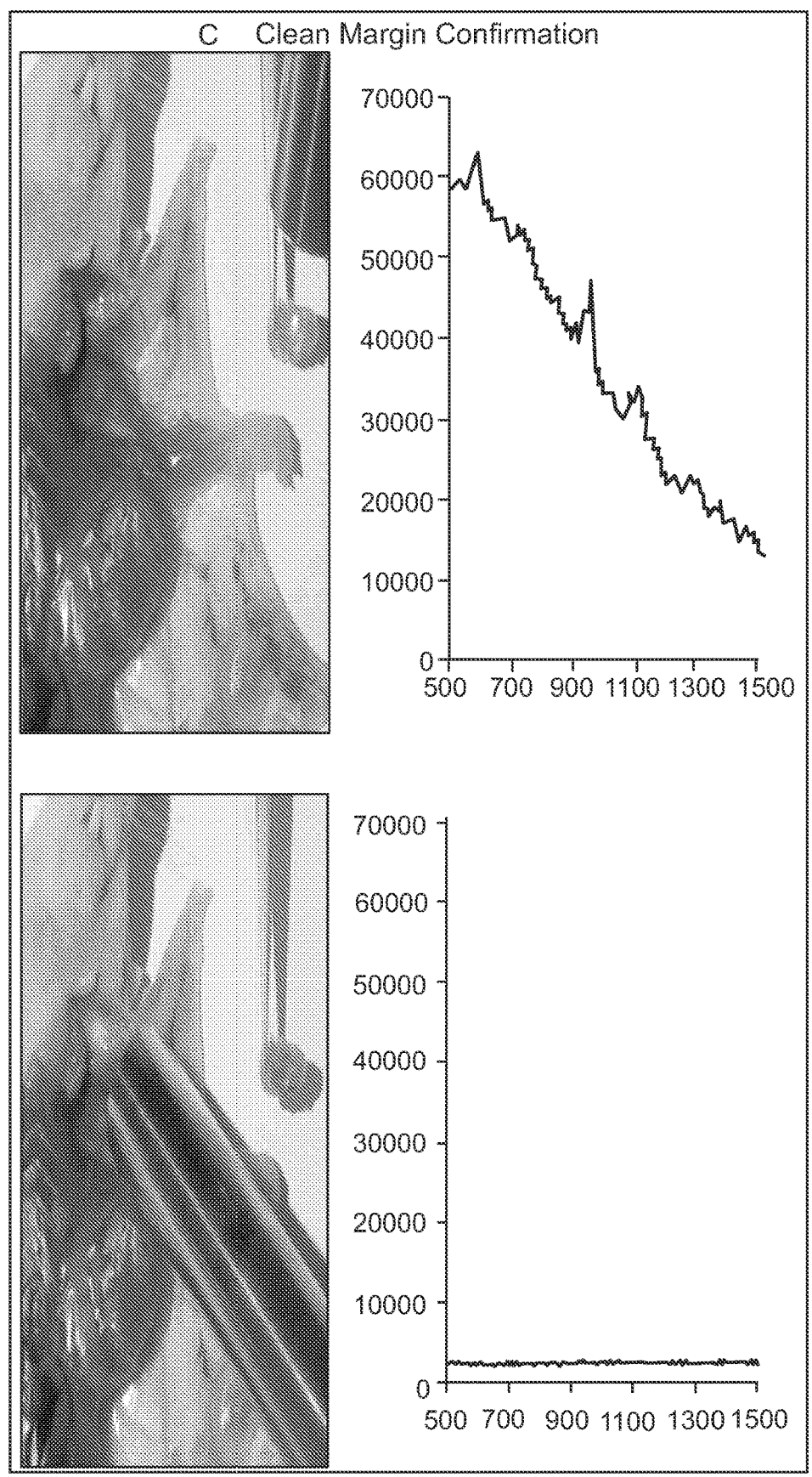

FIG. 11 demonstrates results of injecting the PET-SE(R) RS-active gold-silica nanoparticles from FIG. 10 peritumorally for lymph node tracking. FIG. 11A shows the PET contrast enabling pre-operative identification of regions of interest. FIG. 11B shows the SE(R)RS contrast enabling intraoperative guidance and clean margin assessment after the PET contrast has decayed to safe levels for surgical intervention.

Figure 12:
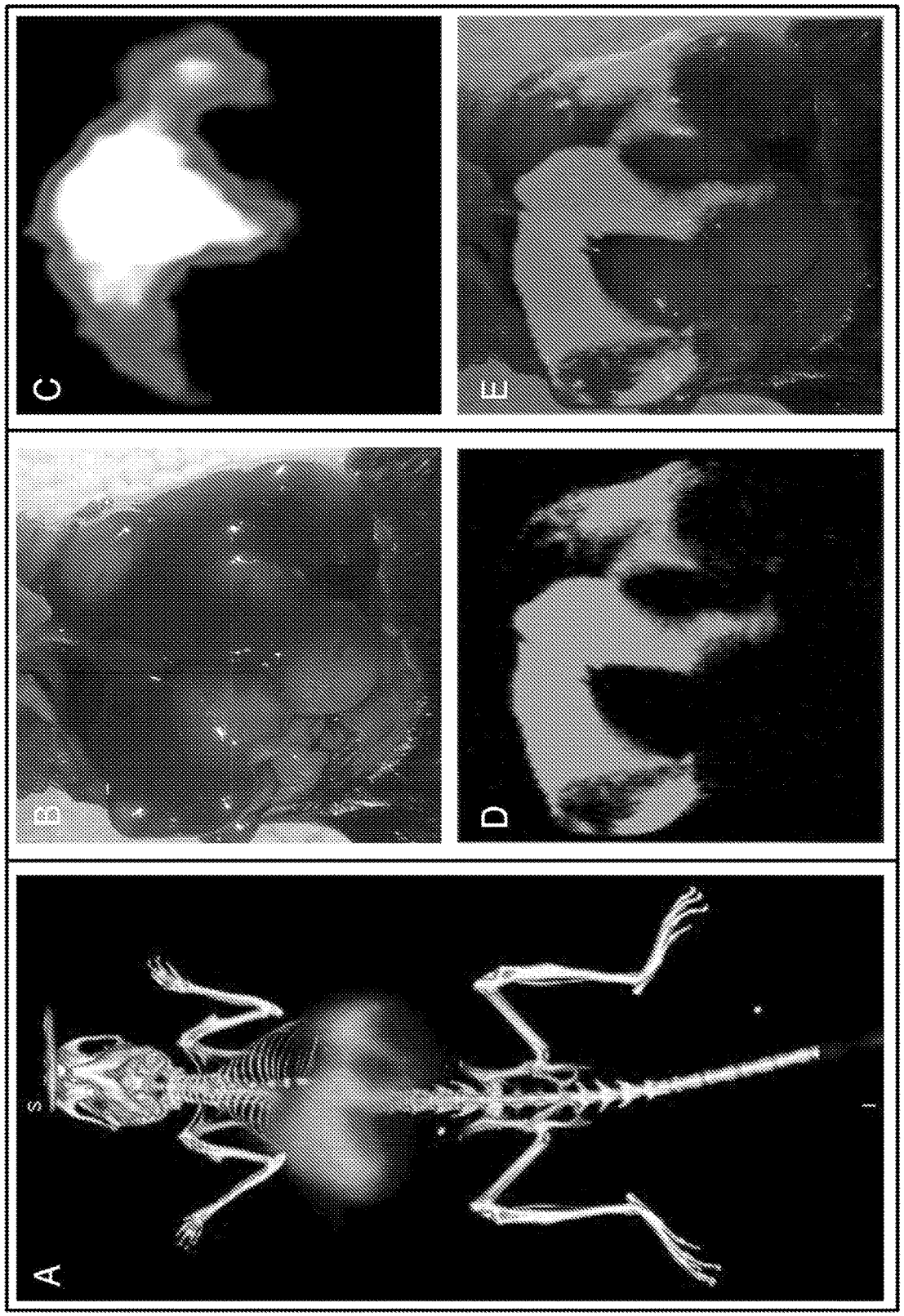

FIG. 12 demonstrates Pre-operative staging and intraoperative imaging of a liver cancer using the PET-SE(R)RS gold-silica nanoparticles from FIG. 10. FIG. 12A demonstrates a contrast provided by gold-silica nanoparticles during PET-CT imaging revealing clear filling defects that correspond to liver cancer. FIG. 12B is an intraoperative picture of tumor-bearing liver of the mouse in FIG. 12A. FIG. 12C is a maximum intensity projection (MIP) of the PET signal correlating with the healthy regions of the liver, revealing the presence of cancer via filling defects in the signal. FIG. 12D is a SE(R)RS image of the tumor-bearing liver, which reveals a higher-resolution map of the healthy liver, providing intraoperative contrast. The correlation between PET signal and SE(R)RS signal indicates that the nanoparticles remain intact and active toward both modalities in vivo. FIG. 12E is an overlay of the picture of the tumor-bearing liver and the SE(R)RS image (map), showing that the filling defects in the SE(R)RS signal correspond to cancer.

Figure 13:
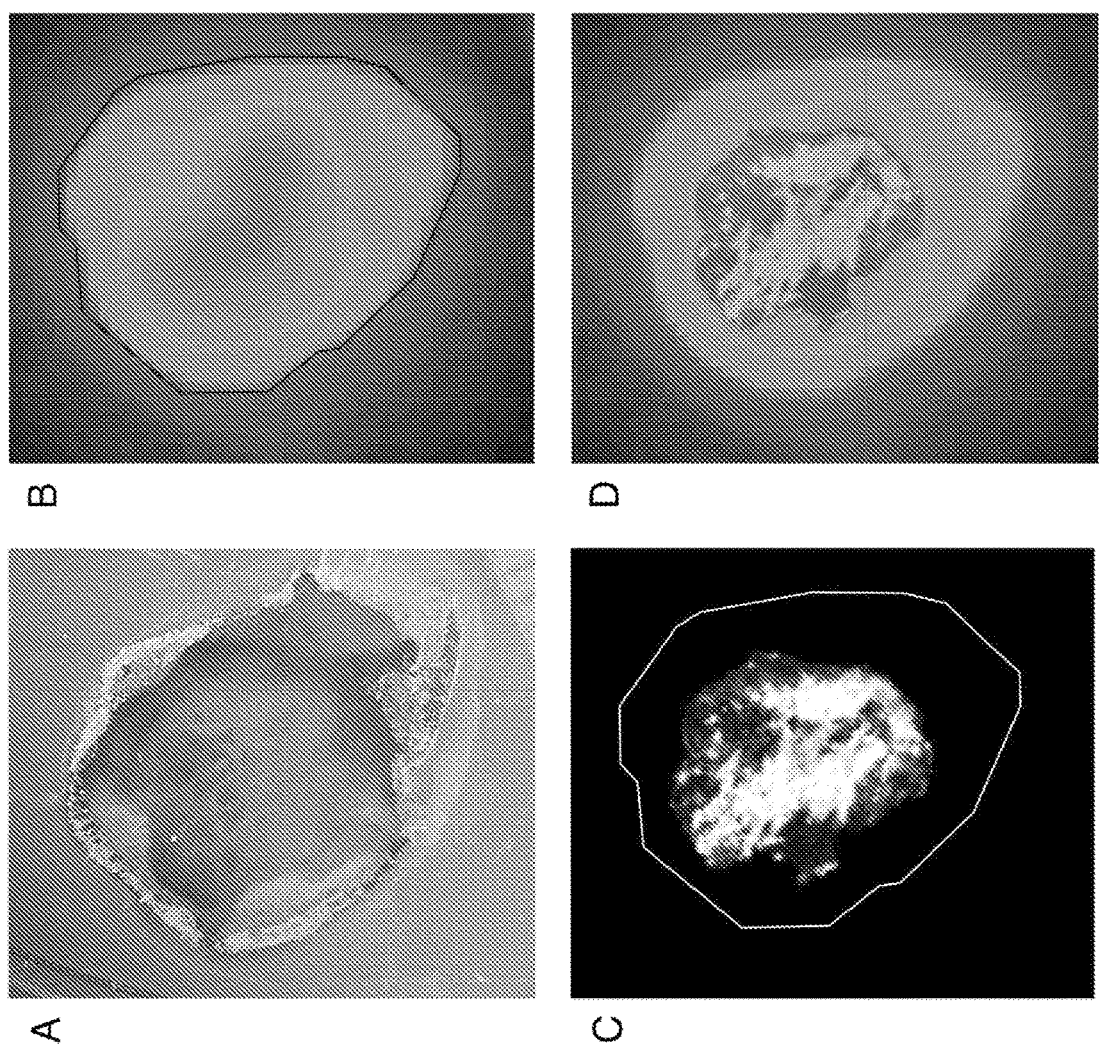

FIG. 13 demonstrates radioactivity-SE(R)RS correlation in xenograft tumors. FIG. 13A shows an image of a mouse tumor that was resected for imaging. The mouse with a neuroblastoma xenograft was injected with the PET-SE(R) RS gold-silica nanoparticles discussed in FIG. 10. FIG. 13B illustrates autoradiography revealing the presence of radioactivity at distinct locations within the tumor shown in FIG. 13A. FIG. 13C is a SE(R)RS image revealing the presence of gold-silica nanoparticles within the tumor in FIG. 13A. FIG. 13D is an overlay of the radioactivity and SE(R)RS signal showing that they co-register, indicating that the chelator-free labeling of silica shells produces nanoparticle contrast agents that remain sufficiently stable in vivo to accumulate in cancerous tissue without the need for pre-targeting.

DETAILED DESCRIPTION OF CERTAIN EMBODIMENTS

I. Binding of Metal(loid) Chalcogen Nanoparticles and Medical Isotope

In general, the present disclosure describes binding of medical isotopes to metal(loid) chalcogen nanoparticles. In some embodiments, metal(loid) chalcogen nanoparticles are bound (via e.g., covalent bonds or non-covalent (e.g., chelate) bonds) to one or more medical isotopes without the need of small molecular chelating agents. In some embodiments, the medical isotopes are chelated to the metal(loid) chalcogen nanoparticles without the use of traditional chelating agents.

The term "chelation" is typically used to describe a type of interaction through which metal ions (and/or metal-like ions) are bound (by a "chelator" or "chelating agent"). A chelating agent complexes with the metal ion (or metal-like ion), which typically involves formation of two or more coordinate bonds between the metal ion (or metal-like ion) and the chelating agent (a polydentate ligand), thereby forming a three-dimensional structure that blocks the metal ion's normal reactive sites and prevents the metal ion (or metal-like ion) from reacting as it normally would. Chelation can deactivate two or more reactive sites of a metal ion (or a metal-like ion). Alternatively or additionally, chelation can provide highly stable three-dimensional chelated complexes that are useful in a number of different applications. Controlling the activity of the metal ions (or metal-like ions), particularly for extended time periods, via chelation is advantageous or desirable in a number of different applications, including medical imaging and disease treatment, specifically including cancer treatment.

Traditionally, chelating agents are selected based on a number of different factors. One of the factors is the affinity of the chelating agent for the particular metal ion (or metal-like ion). Traditionally, chelating agents do not have universal applicability; in other words, the same chelating agent may not be used to chelate a large number of different metal ions (or metal-like ions).

Chelators for radioactive metals (and other medical isotopes) virtually always work according to the same principle: the chelating agent surrounds the (radioactive) metal ion and coordinates it by donating electron density from their lone pair electrons. Because each different element has a unique size (i.e., atomic or ionic radius) and symmetry of electron orbitals, one small molecule cannot chelate a wide library of different medical isotopes. Instead, the different medical isotopes need different numbers of electron donating atoms with different distances between them in order to form a chelated complex. Thus, traditionally it was understood that a different traditional chelating agent is needed for each particular medical isotope (e.g., radioactive metal, non-radioactive metal, non-metal, etc.).

Currently, a wide library of interesting and potentially promising medical isotopes exists, ranging, for example, from positron-emitters such as zirconium-89, gallium-68, to SPECT isotopes like technetium-99m and indium-111, and even therapeutic alpha-emitters like bismuth-213 and actinium-225. These, and many other isotopes are prized for their great potential in diagnostic imaging and disease treatment, however, these and other useful isotopes require the non-trivial design of molecular chelating agents that can form stable complexes such that they can accumulate and stably remain in sites of interest when administered—e.g., intravenously—to a subject.

In general, each different medical isotope must have a unique traditional chelating agent designed for effective use in vivo. The chemistry behind chelator design is difficult, expensive, time-consuming, and is almost always the rate-limiting step for translating a promising medical isotope to the clinic. Even when a chelator is sufficient for binding a medical isotope, it must be further modified to target a specific cancer, because, for example, small molecular chelators do not naturally accumulate in cancer. Furthermore, the small molecular chelators suffer from rapid washout from sites of interest in vivo.

Some embodiments of the present invention relate to providing a single platform for binding a wide library of medical isotopes such that they can be stably used in vivo for at least 3 hours, at least 6 hours, at least 8 hours, at least 12 hours, or at least 24 hours, without targeting or washout. Some embodiments of the present invention relate to a kit that may be purchased for making chelated labeled metal (loid) chalcogen nanoparticles—the use of the kit requires no expertise or special training for the user. Some embodiments of the present invention relate to a kit that may be purchased for making chelated labeled metal(loid) chalcogen microparticles—the use of the kit requires no expertise or special training for the user.

The present disclosure provides the surprising discovery that certain metal(loid) chalcogen nanoparticles can serve as effective universal binding agents (e.g., to facilitate covalent or non-covalent (e.g., chelate) bond formation) for a wide library of different isotopes (including medical isotopes). The present disclosure exemplifies this insight through demonstration that silica nanoparticles can bind (e.g., covalently or non-covalently) a variety of medical isotopes. Those skilled in the art, reading this disclosure will appreciate that its teachings are not limited to the specific exemplification provided. Without wishing to be bound by any particular theory, the present disclosure proposes that certain metal (loid) chalcogen nanoparticles, such as the exemplified silica nanoparticles, can provide binding moieties (e.g., via covalent- or non-covalent binding (e.g., chelation), etc.) in a variety of arrangements, numbers, and symmetry combinations, thereby permitting effective binding (e.g., covalent- or non-covalent (e.g., chelation) bonding, etc.) of a wide range of medical isotopes. Such metal(loid) chalcogen nanoparticles, in accordance with the present invention, therefore can provide an effectively universal, modular platform, for binding (e.g., covalent- or non-covalent (e.g., chelation) bonding) and presentation of medical isotopes.

In some embodiments, desirable metal(loid) chalcogen nanoparticles and microparticles for use in accordance with the present invention (including the exemplified silica nanoparticles) are microporous, for example having porosity within the range of 0.2-2 nm. In some embodiments, desirable metal(loid) chalcogen nanoparticles and microparticles for use in accordance with the present invention (including the exemplified silica nanoparticles) are mesoporous, for example having porosity within the range of 2-50 nm. In some embodiments, desirable metal(loid) chalcogen nanoparticles and microparticles for use in accordance with the present invention (including the exemplified silica nanoparticles) are macroporous, for example having porosity within the range of 50-1000 nm. Without wishing to be bound by any particular theory, the present disclosure proposes that the presence of the microporous, mesoporous, or macroporous texture of the metal(loid) chalcogen nanoparticles or microparticles discussed herein, enables (e.g., by providing sufficiently high surface area that is exposed to the medical isotope) the metal(loid) chalcogen nanoparticles or microparticles to effectively bind (e.g., covalently or non-covalently (e.g., chelation)) virtually any medical isotope.

In some embodiments, desirable metal(loid) chalcogen nanoparticles for use in accordance with the present invention (including the exemplified silica nanoparticles) are amorphous. Without wishing to be bound by any particular theory, the present disclosure proposes that the amorphous nature of the metal(loid) chalcogen nanoparticles or microparticles discussed herein, enables the metal(loid) chalcogen nanoparticles or microparticles to effectively bind (e.g., covalently or non-covalently (e.g., chelation)) virtually any medical isotope.

In some embodiments, desirable metal(loid) chalcogen nanoparticles and microparticles for use in accordance with the present invention (including the exemplified silica nanoparticles) are characterized by high densities of electron donor moieties (e.g., oxygen or sulfur atoms). Theoretically, and without wishing to be bound to any particular theory, at least 2-3 times more metal-ions would bind to the silica nanoparticle surface (thereby excluding the pore surface) than through traditional silane-coupled chelating agents.

In some embodiments, metal(loid) chalcogen nanoparticles or microparticles for use in accordance with the present invention are exposed to elevated temperatures (e.g., ≥25° C.), for example during the labeling process. For example, in some embodiments, metal(loid) chalcogen nanoparticles or microparticles are exposed to temperatures within the range of 25-95° C.; in some particular embodiments, as demonstrated in the examples, silica nanoparticles are exposed to a temperature equal to or above 70° C. during labeling (i.e., while in contact with medical isotopes as described herein).

In some particular embodiments, the labeling process is performed at an elevated temperature (e.g., at or above, and particularly above, room temperature); appropriate equipment may be provided and/or utilized. In some such embodiments, the temperature is within a range between a lower value and an upper value, inclusive, wherein the lower value is selected from the group consisting of 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C. 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 79° C., 71° C., 72° C., 73° C., 74° C., 75° C., and the upper value is selected from the group consisting of 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C. In some embodiments, the temperature is within the range of about 25° C. to about 95° C. and/or within a range of about 70° C. to about 95° C. In some particular embodiments, the reactions are performed at or around 70° C. or at or around 95° C. In some particular embodiments, the reactions are performed temperatures above 95° C.

Typically, as described herein, metal(loid) chalcogen nanoparticles or microparticles are exposed to elevated temperature in the presence of medical isotopes, and are maintained at such elevated temperature for a time period sufficient for labeling to occur (e.g., 15-120 minutes).

Without wishing to be bound by any particular theory, the present disclosure proposes that exposure to elevated temperatures, as described herein, enables the metal(loid) chalcogen nanoparticles (or microparticles) to adjust their structural configuration for effective binding (via, e.g., covalent- or non-covalent (e.g., chelation) bonding) of virtually any medical isotope (i.e., of the provided medical isotope together with which it is exposed to the elevated temperature). In some embodiments, amorphous metal(loid) chalcogen nanoparticles (or microparticles) are more facile at such adjustment. In some embodiments, such adjustment may involve breaking and/or making internal bonds within the metal(loid) chalcogen nanoparticle (or microparticle).

Thus, in some embodiments of the present invention, certain metal(loid) chalcogen nanoparticles (specifically including exemplified silica nanoparticles) or microparticles can bind (e.g., via covalent- or non-covalent (e.g., chelation) bonding) a medical isotope regardless of its size, shape, and identity. In some embodiments, metal(loid) chalcogen nanoparticles (or microparticles) of interest are particularly effective binders for oxophilic medical isotopes.

In some particular embodiments, silica nanoparticles—which are inexpensive, non-toxic, and biodegradable—are employed as universal binders as described herein. In some particular embodiments, metal(loid) chalcogen nanoparticles (e.g., silica nanoparticles) are employed to bind (e.g., via covalent- or non-covalent (e.g., chelation) bonding) radioisotopes (e.g., Zirconium-89, etc.) and/or other medical labeling (e.g., Gadolinium) and/or therapeutic isotopes (e.g., Actinium-225, Bismuth-213).

The present invention also encompasses the recognition that technologies provided herein enable simple kit-ready medical isotope binding/nanoparticle labeling useful in a variety of contexts, with a variety of metal(loid) chalcogen nanoparticles and/or medical isotopes. For example, in some embodiments, reagents useful for combining metal(loid) chalcogen nanoparticles with one or more medical isotopes as described herein are provided together in a kit. In some embodiments, such a kit has a plurality of separate compartments and/or containers, each of which, for example, may contain a particular type of metal(loid) chalcogen nanoparticle, buffer, medical isotope, control reagent, etc.

In some embodiments provided technologies for binding (e.g., covalent- or non-covalent (e.g., chelation) bonding, etc.) medical isotopes and/or labeling metal(loid) chalcogen nanoparticles include steps of combining particular metal(loid) chalcogen nanoparticles with one or more types of metal(loid) chalcogen nanoparticles (in the same or different reaction chambers), exposing the combination to elevated temperature under conditions and for a time period sufficient for binding to occur, and optionally, collecting labeled metal(loid) chalcogen nanoparticles.

Figure 1:
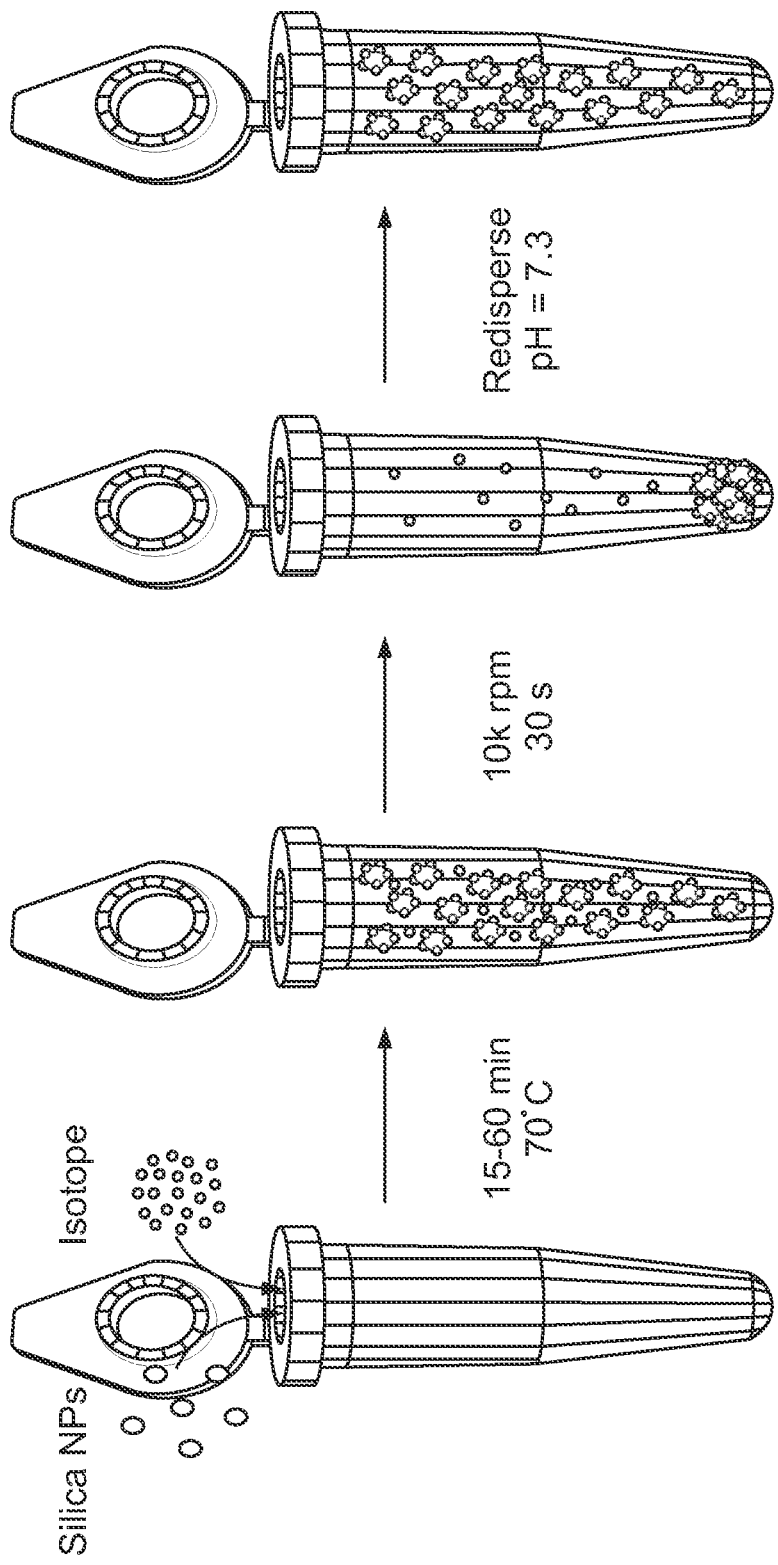
FIG. 1 shows an example experimental set-up for labeling the nanoparticles, in accordance with some embodiments of the invention. Prefabricated silica or silica-coated metal nanoparticles (which can have a size between 5-200 nm depending on the particular application) are mixed with a radioisotope (e.g., Gallium-68, Zirconium-89, Yttrium-90, Indium-111, Copper-64, Bismuth-213, Actinium-225, Lutetium-177, etc.) or with other non-radioactive elements (e.g., Gadolinium, Manganese, etc.) of interest for a particular application (e.g., (pre)clinical biomedical imaging, cancer treatment, palliative therapy, arthritis therapy, etc.). The dispersion is heated at a predetermined temperature (e.g., equal to or greater than 25° C., equal to or greater than 70° C., etc.) for a predetermined duration (e.g., 5-60 minutes, 15 to 60 minutes, 5-120 minutes, etc.). The labeled (e.g., radiolabeled) nanoparticles (e.g., silica nanoparticles) are then separated (e.g., by centrifugation, filtration, or other suitable separation methods) from the unbound radioisotopes, non-radioactive elements, and/or metal ions.

A particular exemplary experimental setup is shown in FIG. 1 and discussed above.

In some embodiments, medical isotope labeled metal(loid) chalcogen nanoparticles are immediately ready for use, for example by intravenous injection (or for other suitable delivery method, depending on the particular application) to a subject.

Alternatively, in some embodiments, medical isotope labeled metal(loid) chalcogen nanoparticles may be collected and stored (e.g., lyophilized) for a period of time. As will be appreciated by those skilled in the art, the type of metal(loid) chalcogen nanoparticle utilized in any particular application may affect the feasibility or desirability of storage. For example, in general, metal(loid) chalcogen nanoparticles labeled with radioisotopes should be utilized before the relevant radioisotope decays.

The exemplification included herein demonstrates, among other things, that medical isotopes bound metal(loid) chalcogen nanoparticles as described herein can be administered to subjects suffering from cancer without significant adverse effects. Moreover, the provided exemplification demonstrates accumulation of such delivered metal(loid) chalcogen nanoparticles in cancer tissues even without targeting moieties. Still further, the present exemplification demonstrates that accumulated metal(loid) chalcogen nanoparticles do not rapidly wash out.

The particular studies exemplified herein showed some accumulation of medical isotope labeled metal(loid) chalcogen nanoparticles in liver and spleen. Those of ordinary skill in the art, reading the present disclosure, will appreciate that where such accumulation is undesirable, choice of medical isotope can reduce negative effects of delivery. For example, use of short-lived isotopes like Gallium-68 can prevent high doses of radioactivity to these organs, while providing signal effective for medical imaging.

In some embodiments, medical isotope labeled metal (loid) chalcogen nanoparticles are delivered intravenously. In some embodiments, medical isotope labeled metal(loid) chalcogen nanoparticles are delivered orally (e.g., via ingestion by the patient). In some embodiments, medical isotope labeled metal(loid) chalcogen nanoparticles are delivered subcutaneously. In some embodiments, medical isotope labeled metal(loid) chalcogen nanoparticles are delivered intradermally. In some embodiments, medical isotope labeled metal(loid) chalcogen nanoparticles are delivered to lymph nodes or lymph vessels; in some such embodiments, delivered medical isotope labeled metal(loid) chalcogen nanoparticles permit lymphatic system imaging, which is desirable in a variety of contexts, including, for example, lymphoma.

II. Nanoparticle Compositions

In general, nanoparticles according to the present invention comprise a core, which may be comprised of a metal, a metal-like material, or a non-metal. In some embodiments, the nanoparticle core may optionally comprise one or more coating layers, surface-associated entities and/or one dopant entities. In some embodiments, nanoparticles as prepared and/or used herein do not include any coatings, surface-associated entities and/or dopants. Thus, in some embodiments, nanoparticles as prepared and/or utilized herein consist of the nanoparticle cores—e.g., metal cores, non-metal cores.

In some embodiments, the present invention provides nanoparticle compositions in which at least 50, 55%, 60%, 65%, 70%, 75%, 80%, 85%, 90%, 95% or more have a core of common defined core shape.

In some embodiments, the present invention provides nanoparticle compositions comprised of at least two distinct nanoparticle subpopulations, wherein each subpopulation is defined by a distinct shape of nanoparticle core.

In some embodiments, the present invention provides nanoparticle compositions comprised of at least two distinct nanoparticle subpopulations which are distinguishably detectable from one another. In some such embodiments, different subpopulations differ based on shape of the nanoparticle core, presence or thickness of a coating layer (e.g., a silica layer), and/or both.

In some embodiments, relevant nanoparticle core shapes are, for example, cages, cones, cylinders, cubes cuboids, hexagons, high index facet shapes (particularly for use in catalysis applications), icosahedra, octahedra, plates, prisms, pyramids, rings, rods, shells, spheres, stars, tetrahedra, etc. In some embodiments, relevant nanoparticle core shapes are discs, plates, rods, spheres, squares, or stars; in some embodiments, they are plates, rods, or stars).

In some embodiments, the present invention provides nanoparticle compositions in which nanoparticle cores are characterized by a specified degree, type, and/or location of surface availability (e.g., of active surface area unpoisoned by chemical adsorbates) for a given application. In some embodiments, this specified degree is sufficient to outperform otherwise comparable nanoparticle compositions with less or different surface availability. In some embodiments, surface availability is assessed in or for a context relating to surface dependent applications.

In some embodiments, provided nanoparticle compositions comprise or consist of nanoparticles that each comprise a core and one or more coating layers. In some embodiments, nanoparticles within provided nanoparticle compositions comprise at least one dopant (e.g., directly or indirectly associated with the core and/or with or in one or more layers).

IIA. Cores

In some embodiments, the nanoparticles comprise one and the same material (e.g. consisting of, but not limited to, compounds/materials from the group of metal/semi-metal/non-metal, -oxides, -sulfides, -carbides, -nitrides, polymers [optionally biodegradable], (poly)peptides, nucleic acids [e.g., DNA], and combinations thereof) According to various embodiments of the present disclosure, the nanoparticle can be or comprise metal (e.g., gold, silver, and the like), semi-metal or non-metal, and metal/semi-metal/non-metal oxides including silica ($SiO_2$), titania ($TiO_2$), alumina ($Al_2O_3$), zirconia ($ZrO_2$), germania ($GeO_2$), tantalum pentoxide ($Ta_2O_5$), $NbO_2$, etc., and non-oxides including metal/semi-metal/non-metal borides, carbides, sulfide and nitrides, such as titanium and its combinations (Ti, $TiB_2$, TiC, TiN, etc.). In some embodiments, the nanoparticles comprise a metal coated with a non-metal (e.g., metal nanoparticle coated with silica).

In some embodiments, the nanoparticle is a silica nanoparticle or is a metal nanoparticle coated with silica. For example, in some embodiments, the silica can be synthesized from a silica precursor including, but not limited to, alkylalkoxysilane; ethylpolysilicate; tetraethylorthosilicate (TEOS); tetramethylorthosilicate (TMOS); partially hydrolyzed TEOS; partially hydrolyzed TMOS or a combination thereof.

In some embodiments, the nanoparticles comprise a metallic core. In some embodiments, the metallic nanoparticle cores prepared and/or utilized in accordance with the present invention are comprised of a metal selected from the group consisting of gold, palladium, platinum, silver, and other metals capable of presenting a face-centered cubic structure and platinum; in some embodiments, metallic nanoparticle cores are comprised of gold. In some embodiments, metallic nanoparticle cores consist of gold.

Those skilled in the art are well aware that the shape of a nanoparticle core can profoundly impact, or even determine, key properties of the nanoparticle including, for example, optical, physical, and/or chemical properties. In some embodiments of the present invention, nanoparticles have a core shape selected from the group consisting of, cages, cones, cylinders, cubes cuboids, hexagons, icosahedra, octahedra, plates, prisms, pyramids, rings, rods, shells, spheres, stars, tetrahedra, etc. In some embodiments, relevant nanoparticle core shapes are discs, plates, rods, spheres, squares, or stars; in some embodiments, they are plates, rods, or stars).

IIB. Layers

In some embodiments, nanoparticles provided by the present invention may include one or more layers coated on the core.

In some embodiments, a layer substantially covers at least one surface of the core (or of a preceding layer). In some such embodiments, a layer substantially encapsulates the core.

In some embodiments, adjacent layers are in direct physical contact with one another; in some embodiments, adjacent layers are separated from one another so that an inter-layer space is defined; in some embodiments, such an inter-layer space is empty; in some embodiments, such an inter-layer contains liquid, one or more dopant entities, etc.

Those of ordinary skill in the art will appreciate that a layer can have any of a variety of sizes or shapes (e.g., thicknesses). In some embodiments, a layer can be porous. In some embodiments, a layer is in a shape of a thin stripe or mat. In some embodiments, one or more layers substantially or partially cover the surface of the core, or of a preceding layer.

In some embodiments, layers are arranged as shells. As will be appreciated by those skilled in the art, at least two shells can be partially extended from at least one substrate (e.g., core), concentrically extended from at least one substrate, or extended asymmetrically from at least one substrate. In some embodiments, shells may have equal thicknesses; in some embodiments, shells may have different thicknesses.

A plurality of layers each can respectively contain or be comprised of one or more materials. Layers (e.g., shells) can be or comprise, but are not limited to, one and the same material (e.g., consisting of, but not limited to, compounds/materials from the group of metal/semi-metal/non-metal, -oxides, -sulfides, -carbides, -nitrides, polymers [optionally biodegradable], (poly)peptides, nucleic acids [e.g., DNA], and combinations thereof); layers can consist of at least two different materials; different layers can consist of the same or different materials in any combination.

In some embodiments, a layer is synthesized by reacting precursors and the resulting layer is a condensation layer. Nanoparticles described herein, in some embodiments, comprise at least a condensation layer and at least another layer, which can be another condensation layer or any other layers.

According to various embodiments of the present disclosure, a layer can be or comprise metal (e.g., gold, silver, and the like), semi-metal or non-metal, and metal/semi-metal/non-metal oxides including silica ($SiO_2$), titania ($TiO_2$), alumina ($Al_2O_3$), zirconia ($ZrO_2$), germania ($GeO_2$), tantalum pentoxides ($Ta_2O_5$), $NbO_2$, etc., and non-oxides including metal/semi-metal/non-metal borides, carbides, sulfide and nitrides, such as titanium and its combinations (Ti, $TiB_2$, TiC, TiN, etc.).

Additionally or alternatively, materials of a layer can be selected from polymers, including PEG and PLGA/PEG, polymeric chelators (e.g., poly DOTA, dendrimer backbone, poly DTPA, or dendrimer alone), (multiwalled) carbon nanotubes, graphene, silicone, peptides, nucleic acids, and combinations thereof.

In some embodiments, a layer is or includes silica. For example, a silica layer can be synthesized from a silica precursor including, but not limited to, alkylalkoxysilane; ethylpolysilicate; tetraethylorthosilicate (TEOS); tetramethylorthosilicate (TMOS); partially hydrolyzed TEOS; partially hydrolyzed TMOS or a combination thereof.

In some embodiments, a layer is or includes one or more polymers, particularly polymers that which have been approved for use in humans by the U.S. Food and Drug Administration (FDA) under 21 C.F.R. § 177.2600, including, but not limited to, polyesters (e.g. polylactic acid, poly(lactic-co-glycolic acid), polycaprolactone, polyvalerolactone, poly(1,3-dioxan-2-one)); polyanhydrides (e.g. poly (sebacic anhydride)); polyethers (e.g., polyethylene glycol); polyurethanes; polymethacrylates; polyacrylates; polycyanoacrylates; copolymers of PEG and poly(ethylene oxide) (PEO).

In some embodiments, a layer is or includes at least one degradable material. Such a degradable material can be hydrolytically degradable, biodegradable, thermally degradable, enzymatically degradable, and/or photolytically degradable polyelectrolytes. In some embodiments, degradation may enable release of one or more dopant entities (e.g., agent for delivery) associated with a nanoparticle described herein.

Degradable polymers known in the art, include, for example, certain polyesters, polyanhydrides, polyorthoesters, polyphosphazenes, polyphosphoesters, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used include but are not limited to polylysine, poly(lactic acid) (PLA), poly(glycolic acid) (PGA), poly(caprolactone) (PCL), poly(lactide-co-glycolide) (PLG), poly(lactide-co-caprolactone) (PLC), and poly(glycolide-co-caprolactone) (PGC). Another exemplary degradable polymer is poly (beta-amino esters), which may be suitable for use in accordance with the present application.

In general, any layer within a nanoparticle described herein can have a thickness (e.g., an average thickness) independent of that of any other layer. In some embodiments, a layer may have a thickness within a specified range. In some embodiments, some or all layers have the same thickness or have thicknesses within the same range. In some embodiments, layers on a given nanoparticle may alternate thicknesses.

In some embodiments, a layer has an average thickness that is about or less than a thickness selected from the group consisting of 5 µm, 1 µm, 800 nm, 500 nm, 400 nm, 300 nm, 200 nm, 100 nm, 90 nm, 80 nm, 70 nm, 60 nm, 50 nm, 40 nm, 30 nm, 20 nm, 15 nm, 10 nm, 5 nm, 1 nm, 0.5 nm, or 0.1 nm. In some embodiments, a layer has an average thickness within a range between a lower limit and an upper limit, wherein the lower limit is selected from the group consisting of 0.1 nm, 0.5 nm, 1 nm, 5 nm, 10 nm, 15 nm, 20 nm, 30 nm, 40 nm, 50 nm, 60 nm, 70 nm, 80 nm, 90 nm, 100 nm, 200 nm, 300 nm, 400 nm, 500 nm, 800 nm and 1 µm, the upper limit is selected from the group consisting of 5 µm, 1 µm, 800 nm, 500 nm, 400 nm, 300 nm, 200 nm, 100 nm, 90 nm, 80 nm, 70 nm, 60 nm, 50 nm, 40 nm, 30 nm, 20 nm, 15 nm, 10 nm, 5 nm, 1 nm, and 0.5 nm, and the upper limit is greater than the lower limit. In some embodiments, a layer has a thickness within a range of between about 0.1 nm and about 5 µm, about 0.5 nm and about 200 nm, about 5 nm and about 50 nm or about 10 nm and about 30 nm.

In some embodiments, a layer can have or be modified to have one or more functional groups. Such functional groups (within or on a layer's surface) can be used for association with any agents (e.g., detectable entities, targeting entities, or PEG). Such associated agents can be dopant entities, if associated (e.g., doped) within layers. For example, targeting entities and/or PEG can be associated within one or more layers comprising degradable polymers. When the degradable polymers degrade, the dopant entities can be exposed.

In some embodiments, part or all of the surface of an outer-most layer can be modified, for example to add and/or modify functional groups present on the outer-most layer. To give but a few examples, reagents such as, but not limited to, mercaptosilanols or aminosilanols can be used to introduce sulfhydryl or amine groups, respectively, to silica, tantalia, etc.; catechol-amines can be used to introduce cationic amine-functionality to titania, etc. Alternatively or additionally, hydrogen peroxide can be utilized to oxidize sulfhydryl-groups (including introduced sulfhydryl groups) to generate anionic sulfonate-functionality.

Those of ordinary skill in the art will appreciate that, in some embodiments, such strategies may modify surface charge of nanoparticles. Alternatively or additionally, such strategies may introduce functional groups that, for example, allow conjugation of linkers (e.g., (cleavable or (bio-)degradable) polymers such as, but not limited to, polyethylene glycol, polypropylene glycol, PLGA, etc.), targeting/homing agents (e.g., such as, but not limited to, small molecules (e.g., folates, dyes, etc.), (poly)peptides (e.g., RGD, epidermal growth factor, chlorotoxin, etc.), antibodies, proteins, etc.), contrast/imaging agents (e.g., fluorescent dyes, (chelated) radioisotopes (SPECT, PET), MR-active agents, CT-agents), therapeutic agents (e.g., small molecule drugs, therapeutic (poly)peptides, therapeutic antibodies, (chelated) radioisotopes, etc.), or combinations thereof, to nanoparticle surfaces.

IIC. Surface-Associated Entities

In some embodiments, nanoparticles may have one or more surface-associated entities such as stabilizing entities, targeting entities, etc. In some embodiments, such surface-associated entities are or are comprised in a layer as discussed herein. In some embodiments, such entities are associated with or attached to a core; in some embodiments, such entities are associated with or attached to a layer.

In fact, in some embodiments, the present invention identifies the source of a problem with existing nanoparticle systems that utilize or include surface-associated entities in that limitations are often present in range of entities that can be caused to associate with a nanoparticle surface (e.g., a nanoparticle core surface) after preparation because many preparation technologies leave surfaces associated with agents or moieties that participate in and/or are required for the synthesis. These synthesis-related agents or moieties must be displaced in order to associate the surface with any other entity. Thus, the range of entities that can be caused to associate with nanoparticle surfaces, in many instances, is limited to those with sufficient affinity and other characteristics to displaced the synthesis-related agents or moieties.

For example, in some embodiments it may be desirable to associate one or more of 1) targeting agents or moieties; 2) therapeutic agents or moieties; 3) detectable agents or moieties; 4) immune-modifying (e.g., immune avoiding, immune suppressing, immune stimulating, or immune activating) agents or moieties; 5) stabilizing agents or moieties with nanoparticle surfaces (see, for instance, gold particles provided by CytImmune Sciences Inc which are said to have 1) tumor-targeting molecules, 2) immune-avoiding molecules; and 3) therapeutic molecules associated with their surface. In certain embodiments, any or all such agents may be associated with surfaces of provided nanoparticles, and indeed the range of particular compounds that may be utilized with provided nanoparticles is significantly greater than the particular ones described by CytImmune Sciences Inc., or others). In some embodiments, surface associated agents included in nanoparticle compositions or otherwise utilized in accordance with the present invention are non-immunogenic as utilized; in some such embodiments, such agents are non-immunogenic in that they do not induce in a subject (e.g., a human subject) to whom they are administered a harmful immune reaction.

IID. Dopant Entities

In some embodiments, prior to medical isotope labeling, the prefabricated metal(loid) chalcogen nanoparticle are doped with dopant entities In accordance with many embodiments of the present disclosure, dopant entities are attached directly or indirectly to a nanoparticle core, or to one or more layers. In some embodiments, dopant entities are distributed within one or more layers; in some embodiments, dopant entities are discretely localized within one or more layers.

In general, any entity of interest can be utilized as a dopant entity in accordance with the present invention. In some embodiments, a dopant entity is or comprises a detectable entity such as, for example, an entity selected from the group consisting of fluorochromes (e.g., near infrared (metal-enhanced) fluorescence agents, 2-photon fluorescence agents, etc. such as Alexa 647, Alexa 488 and the like), (laser) pumping materials (e.g., consisting of, but not limited to, materials from the group of the rare-earth metal- and/or transition metal-based compounds), luminescent compounds consisting of, but not limited to rare-earth metals and/or transition metals photoacoustic-active dyes, surface-enhanced (resonance) Raman scattering (SE(R)RS)-active agents, upconverting materials (e.g. consisting of materials from the group of the rare-earth metals and/or transition metals), "slow light"-inducing materials (e.g., praseodymium-based compounds), ultrasound (US) agents, and any combination thereof.

SE(R)RS-active Agents

In some embodiments, a dopant entity is or comprises a dye, for example, a resonance dye. A dopant entity can be or comprise an agent useful in Raman spectroscopy (e.g., SE(R)RS-active agents). Exemplary dopant entities include, but are not limited to, those agents described in the art such as in U.S. Pat. Nos. 5,306,403, 6,002,471, and 6,174,677, the contents of which are incorporated by reference. Certain particles including SER(R)RS active agents, methods, and uses thereof, are discussed, for example in International Application Publication No. WO2014/036470, filed on Aug. 30, 2013, which is incorporated herein by reference in its entirety.

In some particular embodiments, a dopant entity is SE(R)RS- and/or photoacoustic active agent(s). In some particular embodiments, a high density of a SE(R)RS-active agent located close to a substrate contributes to unprecedented Raman sensitivity achieved by a particle described herein. SE(R)RS-active agents generally benefit from signal intensity enhancement in the proximity of a metal surface. In accordance with the present disclosure, a skilled artisan in the art would be capable to choose a SE(R)RS-active agent, to achieve chemical enhancement and/or electromagnetic enhancement, considering factors such as substrate materials, substrate configurations, layer material, etc. Such a SE(R)RS-active agent can have a charge transfer effect, from a metal to the molecule, or from the molecule to the metal.

A SE(R)RS-active agent refers to a molecule that is capable of generating a SERS or SE(R)RS spectrum when appropriately illuminated. Non-limiting examples of SE(R) RS-active agents include phthalocyanines such as methyl, nitrosyl, sulphonyl and amino phthalocyanines, naphthalocyanines, chalcogen-based dyes, azomethines, cyanines, squaraines, and xanthines such as the methyl, nitro, sulphano and amino derivatives. Each of these may be substituted in any conventional manner, giving rise to a large number of useful labels. It is noted that the choice of a SE(R)RS-active agent can be influenced by factors such as the resonance frequency of the molecule, the resonance frequency of other molecules present in a sample, etc.

Typically, detecting a SE(R)RS signal involves using incident light from a laser. The exact frequency chosen will depend on the SE(R)RS-active agent, and metal surface. Frequencies in visible or near-infrared spectrum tend, on the whole, to give rise to better surface enhancement effects for noble metal surfaces such as silver and gold. However, it is possible to envisage situations in which other frequencies, for instance in the ultraviolet range might be used. The selection and, if necessary, tuning of an appropriate light source, with an appropriate frequency and power, will be well within the capabilities of one of ordinary skill in the art, particularly on referring to the available SE(R)RS literature.

The Raman enhancement generally is proportional to the density of a SE(R)RS-active agent associated (e.g., adsorbed) on a metal surface. A surprisingly high density of a SE(R)RS-active agent adsorbed on a substrate surface in accordance with the present disclosure may contribute to the superior sensitivity of particles disclosed herein.

Fluorescent Agents

In some embodiments, a dopant entity is or comprises a fluorescent dye/agent (e.g., near infrared (NIR) fluorescent dye). For example, fluorescent dyes/agents including, but not limited to, polymethines, cyanines, (na)phthalocyanines, porphorines, merocyanines, (pe)rylene (bisimides), squaraines, anthocyanins, phycocyanins, bodipys, rotaxanes, rhodamines, certain organometallic complexes, can be used in accordance with the present invention.

IIE. Nanoparticle Characteristics

Nanoparticles have a size (as determined by their longest dimension) that typically does not exceed about 10 µm. In some embodiments, nanoparticles are characterized by having at least one dimension that is about or less than a length selected from 10 µm, 5 µm, 1 µm, 800 nm, 500 nm, 400 nm, 300 nm, 200 nm, 180 nm, 150 nm, 120 nm, 110 nm, 100 nm, 90 nm, 80 nm, 70 nm, 60 nm, 50 nm, 40 nm, 30 nm, 20 nm, 10 nm, 5 nm, 2 nm, or even 1 nm. In some embodiments, nanoparticles are characterized by having a longest dimension that is about or less than a length selected from 10 µm, 5 µm, 1 µm, 800 nm, 500 nm, 400 nm, 300 nm, 200 nm, 180 nm, 150 nm, 120 nm, 110 nm, 100 nm, 90 nm, 80 nm, 70 nm, 60 nm, 50 nm, 40 nm, 30 nm, 20 nm, 10 nm, 5 nm, 2 nm, or even 1 nm.

In some embodiments, nanoparticles have a size within a range bounded by a lower limit that is about or more than a length selected from 1 nm, 2 nm, 5 nm, 10 nm, 20 nm, 30 nm, 40 nm, 50 nm, 60 nm, 70 nm, 80 nm, 90 nm, 100 nm, 110 nm, 120 nm, 150 nm, 180 nm, 200 nm, 300 nm, 400 nm, 500 nm, 800 nm, 1 µm, or 5 µm, and an upper limit that is about or less than a length selected from 10 µm, 5 µm, 1 µm, 800 nm, 500 nm, 400 nm, 300 nm, 200 nm, 180 nm, 150 nm, 120 nm, 110 nm, 90 nm, 80 nm, 70 nm, 60 nm, 50 nm, 40 nm, 30 nm, 20 nm, 10 nm, 5 nm, and 2 nm, the upper limit being larger than the lower limit.

In some embodiments, a nanoparticle has a shape that is the same as the shape of its core; in some embodiments, a nanoparticle has a shape different from that of its core (e.g., if it has a coating that comprises one or more layers whose thickness varies).

It will be appreciated by those skilled in the art that particular sizes and/or shapes of nanoparticles may be especially desirable or useful in particular contexts. For example, nanoparticles for in vivo application typically have a size within a range from about 0.5 nm to about 200 nm; nanoparticles for in vitro applications often have a size within a range from about 10 nm to about 1000 nm.

In some embodiments, nanoparticles act as platforms for loading therapeutics and contrast agents while simultaneously anchoring target ligands or stealth polymer coatings.

In some embodiments, nanoparticle sizes and surface charges are tuned to be provided to sites of interest for particular applications. In some embodiments, nanoparticle size and/or surface chemistry are tuned for nanoparticle to exhibit attractive biological properties, such as passive accumulation and retention in cancer (e.g., in contrast to the rapid washout often observed by small molecular imaging agents). In many embodiments, a site of interest is or comprises a tumor. In some embodiments, nanoparticles are designed and constructed to enter tumors via their leaky vasculature. In some embodiments, nanoparticles (including the prepared chelated labeled nanoparticles) are designed and constructed to enter and/or be retained in tumors via phagocytosis by tumor (associated) cells (known as "enhanced permeability and retention (EPR)" effect). In certain embodiments, nanoparticles (including the prepared chelated labeled nanoparticles) do not wash out of a tumor, but are retained stably within the tumor (e.g., retention time at least 1 day-7 days).

III. Uses and Applications

Those of ordinary skill in the art, reading the present disclosure, will immediately appreciate that provided methodologies and compositions are useful in a wide range of contexts, including both medical and non-medical applications.

Nanoparticle systems (e.g., silica nanoparticles) have tremendous potential and are useful in a wide variety of contexts, including in electronics (e.g., as transistors or conductors, useful among other things in printable inks and/or electronic chips, for example, to connect components such as resistors, conductors, and/or other elements), to generate heat (e.g., when excited by radiation, for use in photodynamic and/or hyperthermia therapy), to deliver payloads (e.g., therapeutic, diagnostic, and/or imaging payloads), sensor technologies (e.g., colorimetric sensors, for example that identify foods suitable for consumption), for imaging indications (e.g., utilizing transmission electron microscopy, surface enhanced Raman spectroscopy and/or light scattering technologies), and catalysis (e.g., to catalyze selective oxidation reactions and/or to reduce production of nitrogen oxides or other toxic or environmentally harmful compounds). Nanoparticle systems are of particular interest for use in imaging tumor resection boundaries and/or for detecting biomarkers (e.g., in the diagnosis of heart diseases, cancer, infection, etc.). Nanoparticle systems are also often employed in lateral flow assays such as home pregnancy tests. Certain nanoparticle systems are also being developed for fuel cell and/or alternative energy applications. Provided nanoparticle compositions are particularly useful in (pre) clinical biomedical imaging and therapeutic applications.

The compositions and methods provided herein are particularly useful, for instance, in biomedical research methodologies (such as, but not limited to, cell tracking, cell sorting, western blotting), solar cells, quantum computingbased applications/methods, anti-counterfeit applications/methods, barcoding, optics, (nano)photonics.

Another particular use for provided compositions and methodologies is in clinical imaging, for example during surgery (e.g., to define tumor resection boundaries).

In some embodiments, uses of medical isotope labeled metal(loid) chalcogen nanoparticles comprise administering nanoparticles (e.g., nanoparticle compositions) to a single sample, source, or site (e.g., subject) of interest.

EXEMPLIFICATION

Example 1: Synthesis of Labeled Silica Nanoparticles

Those of ordinary skill in the art, reading the present disclosure, will immediately appreciate that metal(loid) chalcogen nanoparticles can be synthesized by a variety of methods. Without wishing to be bound to a specific synthesis procedure, the silica nanoparticles used in Example 1 were produced via a modified Stober reaction. In brief, microporous 120 nm silica nanoparticles were synthesized by reacting 1.25 ml tetraethyl orthosilicate, 625 µL 28% ammonium hydroxide, and 3.75 ml of ultrapure water in 25 ml ethanol for 50-60 minutes at ambient conditions.

The hydrodynamic diameter of the silica nanoparticles pre- and post-labeling were determined through DLS (Nano-ZS, Malvern, Westborough, Mass.). The same instrument was used in nanoparticle surface charge measurement (ζ potential) in ultrapure water (>18.2 MΩ cm$^{-1}$ at 25° C., Milli-Q, Millipore, Billerica, Mass.). To determine silica nanoparticle concentration, an NS500 instrument was utilized (NanoSight, Duxbury, Mass.).

The as-synthesized silica nanoparticles were collected by centrifugation (20 min, 6000×g), washed with ethanol, and re-dispersed in 10 mM MES buffer (pH 7). 100 µL 3-4 nM silica nanoparticles were labeled with 500 µCi $^{89}$Zr in 10 mM MES buffer (pH 7) at 70° C. for 60 minutes. The $^{89}$Zr-labeled-silica nanoparticles were collected by centrifugation and free $^{89}$Zr was removed by successive washing of the pellet. Purification was determined via instant thin layer chromatography (ITLC). The pure Zr-labeled silica nanoparticles were redispersed in 10 mM MES and intravenously injected via tail vein in a mouse.

Figure 2:
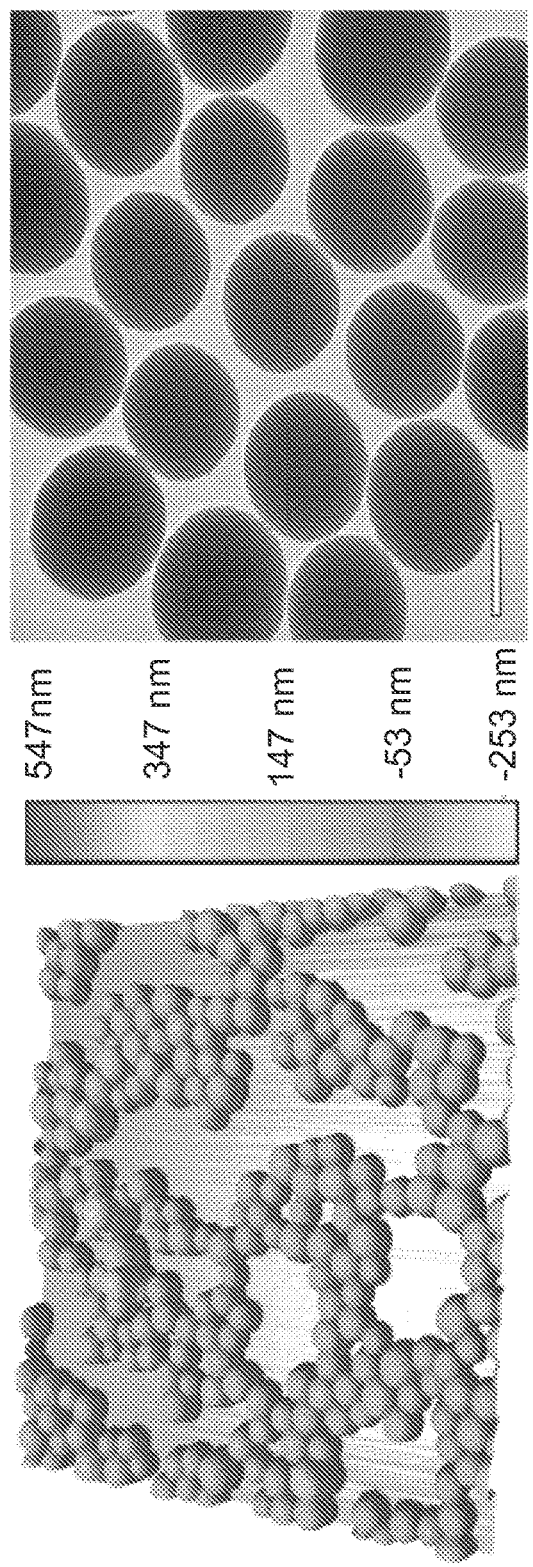
FIG. 2 illustrates a comparison of unlabeled (top panel) and radioisotope-bound (labeled) silica nanoparticles (bottom panel). The images on the left were taken with use of atomic force microscopy (AFM), and the images on the right were taken with use of transmission electron microscopy (TEM). Apart from the radiolabeling of the nanoparticles with $^{68}$Ga, the silica nanoparticles remained unchanged and were not affected by the radiolabeling procedure. Thus, as is shown in FIG. 2, radioisotope binding (labeling) does not affect the integrity of the silica nanoparticles. The size and shape of the nanoparticles remains unchanged. Although
Figure 2:
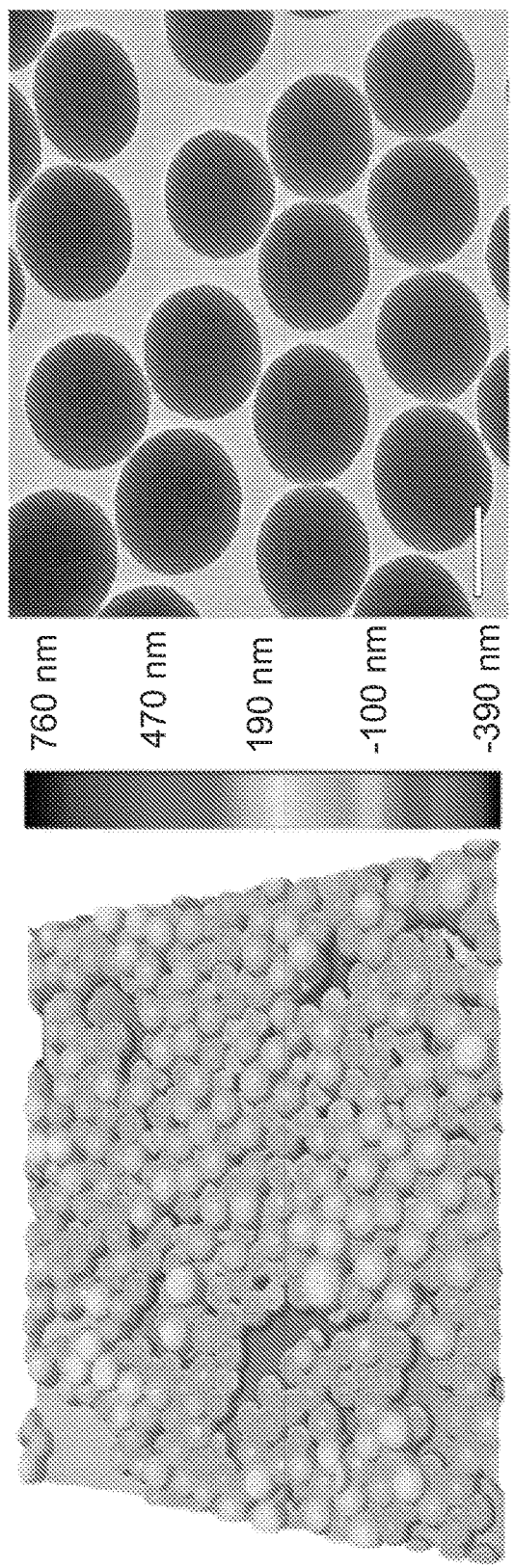

In some experiments, 145 nm silica nanoparticles were washed three times in ethanol and then re-suspended in buffered solutions at either pH=5.7, 7.3, or 8.8. The silica nanoparticles maintained a constant size and did not aggregate during processing, as shown in FIG. 2. The radiochemical yield was assessed both by ITLC and centrifugal nanoparticle purification, as discussed in further detail in reference to FIGS. 3A-3D.

Figure 4:
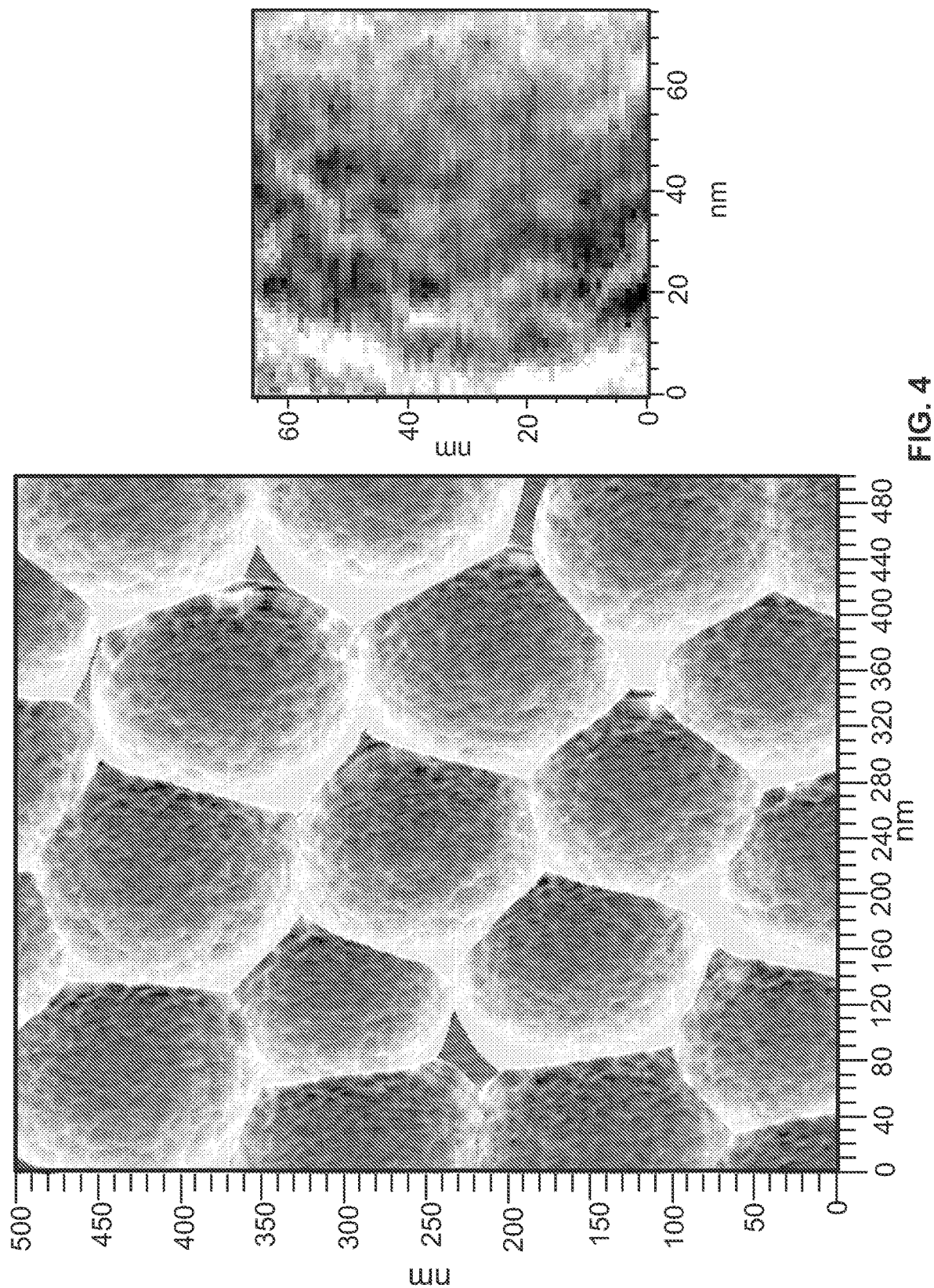
FIG. 4 shows pore size of silica nanoparticles. Atomic force microscopy of silica nanoparticle samples reveals porous surfaces with many pore diameters in excess of 5 nm. Low magnification phase images (left) and high-magnification phase images (right) were acquired in tapping mode as described herein. The porosity of these silica nanoparticles is sufficient for diffusion of radioisotopes into the nanoparticle interior, making chelation feasible anywhere within the nanoparticle (e.g., chelation is not restricted to the surface).

When the specific activity was 100 Ci/µmol, all isotopes tested demonstrated radiochemical yields of >99% (as measured by centrifugal nanoparticle purification) at pH=7.3, 70° C., and incubation times less than or equal to one hour. The radiochemical yield improved as temperature increased from 4° C. to 70° C., but did not vary significantly as a function of pH in the range investigated (pH=5.7-8.8). Buffer without silica nanoparticles was used as a control for each condition to exclude the possibility of false-positive signals due to precipitate formation. Every isotope except $^{177}$Lu showed >95% activity as free in solution. Because $^{177}$Lu exhibits >10% signal associated with precipitate formation in the buffer control, centrifugation and size exclusion filtration is necessary in the analysis of $^{177}$Lu radiolabeling to ensure that false-positive signals from precipitates do not occur. Separating the particles from the supernatant showed that all of the radioactivity was associated with the nanoparticles, independent of temperature. Competitive chelation studies with ethylenediaminetetraacetic acid (EDTA) demonstrated that samples incubated at 70° C. robustly retained the various isotopes. This suggests that the dominant influence of the temperature may be in overcoming the activation energy required for stable radioisotope binding, rather than enabling delivery of the radioisotopes to binding sites (i.e., suggesting that the process is reaction limited, not diffusion limited). This finding is supported by the observation that the silica nanoparticles are sufficiently porous to enable diffusion of the radioisotopes throughout the nanoparticle interior (e.g., as shown, for example, in FIG. 4). While heating the particles to 70° C. in some embodiments may preclude pre-labeling attachment of temperature-sensitive targeting ligands such as antibodies, other targeting ligands that are stable at this temperature such as smaller peptides and aptamers may be used.

Figure 5:
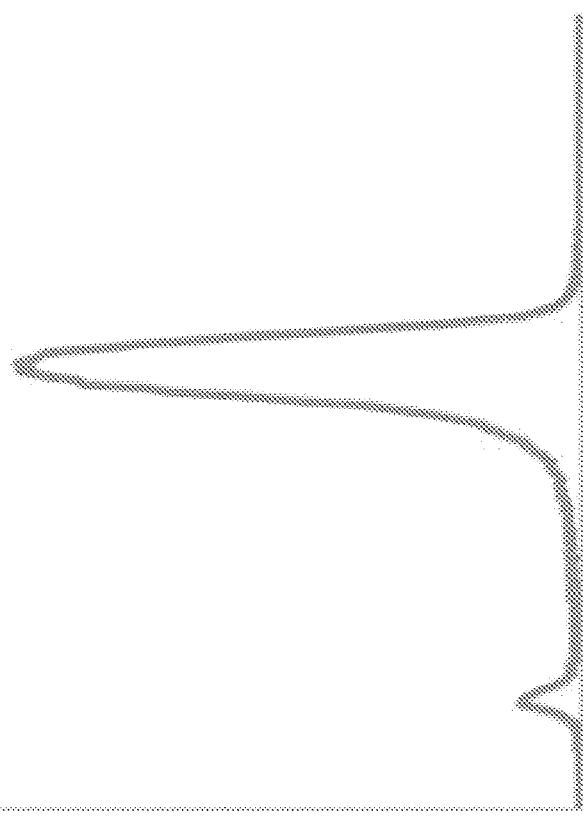
FIG. 5 illustrates intrinsic radiolabeling of $^{89}$Zr using PEGylated silica nanoparticles. The surface of silica nanoparticles was modified by the addition of 2,000 Da polyethylene glycol (PEG) according to the procedure reported herein. The red asterisk represents the activity remaining at the origin of the ITLC strip and the black asterisk represents the activity at the solvent front. Virtually all of the activity appears at the origin (for example, where the silica nanoparticles remain) in the PEGylated silica nanoparticle sample, whereas the control sample containing free PEG without silica exhibits the majority of activity at the solvent front. These results demonstrate that PEGylating silica nanoparticles does not preclude intrinsic radiolabeling.
Figure 5:
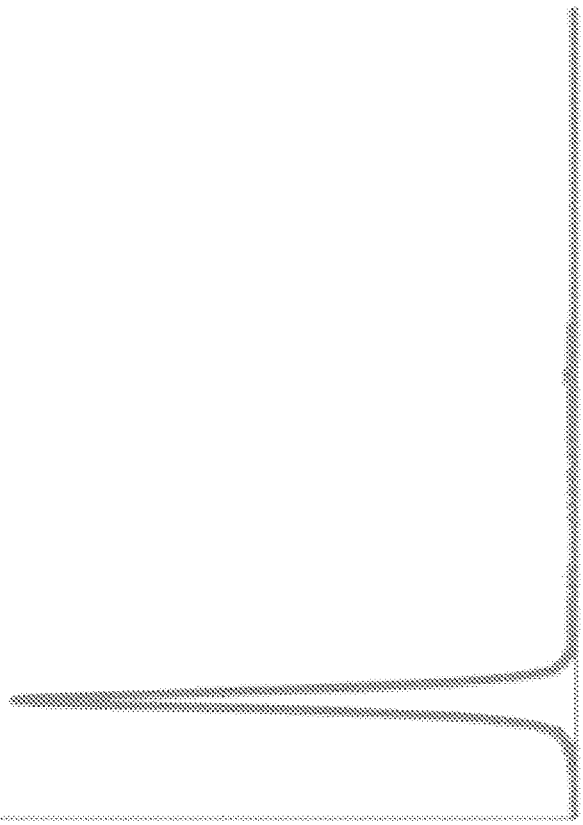

As shown in FIG. 5, in some embodiments, PEGylation of the silica nanoparticles does not preclude $^{89}$Zr binding. Therefore, attachment of moieties incompatible with the reported labeling procedure can be facilitated by first radiolabeling silica nanoparticles coated with functionalized polyethylene glycol, then performing post-radiolabeling reactions. The nanoparticle size and zeta potential before and after radiolabeling are provided in Table 1 below.

TABLE 1

Pre- and post-radiolabeling nanoparticle characterization. The size and zeta-potential of silica nanoparticles is not significantly affected by intrinsic radiolabeling.
Pre and post radiolabeling nanoparticle characteristics

| Radioisotope | Pre-labeling mean diameter (nm) | Post-labeling mean diameter (nm) | Pre-labeling zeta potential (mV) | Post-labeling zeta potential (mV) |
|---|---|---|---|---|
| $^{68}$Ga | 144.1 (±1.42) | 142.5 (±2.07) | −45.2 (±1.44) | −48.7 (±4.23) |
| $^{89}$Zr | 144.1 (±1.42) | 146.0 (±6.86) | −45.2 (±1.44) | −47.7 (±0.58) |
| $^{90}$Y | 144.1 (±1.42) | 145.4 (±0.30) | −45.2 (±1.44) | −47.4 (±3.25) |
| $^{177}$Lu | 144.1 (±1.42) | 141.6 (±2.98) | −45.2 (±1.44) | −45.1 (±3.16) |
| $^{111}$In | 144.1 (±1.42) | 143.4 (±0.85) | −45.2 (±1.44) | −42.1 (±0.51) |
| $^{64}$Cu | 144.1 (±1.42) | 145.0 (±1.00) | −45.2 (±1.44) | −47.7 (±3.34) |

$^{68}$Ga-silica nanoparticle radiolabeling. $^{68}$Ga ($t_{1/2}$=68 minutes) was eluted from a $^{68}$Ge-$^{68}$Ga generator (ANSTO, Australia) with 8-9 mCi activity per elution. After elution in 500 µL of 0.5 M potassium hydroxide, the $^{68}$Ga hydroxide solution was neutralized with concentrated hydrochloric acid, immediately added to silica nanoparticle solutions (10 nM, in 100 µL of 10 mM buffer) and incubated at the temperature and pH of interest on a thermomixer at 500 rpm. MES buffer was used for pH 5.5 and 7.3 solutions, while HEPES buffer was used for pH 8.8 solutions.

$^{89}$Zr-silica Nanoparticle Radiolabeling. $^{89}$Zr ($t_{1/2}$=78.4 h) was produced at Memorial Sloan Kettering Cancer Center on a TR19/9 cyclotron (Ebco Industries Inc.) via the $^{89}$Y(p, n)$^{89}$Zr reaction and purified to yield $^{89}$Zr-oxalate. $^{89}$Zr-oxalate was neutralized with 1.0 M sodium carbonate and added to silica nanoparticles solutions as described for $^{68}$Ga-silica nanoparticle radiolabeling.

$^{90}$Y-silica nanoparticle radiolabeling. $^{90}$Y ($t_{1/2}$=64 h) was obtained as yttrium (Y-90) chloride in 0.05 M HCl at an activity concentration of 25 mCi/mL (Nordion). $^{90}$Y was added to silica nanoparticle solutions as described for $^{68}$Ga-silica nanoparticle radiolabeling.

$^{111}$In-silica nanoparticle radiolabeling. $^{111}$In ($t_{1/2}$=2.8 days) was obtained as Indium (In-111) chloride in 0.05 M HCl at an activity concentration of 25 mCi/mL (Nordion). $^{111}$In was added to silica nanoparticle solutions as described for $^{68}$Ga-silica nanoparticle radiolabeling.

$^{64}$Cu-silica nanoparticle radiolabeling. $^{64}$Cu ($t_{1/2}$=12.7 h) was obtained from Washington University, St. Louis, where it was produced on a CS-15 cyclotron (Cyclotron Corp.) by the $^{64}$Ni(p,n)$^{64}$Cu reaction and purified to yield $^{64}$Cu chloride with a specific activity of 7.4-14.8 GBq/µg. $^{64}$Cu was added to silica nanoparticle solutions as described for $^{68}$Ga-silica nanoparticle radiolabeling.

$^{177}$Lu-silica nanoparticle radiolabeling. $^{177}$Lu ($t_{1/2}$=6.71 days) was obtained as Lutetium (Lu-177) chloride in 0.05N HCl at an activity concentration effective specific activity of 29.27 Ci/mg (PerkinElmer). $^{177}$Lu was added to silica nanoparticle solutions as described for $^{68}$Ga-silica nanoparticle radiolabeling.

Radiochemical Yield. To determine radiochemical yield (% of activity bound to particles), 1 µL samples were taken for ITLC at various time points over the course of 1 hour, using silica-gel impregnated ITLC paper (Varian), and analyzed on a Bioscan AR-2000 radio-TLC plate reader. For $^{68}$Ga, 0.1 M citric acid was used as the elution solvent, while 50 mM EDTA (pH 5) was used for all other isotopes. The red asterisk in FIG. 3 denotes the origin, where the nanoparticles remain, and the black asterisk denotes the solvent front, where the free activity would be located. Control samples absent of particles were run in identical conditions at each pH, with free activity moving with the mobile phase (denoted with a black asterisk in FIG. 3). With the exception of $^{177}$Lu, >95% of the control samples' (no particles) activity was located at the mobile phase front. $^{177}$Lu in in the buffer control showed activity at the origin for ITLC analysis because of precipitation. Thus, the amount of $^{177}$Lu bound to the particles was determined both by pelleting and comparing pellet versus supernatant activities, A 100 kD spin filtration cutoff filtration retains the particles on the filter while free $^{177}$Lu is found in the flow-through. To purify particles, the solution was centrifuged at 10,000 rpm for 5 minutes, the supernatant removed and counted, and the product re-dispersed in 10 mM MES and sonicated. The final radiochemical yield reported was measured by centrifugal nanoparticle purification (% activity bound to the pellet).

Figure 3:
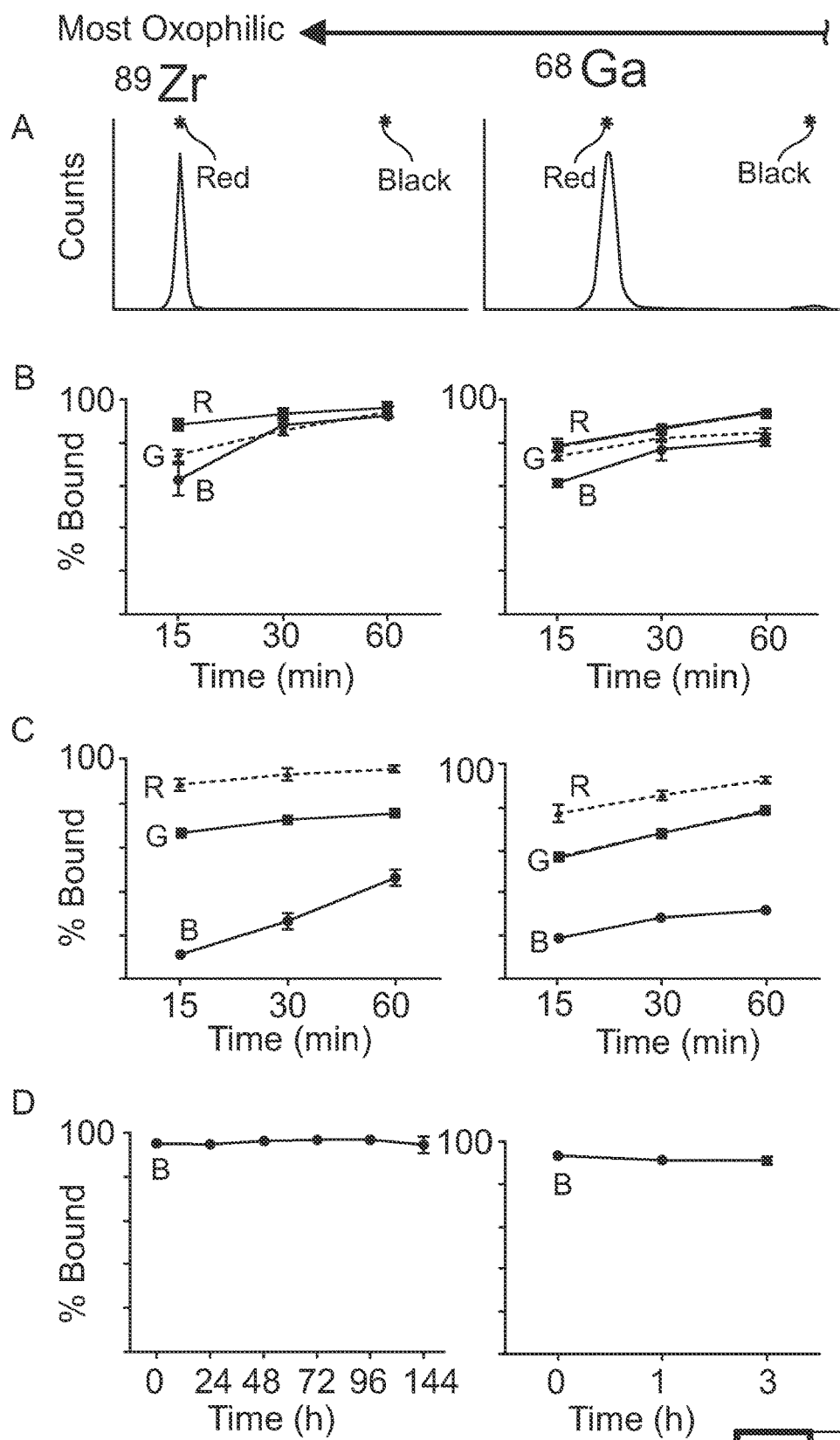
FIGS. 3A-3D illustrate radiolabeling and serum stability of silica nanoparticles.
Figure 3:
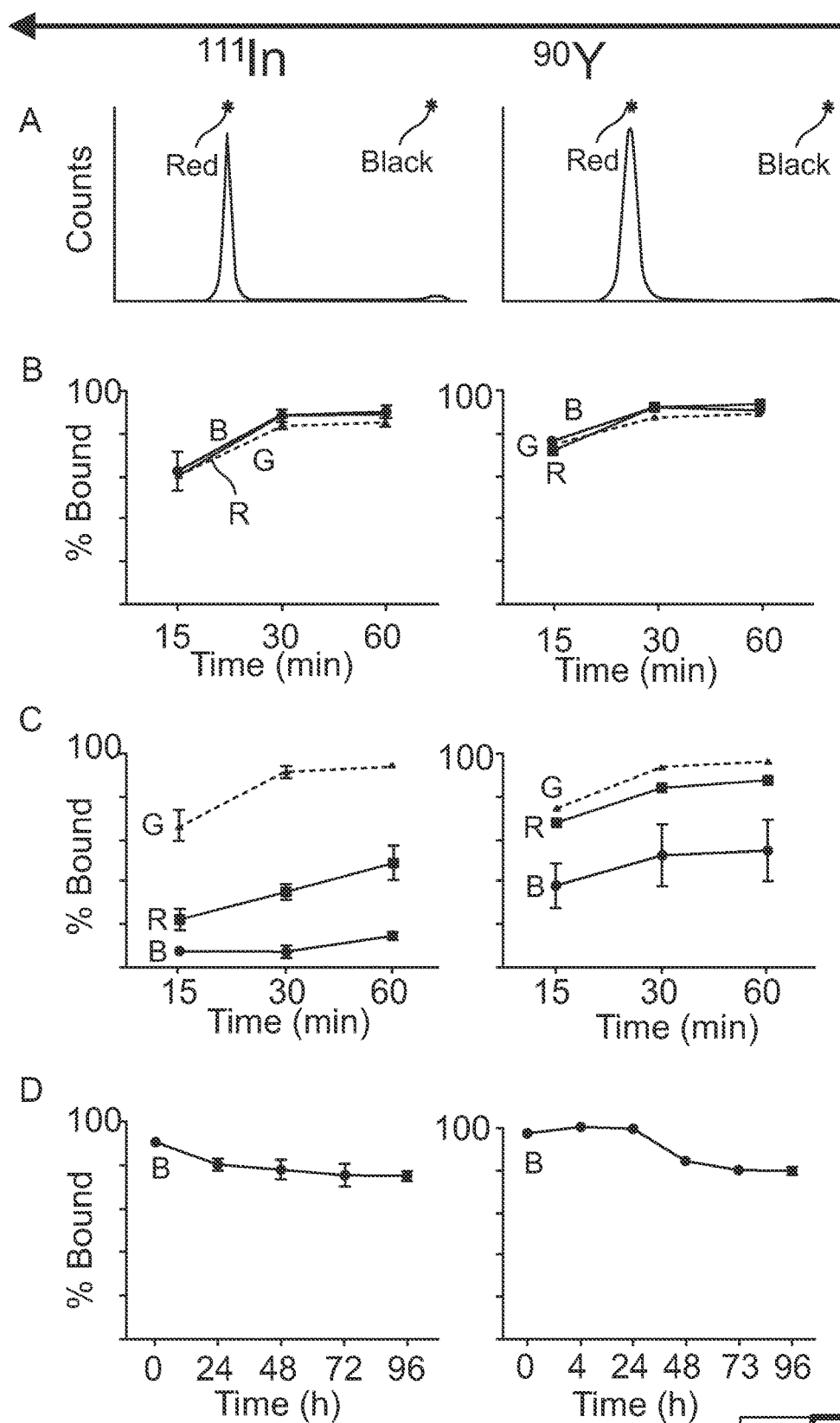
Figure 3:
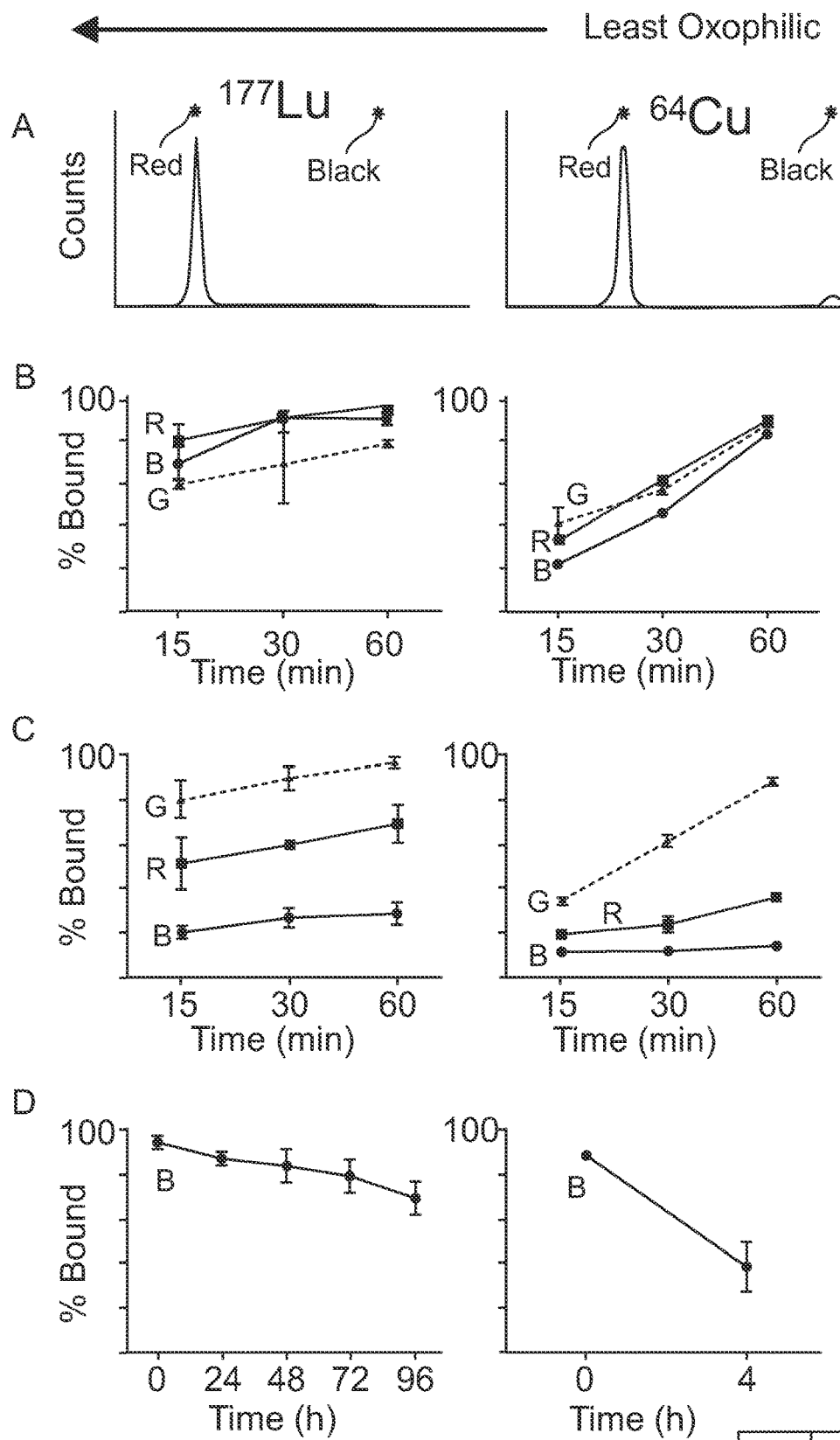

Serum Stability. Stability of silica nanoparticles was evaluated under physiological conditions. Serum stability experiments were performed at 37° C. in 50% fetal bovine serum (FBS, Gemini Bio-products), 50% MES (total volume 150 µL), on an Eppendorf thermomixer at 550 rpm for each isotope over time periods appropriate to each isotope's half-life. Both ITLC and size exclusion filtration analysis was completed at reported time points and analyzed as previously described. Reported values in FIG. 3 are ITLC results, which showed more free activity for every isotope and was therefore considered a more robust method than SE filtration. All isotopes were stably retained within the silica nanoparticles except for $^{64}$Cu. In the case of copper, 50% of the bound isotope leached into the serum after 4 h. Since the operating principle of intrinsic labeling with silica nanoparticles is the affinity each isotope has for the oxygen-rich matrix, it is unsurprising that copper is most weakly retained because it is the least oxophilic of the isotopes tested. In fact, the trend in serum stability of the intrinsically labeled silica demonstrated excellent correlation with the oxophilicity (i.e., hardness) of the ions. The marked decrease in the serum stability of $^{64}$Cu can be further attributed to proteins present in the serum that actively chelate copper ions, resulting in pronounced transchelation effects.

Animal Models. All animal experiments were done in accordance with protocols approved by the Institutional Animal Care and Use Committee of Memorial Sloan-Kettering Cancer Center and followed National Institutes of Health guidelines for animal welfare.

PET and Biodistribution: Stability and biodistribution of $^{68}$Ga- or $^{89}$Zr-labeled silica nanoparticles was investigated in vivo $^{68}$Ga- or $^{89}$Zr have increased clinical importance in PET imaging and excellent serum stability. Because nanoparticles are known to generally accumulate in the reticuloendothelial system in amounts well exceeding 90% of the injected dose, short-lived isotopes like $^{68}$Ga are attractive in minimizing the cross-dose to healthy organs while still enabling whole-body cancer imaging. Alternatively, because some nanoparticle formulations remain in circulation for extended periods and most nanoparticle clearance studies extend for weeks or longer, long-lived isotopes like $^{89}$Zr are essential for investigating the biological response to nanoparticle administration. An additional benefit of studying these two isotopes is that the biodistribution of free $^{68}$Ga and $^{89}$Zr is easily distinguished the biodistribution of nanoparticles in that they do not preferentially residualize in the liver and spleen (FIG. 6A-6B), in contrast to other isotopes like $^{64}$Cu that naturally accumulate in the liver. Male Nude athymic mice (8-10 weeks old, n=3) were injected with 250-350 µCi (9.25-12.95 MBq) of either free $^{68}$Ga- or $^{89}$Zr-silica nanoparticles (10 nMol) in 100 µL of 10 mM pH=7.3 2-(N-morpholino)-ethanesulfonic acid solution (MES solution) via the lateral tail vein. At predetermined time points (1 hour, 4 hours, and 24 hours) animals were anesthetized with isoflurane (Baxter Healthcare, Deerfield, Ill.) and oxygen gas mixture (2% for induction, 1% for maintenance) and scans were then performed using an Inveon PET/CT scanner (Siemens Healthcare Global) Whole body PET static scans were performed recording a minimum of 50 million coincident events, with scan duration of 10-20 minutes. The energy and coincidence timing windows were 350-750 keV and 6 ns, respectively. The image data were normalized to correct for non-uniformity of response of the PET, dead-time count losses, positron branching ratio, and physical decay to the time of injection, but no attenuation, scatter, or partial-volume averaging correction was applied. Images were analyzed using ASIPro VMTM software (Concorde Micro-systems).

For biodistribution studies, mice were euthanized by $CO_2$(g) asphyxiation at 4 hours ($^{68}$Ga) and 24 hours ($^{89}$Zr) post-injection. After asphyxiation, organs were removed, weighed, and counted in a γ counter calibrated for either $^{68}$Ga or $^{89}$Zr. Counts were background- and decay-corrected to the injection time, converted to µCi using calibrated standards, and the percent injected dose per gram (% ID/g) determined by normalization to the total activity injected.

Nanoparticle-bound isotopes demonstrated the known biodistribution of silica nanoparticles and remained localized in the liver and spleen for the entire period investigated (3 hours for $^{68}$Ga, 24 hours for $^{89}$Zr, n=3 for each), as shown, for example in FIGS. 6A-6B. As shown in FIGS. 6A-6C, the stark contrast between the free and nanoparticle-bound biodistributions demonstrates that the silica nanoparticles stably retain the isotopes in vivo.

CT: Whole body standard low magnification CT scans were performed with the X-ray tube setup at a voltage of 80 kV and current of 500 µA. The CT scan was acquired using 120 rotational steps for a total of 220 degrees yielding and estimated scan time of 120 s with an exposure of 145 ms per frame.

PET/CT lymph node studies with $^{89}$Zr-silica nanoparticles. Silica serves as a robust platform for binding radioisotopes and retaining them in vivo. In some embodiments, kit-like radiolabeling protocols discussed herein can be immediately useful in a wide variety of known biomedical applications of nanoparticles. In some conducted experiments, as a proof of concept, nanoparticles discussed herein were used for lymph node imaging, which is a clinically important applications. For in vivo silica nanoparticle-radiometal lymph node imaging studies, 3 mice were injected in the foot pad with $^{89}$Zr in saline and 3 mice were injected with 100-150 μCi of $^{89}$Zr-silica nanoparticles (10 mM MES, 20-30 μL, 3.7-5.5 MBq) for a total of 6 mice. All mice were induced with 2.5% isoflurane and maintained on 2-2.5% isoflurane in preparation for the scans. Whole body scans were performed using Inveon Multimodality (MM) CT scanner (Siemens) and Inveon dedicated PET scanner for a total of 15-45 min. In all cases, the nanoparticle-bound radioisotopes enabled robust detection of local lymph nodes while the free radioisotope controls did not, as shown, for example in FIGS. 8 and 9.

AFM analysis of silica nanoparticles. An Asylum Research MFP-3D-BIO was used to image the nanoparticles in tapping mode. Nanoparticles in 100% EtOH were deposited onto AP-mica and allowed to air dry, creating a flat layer of densely packed nanoparticles to facilitate imaging. Olympus AC160 probes were tuned to 500 mV and imaged at 80% of free amplitude. A new probe was used for each image to ensure that tip convolution did not contribute to any differences in measurements. Scan parameters were kept the same between scans to avoid any contribution to measured differences. Samples were imaged multiple times to verify trends. The phase image was observed for any differences in the material properties of the nanoparticles, including individual pore sizes.

Pegylation of silica nanoparticles. Silica nanoparticles were incubated in 2% (v/v) MPTMS in EtOH at 70° C. for 90 minutes to introduce SH groups at the nanoparticle surface. After washing multiple times in EtOH and pH=7.1 MES buffer, the thiolated silica nanoparticles were incubated with 1% (w/v) maleimide-terminated poly(ethylene glycol) in 100 mM pH=7.1 MES buffer for 1 h. The nanoparticles were washed several times in MES buffer.

Example 2: Exemplary Protocol for Synthesis of Chelator-Free PET-SE(R)RS Nanoparticles SERRS Nanoparticle Synthesis Gold nanoparticle cores were synthesized by adding 1.5 ml of 1 weight % sodium citrate to 200 mL of boiling 0.01 weight % aqueous HAuCl$_4$. The nanoparticle cores were collected by centrifugation (10 min, 4000 g, 4° C.) and dialyzed (3.5 kDa molecular weight cutoff; Slide-A-Lyzer G2, Thermo Fisher Scientific Inc.) against 18.2-megohm-cm water. Dialyzed gold nanoparticles (~55 nm) were directly coated with dye-embedded silica via a modified Stöber method without the need for surface priming. In brief, 1.0 ml of 3.0 nM gold nanoparticles in water was added to 8.5 ml of ethanol to which 15 ml of 25 mM resonant dye molecule (e.g., IR-780 perchlorate) in DMF, 320 ml of tetraethyl orthosilicate (TEOS), and 130 ml of 28% ammonium hydroxide were added and allowed to react for 25 min. The as-synthesized SE(R)RS nanoparticles were isolated by centrifugation (3500 g, 10 minutes) and washed several times with ethanol.

Silica Nanoparticle Synthesis

Silica nanoparticles were synthesized according to a modified Stober method. Briefly, 3.75 mL of ultrapure H$_2$O was added to 25 mL of ethanol and 1.25 mL TEOS. The reaction was initiated by the addition of 0.625 mL of 28% ammonium hydroxide and washed three times in ethanol after the nanoparticles had reached the desired size.

Chelator-Free Radiolabeling

Radioisotopes are obtained and neutralized to pH=7 in a suitable buffer (e.g., MES). The desired amount of activity (e.g. 100-500 mCi) is added to the nanoparticle dispersion in pH=7 buffer (10 nM nanoparticles in 100 μL of 10 mM buffer) and shaken in a thermomixer. The labeling can proceed for various times and temperatures, but are typically in the range of 25-70° C. and for a time duration between 1-45 minutes. A neutral pH is not a requirement for successful labeling. In some embodiments, a neutral pH provides consistently good results for silica and SE(R)RS nanoparticles.

Other Embodiments and Equivalents

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

What is claimed is:

1. A method of preparing medical isotope labeled metal (loid) chalcogen nanoparticles, the method comprising steps of:
   supplying a reaction mixture comprising:
      metal(loid) chalcogen nanoparticles selected from the group consisting of metalloid chalcogen nanoparticles and metal(loid) chalcogen-coated metal nanoparticles, and
      medical isotopes selected from the group consisting of PET-active radioisotopes, SPECT-active radioisotopes, MRI-active metals, and therapeutic radioisotopes,
   which reaction mixture is substantially free of chelator; and
   maintaining the reaction mixture under conditions and for a time sufficient for the medical isotopes to directly bind to the metal(loid) chalcogen nanoparticles, thereby forming the medical isotope labeled metal (loid) chalcogen nanoparticles
   wherein the conditions comprise heating the reaction mixture to a temperature of equal to or greater than 25° C.

2. The method of claim 1, further comprising a step of isolating the medical isotope labeled metal(loid) chalcogen nanoparticles.

3. The method of claim 2, wherein the step of isolating the medical isotope labeled metal(loid) chalcogen nanoparticles comprises centrifuging the reaction mixture or filtrating the reaction mixture.

4. The method of claim 2, further comprising dispersing the isolated medical isotope labeled metal(loid) chalcogen nanoparticles in an infusion fluid.

5. The method of claim 1, wherein the time is between 5 and 120 minutes.

6. The method of claim 1, further comprising administering the medical isotope labeled metal(loid) chalcogen nanoparticles to a subject in vivo.

7. The method of claim 1, wherein integrity of the medical isotope labeled metal(loid) chalcogen nanoparticles is not affected by the steps.

8. The method of claim 1, wherein the metal(loid) chalcogen nanoparticles are doped with a fluorescent agent.

9. The method of claim 1, wherein the metal(loid) chalcogen nanoparticles are doped with a metal or a semi-metal.

10. The method of claim 1, wherein the metal(loid) chalcogen nanoparticles are doped with a non-metal.

11. The method of claim 1, wherein the metal(loid) chalcogen nanoparticles are doped with a combination of at least two materials selected from the list consisting of fluorescence agents, metals, semi-metals, and non-metals.

12. The method of claim 1, wherein binding between the metal(loid) chalcogen nanoparticles and the medical isotope is covalent.

13. The method of claim 1, wherein binding between the metal(loid) chalcogen nanoparticles and the medical isotope is non-covalent.

14. The method of claim 13, wherein binding between the metal(loid) chalcogen nanoparticles and the medical isotope is via chelate bonds.

15. The method of claim 1, wherein the metal(loid) chalcogen nanoparticles have a longest dimension between 2-1000 nm.

16. The method of claim 1, wherein the conditions comprise heating the reaction mixture to a temperature of between 45° C. and 80° C.

17. The method of claim 1, wherein the conditions comprise heating the reaction mixture to a temperature of equal to or greater than 95° C.

18. The method of claim 15, wherein the metal(loid) chalcogen nanoparticles have a longest dimension between 2-800 nm.

19. The method of claim 15, wherein the metal(loid) chalcogen nanoparticles have a longest dimension between 2-500 nm.

20. The method of claim 15, wherein the metal(loid) chalcogen nanoparticles have a longest dimension between 2-200 nm.

* * * * *